(12) United States Patent
Uehara et al.

(10) Patent No.: US 10,646,705 B2
(45) Date of Patent: May 12, 2020

(54) MALE CONNECTOR

(71) Applicant: JMS CO., LTD., Hiroshima-shi, Hiroshima (JP)

(72) Inventors: Yasumasa Uehara, Hiroshima (JP); Yutaka Ueda, Hiroshima (JP); Kazuhiko Takimoto, Hiroshima (JP); Megumi Harada, Hiroshima (JP)

(73) Assignee: JMS CO., LTD., Hiroshima (JP)

( * ) Notice: Subject to any disclaimer, the term of this patent is extended or adjusted under 35 U.S.C. 154(b) by 32 days.

(21) Appl. No.: 15/103,165

(22) PCT Filed: Dec. 9, 2014

(86) PCT No.: PCT/JP2014/082567
§ 371 (c)(1),
(2) Date: Jun. 9, 2016

(87) PCT Pub. No.: WO2015/087881
PCT Pub. Date: Jun. 18, 2015

(65) Prior Publication Data
US 2016/0354594 A1    Dec. 8, 2016

(30) Foreign Application Priority Data
Dec. 11, 2013   (JP) .................................. 2013-256270

(51) Int. Cl.
*A61M 39/10*   (2006.01)
*A61J 15/00*   (2006.01)

(52) U.S. Cl.
CPC .............. *A61M 39/10* (2013.01); *A61J 15/00* (2013.01); *A61M 39/1011* (2013.01); *A61M 2039/1033* (2013.01); *A61M 2039/1088* (2013.01)

(58) Field of Classification Search
CPC .. A61J 15/0026; A61J 15/00; A61M 39/1011; A61M 39/1055; A61M 39/10;
(Continued)

(56) References Cited

U.S. PATENT DOCUMENTS 5,456,676 A    10/1995  Nelson et al.
5,509,911 A *   4/1996  Cottone, Sr. ...... A61M 39/1055
                                                    285/315
(Continued)

FOREIGN PATENT DOCUMENTS

CN    102970960    3/2013
JP    3-237984     10/1991
(Continued)

OTHER PUBLICATIONS

Office Action issued in corresponding Chinese Patent Application No. 201480067331.5, dated Jul. 3, 2018, 27 pages with an English translation.
(Continued)

*Primary Examiner* — Kevin C Sirmons
*Assistant Examiner* — Tezita Z Watts
(74) *Attorney, Agent, or Firm* — Hamre, Schumann, Mueller & Larson, P.C.

(57) ABSTRACT

The male connector (1) includes a connector body (10) and a lock nut (50). The connector body (10) includes a male luer (11), first female threading (41) that surrounds the male luer (11), a base end portion (20) that is inserted into a tube (8), a fixed protrusion (21) formed on the base end portion (20), and a spiral protrusion (32) between the male luer (11) and the base end portion (20). The lock nut (50) includes second female threading (52) that is screwed together with the spiral protrusion (32). When the spiral protrusion (32) and the second female threading (52) are screwed together, the base end portion (20) and the lock nut (50) clamp the tube (8).

(Continued)

First rotation prevention mechanisms (14, 54) that engage with one another are provided on the connector body (10) and the lock nut (50) such that the lock nut (50) does not rotate relative to the connector body (10) when the tube (8) is clamped.

15 Claims, 58 Drawing Sheets

(58) Field of Classification Search
CPC .......... A61M 39/12; A61M 2039/1033; A61M 2039/1038; A61M 2039/1094
See application file for complete search history.

(56) References Cited

U.S. PATENT DOCUMENTS

| | | | |
|---|---|---|---|
| 6,260,890 | B1 | 7/2001 | Mason |
| 6,595,964 | B2 * | 7/2003 | Finley ................. A61M 39/045 251/149.1 |
| 7,396,051 | B2 * | 7/2008 | Baldwin ............... A61M 39/26 285/354 |
| 8,585,099 | B2 * | 11/2013 | Nielson .................. F16L 19/08 285/247 |
| 8,777,931 | B2 * | 7/2014 | Davis .................... A61M 39/10 604/533 |
| 2002/0147429 | A1 | 10/2002 | Cowan |
| 2003/0120260 | A1 | 6/2003 | Chu |
| 2008/0054632 | A1 | 3/2008 | Funamura et al. |
| 2010/0176584 | A1 * | 7/2010 | Ito ......................... A61M 39/10 285/23 |
| 2012/0192968 | A1 * | 8/2012 | Bonnal ................. A61M 39/26 137/454.2 |
| 2013/0144246 | A1 | 6/2013 | Takemoto |

FOREIGN PATENT DOCUMENTS

| | | | | |
|---|---|---|---|---|
| JP | 2008/152871 | | 12/2008 | |
| JP | 5218560 | B2 * | 6/2013 | ........ A61M 39/1011 |
| WO | WO-2010029853 | A1 * | 3/2010 | ........ A61M 39/1011 |
| WO | WO 2011029853 | A1 * | 3/2011 | ....... H04N 21/23439 |
| WO | WO-2011029853 | A1 * | 3/2011 | .......... H04N 21/6375 |
| WO | 2012/105892 | | 8/2012 | |

OTHER PUBLICATIONS

International Search Report for PCT/JP2014/082567, dated Mar. 3, 2015, 2 pages.

Extended European Search Report issued in corresponding European Patent Application 14869083, dated Sep. 12, 2017, 10 pages.

Office Action issued in corresponding Chinese Patent Application No. 201480067331.5, dated Mar. 14, 2019, 25 pages with translation.

* cited by examiner

MALE CONNECTOR

TECHNICAL FIELD

The present invention relates to a male connector provided at the upstream end of a tube used in enteral feeding.

BACKGROUND ART

Enteral feeding is known as a method for administering nutrition and drugs to a patient without relying on oral administration. In enteral feeding, liquids such as nutrients, liquid food, and drugs (generally called "enteral nutrients") are administered to a patient via a transnasal catheter that has been inserted through the patient's nasal cavity and into their stomach or duodenum, or via a PEG (Percutaneous Endoscopic Gastrostomy) catheter that has been inserted into a gastrostomy formed in the patient's abdomen. The liquid to be administered to the patient is stored in a container. A bendable tube (referred to hereinafter as a "container-side tube") is connected to the outlet port of the container. The downstream end of the container-side tube is connected to the upstream end of a catheter that has been inserted into the patient (transnasal catheter, PEG catheter, or the like), or the upstream end of a bendable tube that is connected to the catheter (collectively referred to hereinafter as a "patient-side tube"). In general, a connector tool made up of a male connector and a female connector is used to connect the container-side tube and the patient-side tube. Conventionally, the male connector is provided at the downstream end of the container-side tube, and the female connector is provided at the upstream end of the patient-side tube (e.g., see Patent Document 1).

If the liquid administered in enteral feeding is a liquid that has a low viscosity, problems occur, such as the liquid flowing backwards from the stomach to the esophagus and developing into pneumonia, or the patient suffering from diarrhea caused by moisture in the liquid not being sufficiently absorbed in the body. In view of this, in enteral feeding, the liquid is often given a higher viscosity (i.e., semi-solidified) by the addition of a thickening agent or a thickener, for example. Such a liquid that has been given a higher viscosity has a low fluidity, and thus has a high resistance when passing through a tube. Accordingly, when a liquid that has been given a higher viscosity is administered to a patient, pressure is applied to the liquid to pressure-feed it.

For this reason, there is desire for the connector tool that connects the container-side tube and the patient-side tube to include lock mechanisms that engage with each other in order to be able to withstand the pressure applied to the liquid. In view of this, international standard ISO 80369-3 regarding nutrition-related medical equipment has been given consideration for the international standardization of male connectors and female connectors for use in such applications.

As shown in FIGS. 24A and 24B, a male connector 910 under consideration as ISO 80369-3 has a tubular male luer 911 and an outer tube 913 that surrounds the male luer 911. An outer circumferential face 912 of the male luer 911 is a tapered face whose outer diameter decreases as it approaches the tip (a so-called male tapered face). A channel 917 that passes through the male luer 911 along the lengthwise direction thereof is formed in the male luer 911. Female threading 916 is formed in the inner circumferential face of the outer tube 913 that opposes the male luer 911.

On the other hand, as shown in FIGS. 25A and 25B, a female connector 920 under consideration as ISO 80369-3 has a cylindrical insertion portion (female luer) 921 into which the male luer 911 is inserted. An inner circumferential face 922 of the insertion portion 921 is a tapered face whose inner diameter increases as it approaches the tip (a so-called female tapered face). Male threading 926 is formed on the outer circumferential face of the insertion portion 921.

The male connector 910 and the female connector 920 are connected by inserting the male luer 911 into the insertion portion 921 and screwing the female threading 916 and the male threading 926 together. Since the outer circumferential face 912 of the male luer 911 and the inner circumferential face 922 of the insertion portion 921 are tapered faces that have the same taper angle, they come into liquid-tight surface contact with each other. The female threading 916 and the male threading 926 that are screwed together constitute lock mechanisms for locking the connected state of the male connector 910 and the female connector 920. The male connector 910 and female connector 920 provide a connection having excellent liquid-tightness (property of preventing the leakage of a liquid from the connection portion of the male connector and the female connector even if pressure is applied to the liquid) and excellent connection strength (property of preventing separation of the connected male connector and female connector even if pulling force is applied).

In the international standard ISO 80369-3, consideration has been given to providing the male connector 910 at the upstream end of the patient-side tube and providing the female connector 920 at the downstream end of the container-side tube in order to prevent mistaken connection with a connector used in a field other than enteral nutrition.

PRIOR ART DOCUMENTS

Patent Document

[Patent Document 1] WO 2008/152871

DISCLOSURE OF INVENTION

Problem to be Solved by the Invention

In the male connector 910, the outer tube 913 surrounds the male luer 911, and the female threading 916 is formed in the inner circumferential face of the outer tube 913. Accordingly, enteral nutrients easily become stuck in the gap between the male luer 911 and the outer tube 913, and in the valley of the female threading 916 in particular. Once an enteral nutrient becomes stuck in the valley of the female threading 916, it is difficult to wipe away that enteral nutrient. If an enteral nutrient becomes stuck for a long period of time, the male connector 910 can become unsanitary. Eventually, it is possible that bacteria will breed in the male connector 910, enter the patient's body, and cause a serious complication.

There are cases where a catheter inserted into a patient remains indwelled in the patient over a long period of time. For example, a PEG catheter is normally replaced every 1 to 3 months. If the male connector 910 is provided at the upstream end of such a catheter, there is desire for the ability to remove the male connector 910 from the catheter indwelled in the patient in order to clean or replace the male connector 910.

One known method of installing a gastrostomy is a method of inserting a catheter into a patient's stomach through their mouth, and then drawing the tip (upstream end) of the catheter out of the patient's body through their abdomen. In the case of installing a gastrostomy using this method, if the male connector 910 is attached to the tip of the catheter in advance, the male connector 910, which is a hard member, makes it difficult to perform the operation of passing the catheter through the patient's body. Accordingly, there is desire for the ability to remove the male connector from the catheter so that the male connector can be attached to the catheter after the catheter has been indwelled in the patient.

On the other hand, the male connector needs to be firmly fixed to the patient-side tube in order to prevent the leakage of an enteral nutrient and unintended separation of the male connector.

An object of the present invention is to provide a male connector that includes female threading that surrounds a male luer, and that can be removably and firmly attached to a tube.

Means for Solving Problem

A male connector according to one aspect of the present invention is a male connector that is removably attached to an upstream end of a tube used in enteral feeding, and includes a connector body and a lock nut. The connector body includes a tubular male luer in which a channel in communication with the tube is formed, first female threading that surrounds the male luer, a base end portion that is inserted into the tube, and a spiral protrusion that protrudes outward between the male luer and the base end portion. The lock nut has a hollow tubular shape and is open at two ends, and includes second female threading that is screwed together with the spiral protrusion. When the spiral protrusion and the second female threading are screwed together, the base end portion and the lock nut clamp the tube in which the base end portion is inserted. First rotation prevention mechanisms that engage with one another are provided on the connector body and the lock nut such that the lock nut does not rotate relative to the connector body when the tube is clamped.

Effects of the Invention

The male connector of the present invention is constituted by the connector body and the lock nut, and thus can be easily removed from the tube. On the other hand, the base end portion and the lock nut clamp the tube when the male connector is attached to the tube, and therefore the male connector can be firmly attached to the tube.

The first rotation prevention mechanisms prevent the lock nut from rotating relative to the connector body. Accordingly, it is possible to reduce the possibility of the screwing together of the spiral protrusion and the second female threading from becoming loosened unintentionally.

DESCRIPTION OF THE INVENTION

Figure 1A:
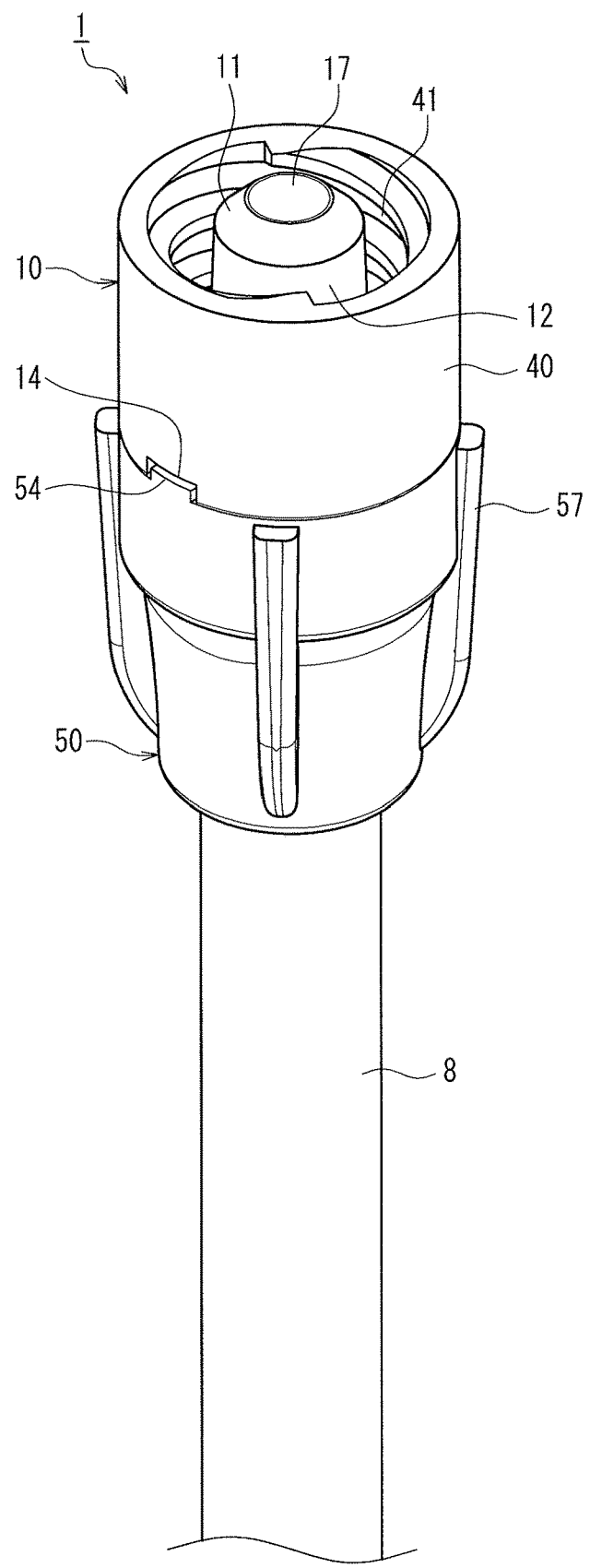
FIG. 1A is a perspective view of a male connector according to Embodiment 1 of the present invention.

In the above-described male connector of the present invention, the lock nut may include a small diameter portion that opposes the tube. In this case, it is preferable that when the spiral protrusion and the second female threading are screwed together, the base end portion and the small diameter portion clamp the tube in which the base end portion is inserted. According to this configuration, the male connector can be firmly attached to the tube with a simple configuration.

The connector body may include a fixed protrusion that protrudes outward and is formed on an outer circumferential face of the base end portion. In this case, it is preferable that when the spiral protrusion and the second female threading are screwed together, the fixed protrusion and the small diameter portion clamp the tube in which the base end portion is inserted. According to this configuration, the male connector can be firmly attached to the tube with a simple configuration.

The first rotation prevention mechanisms may be formed on a flange that protrudes outward from a position of the connector body between the male luer and the spiral protrusion, and on an end face, on a second female threading side, of the lock nut. According to this configuration, it is possible to realize first rotation prevention mechanisms that engage with each other in the circumferential direction.

Alternatively, the first rotation prevention mechanisms may be formed on an outer circumferential face of the connector body between the base end portion and the spiral protrusion, and on an inner circumferential face of the lock nut (preferably, the inner circumferential face between the second female threading and the small diameter portion). According to this configuration, it is possible to realize first rotation prevention mechanisms that engage with each other in the central axis direction.

The first rotation prevention mechanisms can include a protruding portion formed on one of the connector body and the lock nut, and a receding portion formed on another one of the connector body and the lock nut. The protruding portion and the receding portion can engage in a circumferential direction. The protruding portion may include an inclined face on one side in the circumferential direction, and include a vertical face on another side in the circumferential direction. In this case, it is preferable that the receding portion includes an inclined face and a vertical face that respectively oppose the inclined face and the vertical face of the protruding portion when the protruding portion is fitted into the receding portion. According to this configuration, it is possible to reduce the possibility of the connector body and the lock nut becoming separated unintentionally, while the operation of connecting the lock nut to the connector body is relatively easy.

It is preferable that the male connector can be connected to a female connector that includes an insertion portion for insertion of the male luer and male threading that is to be screwed together with the first female threading. In this case, it is preferable that the first rotation prevention mechanisms are configured such that when the lock nut and the female connector are rotated in mutually opposite directions in order to separate the male connector and the female connector that are connected to each other, screwing together of the first female threading and the male threading is loosened, without the lock nut rotating relative to the connector body. According to this configuration, the male connector and the female connector can be separated without the male connector becoming disassembled.

The connector body may be constituted by two parts, namely a luer portion having the male luer, the base end portion, and the spiral protrusion, and a lock portion having the first female threading. In this case, the lock portion has a hollow tubular shape and is open at two ends, and can be removably attached to the luer portion. It is preferable that second rotation prevention mechanisms that engage with one another are provided on the luer portion and the lock portion such that the lock portion does not rotate relative to the luer portion. According to this configuration, the connector body is constituted by two parts, namely the luer portion and the lock portion, and therefore the connector body can be cleaned easily. The second rotation prevention mechanisms prevent the lock portion from rotating relative to the luer portion, and therefore even though the male connector is constituted by three parts, the operability of the connection and separation of the male connector to and from the female connector does not decrease.

It is preferable that the male connector can be connected to a female connector that includes an insertion portion for insertion of the male luer and male threading that is to be screwed together with the first female threading. In this case, it is preferable that the second rotation prevention mechanisms are configured such that when the lock nut and the female connector are rotated in mutually opposite directions in order to separate the male connector and the female connector that are connected to each other, screwing together of the first female threading and the male threading is loosened, without the lock portion rotating relative to the luer portion. According to this configuration, the male connector and the female connector can be separated without the lock portion becoming separated from the luer portion.

It is preferable that a liquid-tight seal between the luer portion and the lock portion is formed at a position on a base end portion side relative to the male luer. According to this configuration, it is possible to prevent a nutrient from leaking out from between the luer portion and the lock portion.

It is preferable that the liquid-tight seal is formed by fitting together of a male tapered face formed on the luer portion and a female tapered face formed on the lock portion. According to this configuration, the liquid-tight seal can be formed with a simple configuration. Also, the liquid-tight seal can be formed by merely attaching the lock portion to the luer portion.

The connector body may include an extension portion arranged outward of the lock nut. In this case, it is preferable that the extension portion is configured such that rotation torque can be applied to the male connector via the extension portion. According to this configuration, rotation torque applied to the extension portion is transmitted to the first female threading without passing through the first rotation prevention mechanisms. Accordingly, even in the case where the male connector and the female connector have been screwed together firmly, it is possible to loosen the screwing together thereof by applying a large amount of rotation torque to the extension portion.

The extension portion can include at least one bar-shaped member that extends parallel with a lengthwise direction of the connector body. The at least one bar-shaped member is arranged so as to protrude outward from an outer circumferential face of the lock nut. According to this configuration, an extension portion to which rotation torque can be applied can be configured with a simple configuration. Also, due to the extension portion including at least one bar-shaped member, there is an improvement in the operability of connection to and separation from the female connector, and an improvement in the operability of cleaning the connector body.

It is preferable that the male luer and the first female threading are compliant with ISO 80369-3. According to this configuration, the male connector of the present invention and a female connector compliant with ISO 80369-3 can be connected with excellent liquid-tightness and excellent connection strength.

It is preferable that at least one of the connector body and the lock nut includes a protrusion (convex portion) or recession (concave portion) for facilitating attachment and detachment of the lock nut to and from the connector body.

According to this configuration, there is an improvement in the operability of the attachment and separation of the lock nut to and from the connector body. Similarly, it is preferable that the lock portion includes a protrusion or recession for facilitating attachment and detachment of the lock portion to and from the luer portion. According to this configuration, there is an improvement in the operability of the attachment and separation of the lock portion to and from the luer portion. The protrusion or recession may be configured so as to be directly gripped by an operator, or may be configured so as to engage with a jig gripped by the operator.

The male connector of the present invention may further include a jig configured so as to engage with the protrusion or recession. In this case, it is preferable that the jig is configured such that rotation torque can be applied to the connector body or the lock nut via the jig. According to this configuration, the attachment and separation of the lock nut to and from the connector body, or the attachment and separation of the lock portion to and from the luer portion can be performed easily.

Hereinafter, the present invention will be described in detail while disclosing preferred embodiments. Note that, it goes without saying that the present invention is not limited to the following embodiments. For the sake of convenience in the description, the drawings that are referenced in the following description show simplifications of, among the constituent members of the embodiments of the present invention, only relevant members that are necessary for describing the present invention. The present invention can therefore include arbitrary constituent members that are not shown in the following drawings. Also, the dimensions of the actual constituent members, the ratios of the dimensions of the members, and the like are not shown faithfully in the drawings referenced below.

Embodiment 1

Configuration

Figure 1B:
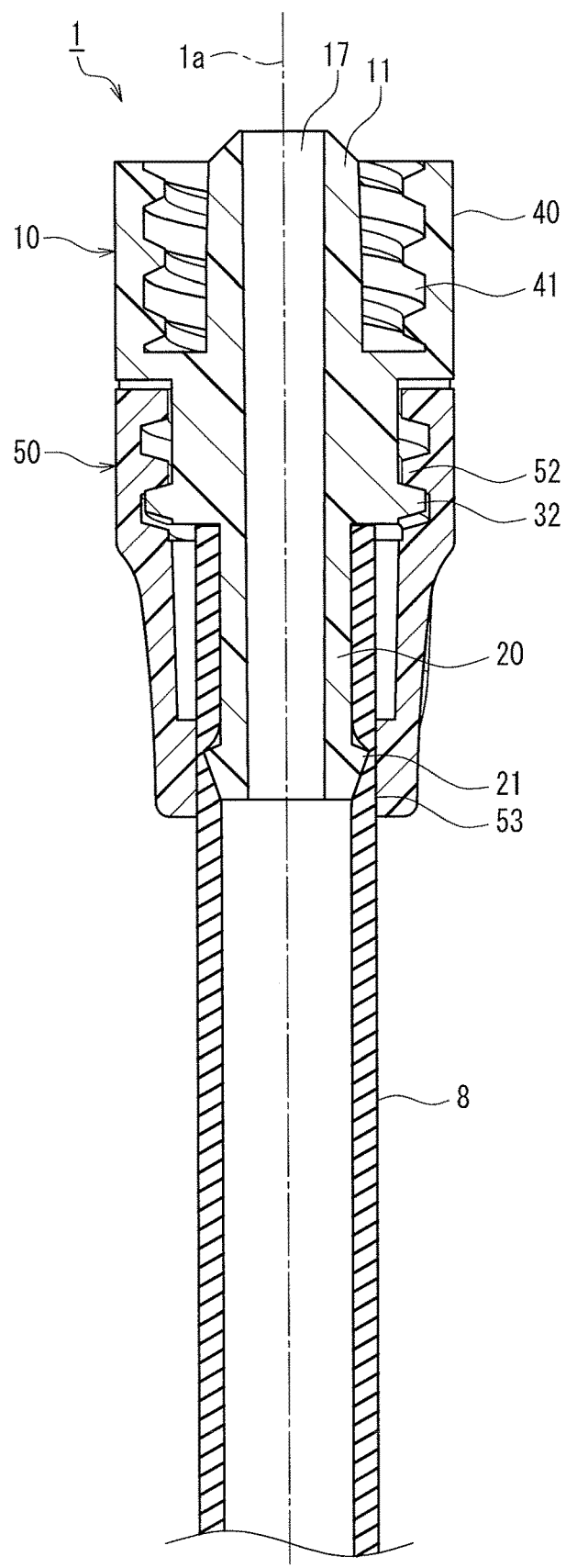
FIG. 1B is a cross-sectional view of the male connector according to Embodiment 1 of the present invention.

FIG. 1A is a perspective view of a male connector 1 according to Embodiment 1 of the present invention. FIG. 1B is a cross-sectional view taken along a plane that passes through a central axis 1a of the male connector 1. For the sake of convenience in the following description, the "up-down direction" refers to the direction parallel to the central axis 1a, the "upper side" of the male connector 1 refers to the upper side of the paper surface in FIGS. 1A and 1B, and the "lower side" of the male connector 1 refers to the lower side of the paper surface in FIGS. 1A and 1B. Also, the "circumferential direction" refers to the direction of rotation about the central axis 1a, the "radial direction" refers to the direction orthogonal to the central axis 1a, and the "horizontal direction" refers to the direction perpendicular to the central axis 1a. Note that "up-down direction", "upper side", "lower side", and "horizontal direction" do not mean orientations during actual use of the male connector 1.

The male connector 1 includes a connector body 10 and a lock nut 50.

Figure 2A:
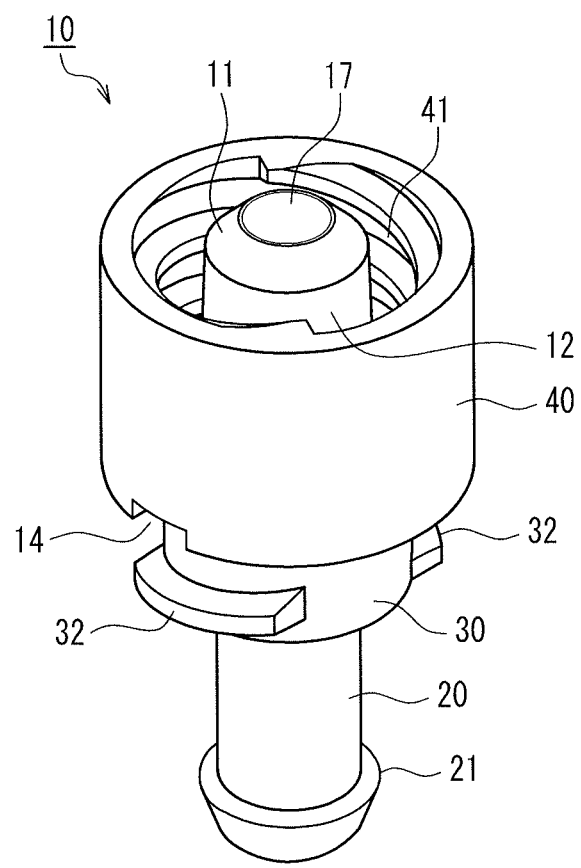
FIG. 2A is a perspective view of a connector body that constitutes the male connector according to Embodiment 1 of the present invention, as viewed from above.
Figure 2B:
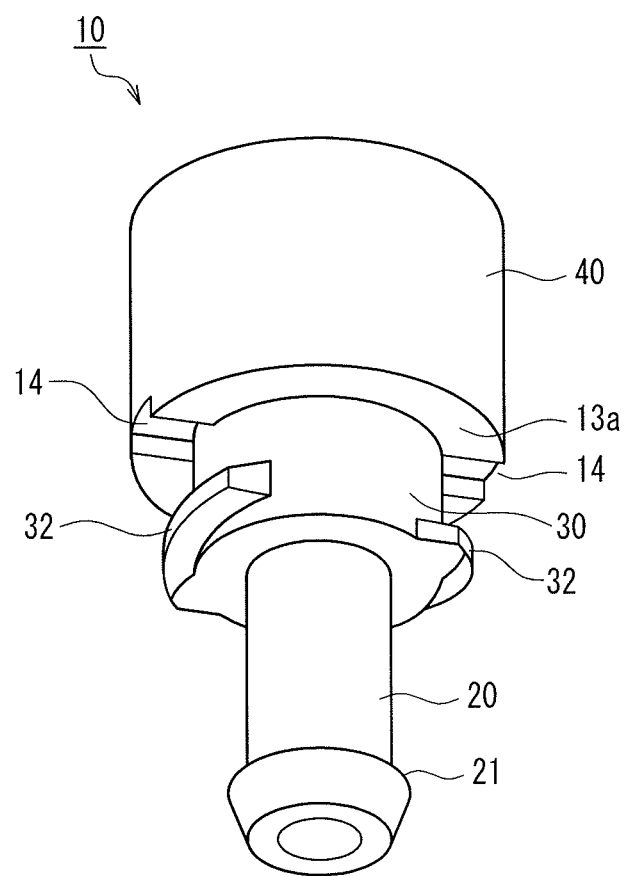
FIG. 2B is a perspective view of the connector body that constitutes the male connector according to Embodiment 1 of the present invention, as viewed from below.
Figure 2C:
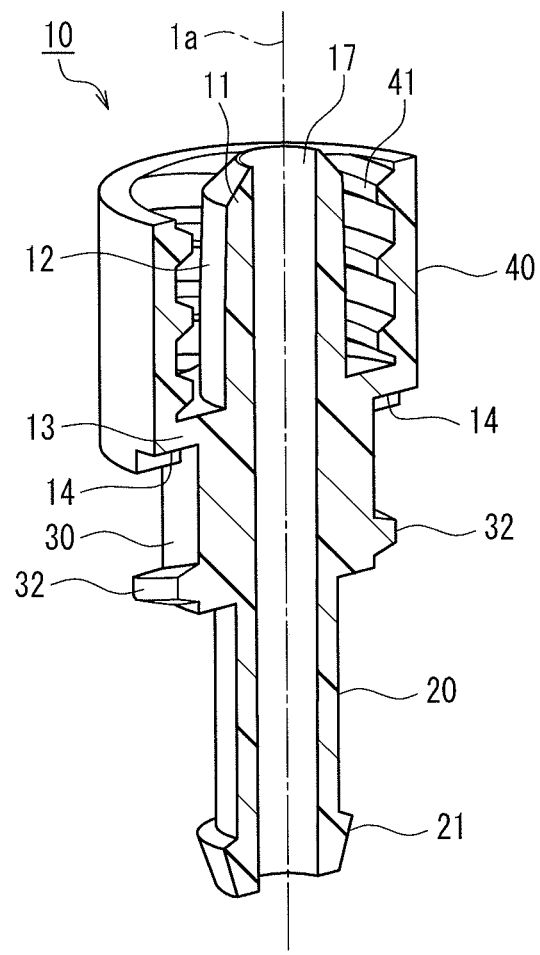
FIG. 2C is a perspective cross-sectional view of the connector body that constitutes the male connector according to Embodiment 1 of the present invention.

FIG. 2A is a perspective view of the connector body 10 as viewed from above, FIG. 2B is a perspective view of the connector body 10 as viewed from below, and FIG. 2C is a perspective cross-sectional view of the connector body 10 taken along a plane that includes the central axis 1a.

The connector body 10 includes a tubular male luer 11 at one end, and includes a tubular base end portion 20 at the other end. A channel 17 that extends along the central axis 1a passes through the connector body 10 from the male luer 11 to the base end portion 20.

Figure 24A:
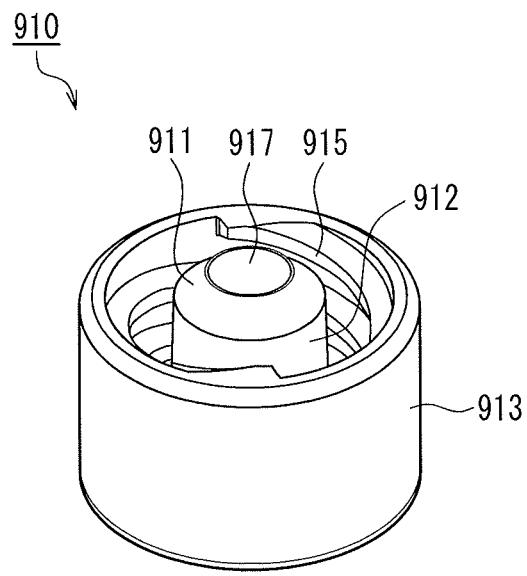
FIG. 24A is a perspective view of a male connector under consideration as ISO 80369-3.
Figure 24B:
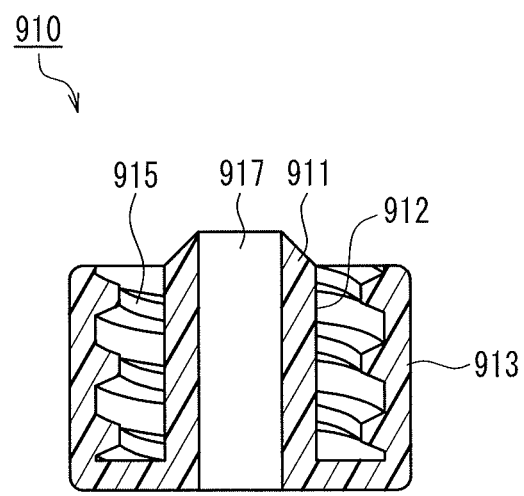
FIG. 24B is a cross-sectional view taken along a plane that includes the central axis of the male connector.
Figure 25A:
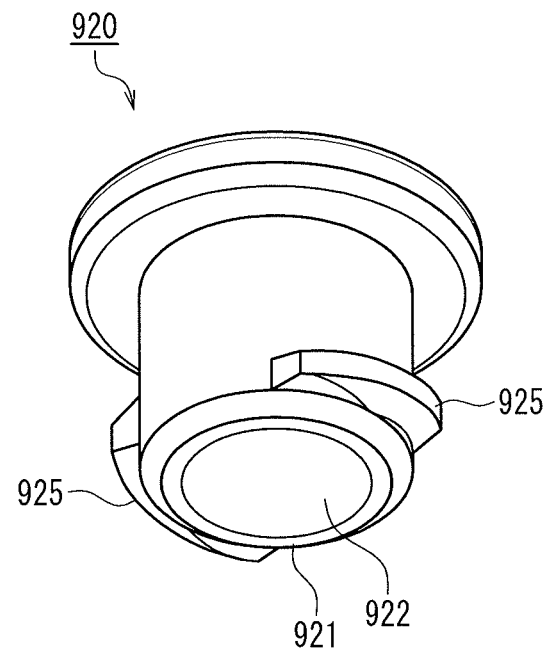
FIG. 25A is a perspective view of a female connector under consideration as ISO 80369-3.
Figure 25B:
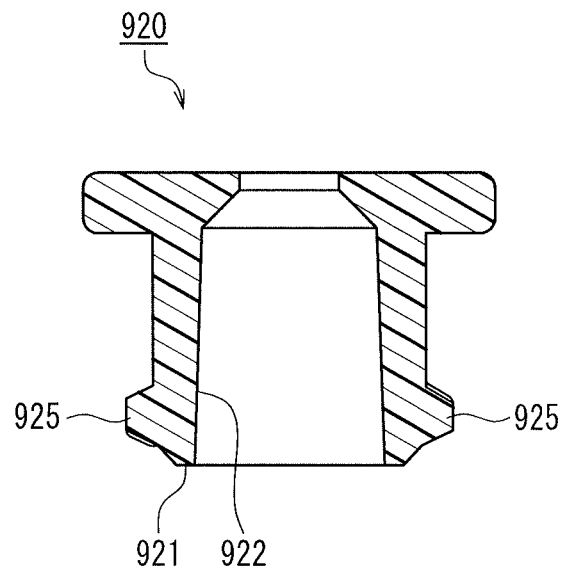
FIG. 25B is a cross-sectional view taken along a plane that includes the central axis of the female connector.

An outer circumferential face 12 of the male luer 11 is a tapered face (conical face) whose outer diameter decreases as it approaches the tip. A disc-shaped flange 13 protrudes outward along the radial direction from the base of the male luer 11. An outer tube 40 having a cylindrical shape is provided on the outer circumferential edge of the upper face of the flange 13 (the surface on the male luer 11 side). The outer tube 40 surrounds the male luer 11. Female threading (first female threading) 41 is formed in the inner circumferential face of the outer tube 40 (the face that opposes the male luer 11). The male luer 11 and the female threading 41 that surrounds the male luer 11 are compliant with the above-described male connector 910 of ISO 80369-3 (FIGS. 24A and 24B). Accordingly, the male connector 1 can be connected to the female connector 920 compliant with ISO 80369-3 (FIGS. 25A and 25B).

A lower face (face on the base end portion 20 side) 13a of the flange 13 is a flat face that is perpendicular to the central axis 1a. A pair of receding portions (first receding portions) 14 are formed in the lower face 13a of the flange 13. The pair of receding portions 14 are in rotation symmetry (two-fold symmetry) about the central axis 1a.

The outer circumferential face of the base end portion 20 is a cylindrical face whose outer diameter is constant in the central axis 1a direction. A fixed protrusion 21 that protrudes outward along the radial direction (in the direction of separation from the central axis 1a) is formed in the vicinity of the tip (lower end) of the base end portion 20. The fixed protrusion 21 is continuous in a ring shape along the circumferential direction of the base end portion 20. As shown in FIG. 2C, the cross-sectional shape of the fixed protrusion 21 along a plane that includes the central axis 1a is a wedge shape (or a triangular shape) having a sharp tip.

A tubular portion 30 is provided between the flange 13 and the base end portion 20. The outer circumferential face of the tubular portion 30 is a cylindrical face whose outer diameter is constant in the central axis 1a direction. The outer diameter of the tubular portion 30 is smaller than the outer diameter of the outer tube 40 and larger than the outer diameter of the base end portion 20. A spiral protrusion (first spiral protrusion) 32 protrudes outward from the outer circumferential face of the tubular portion 30. The spiral protrusion 32 is a so-called discontinuous thread, in which the thread ridge of the male threading is divided so as to be discontinuous in the circumferential direction.

Figure 3A:
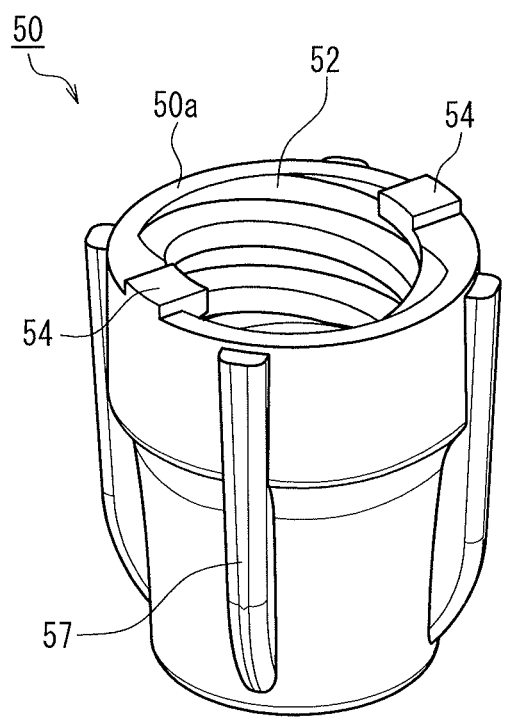
FIG. 3A is a perspective view of a lock nut that constitutes the male connector according to Embodiment 1 of the present invention, as viewed from above.
Figure 3B:
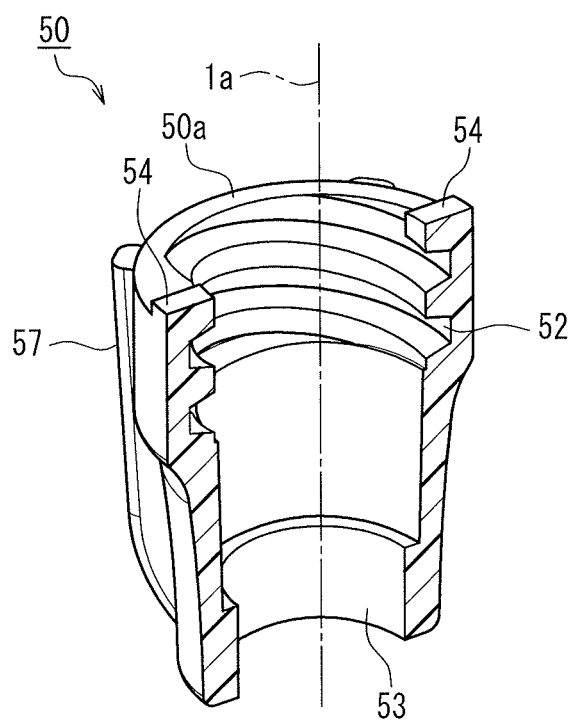
FIG. 3B is a perspective cross-sectional view of the lock nut that constitutes the male connector according to Embodiment 1 of the present invention.

FIG. 3A is a perspective view of the lock nut 50 as viewed from above, and FIG. 3B is a perspective cross-sectional view of the lock nut 50 taken along a plane that includes the central axis 1a.

The lock nut 50 has a hollow, approximately cylindrical shape, and is open at the two ends in the up-down direction. Female threading (second female threading) 52 is provided on the upper side of the inner circumferential face of the lock nut 50, and a small diameter portion 53 is provided on the lower side. The female threading 52 is configured to be capable of being screwed together with the spiral protrusion 32 (FIGS. 2A to 2C) of the connector body 10. The spiral direction of the female threading 52 is the same as the spiral direction of the female threading 41 (FIGS. 2A and 2C) of the connector body 10. In Embodiment 1, the female threading 41 and the female threading 52 are both right-handed threading.

The inner diameter of the small diameter portion 53 is smaller than the inner diameters of any of the portions of the lock nut 50 located above the portion 53, and is slightly larger than the maximum outer diameter of the fixed protrusion 21 (FIGS. 2A to 2C) of the connector body 10. The inner circumferential face of the small diameter portion 53 is a cylindrical face whose inner diameter is constant in the central axis 1*a* direction. It should be noted that the present invention is not limited in this way, and the inner circumferential face may be a tapered face whose inner diameter decreases as it extends downward.

A pair of protruding portions (first protruding portions) 54 protrude upward from an upper end face (i.e., upper face) 50*a* of the lock nut 50. The pair of protruding portions 54 are in rotation symmetry (two-fold symmetry) about the central axis 1*a*. Ribs (protrusions) 57, which extend in the up-down direction, protrude outward from the outer circumferential face of the lock nut 50 such that rotation torque is easily applied to the lock nut 50. In the present embodiment, four ribs 57 are provided, but the number of ribs 57 is arbitrary. It is also possible to omit the ribs 57.

The connector body 10 and the lock nut 50 are made of a material that is hard (a hard material) and has a mechanical strength (rigidity) to the extent of substantially not deforming under external force. Examples of resin materials that can be used as this hard material include polypropylene (PP), polycarbonate (PC), polyacetal (POM), polystyrene, polyamide, polyethylene, rigid polyvinyl chloride, and acrylonitrile butadiene styrene copolymer (ABS), but there are no limitations on the resin material. Among these materials, polypropylene (PP), polycarbonate (PC), polyacetal (POM), and acrylonitrile butadiene styrene copolymer (ABS) are preferable. The connector body 10 and the lock nut 50 can each be formed in an integrated manner using injection molding or the like and the aforementioned resin materials. The materials constituting the connector body 10 and the lock nut 50 may be the same or different from each other.

Attachment to and Detachment from Tube

The male connector 1, which has the above-described configuration and is constituted by the connector body 10 and the lock nut 50, is removably attached to the upstream end of a tube 8 (FIGS. 1A and 1B).

A bendable hollow tube can be used as the tube 8. It is preferable that the tube 8 has a property of easily deforming under external force, and immediately returning to a default state when the external force disappears (so-called rubber-like elasticity). Although there are no limitations on the material of the tube 8, it is possible to use a soft material that has rubber-like elasticity (a so-called elastomer). For example, it is possible to use a rubber such as natural rubber, isoprene rubber, or silicone rubber; a thermoplastic elastomer such as styrene elastomer, olefin elastomer, or polyurethane elastomer; or soft polyvinyl chloride. Among these materials, silicone rubber is preferable. The tube 8 may be a catheter that is indwelled in the patient with the downstream end inserted into the patient (e.g., a transnasal catheter or a PEG catheter), or may be a tube that is connected to the upstream end of such a catheter.

The male connector 1 is attached to the tube 8 as follows.

Figure 4A:
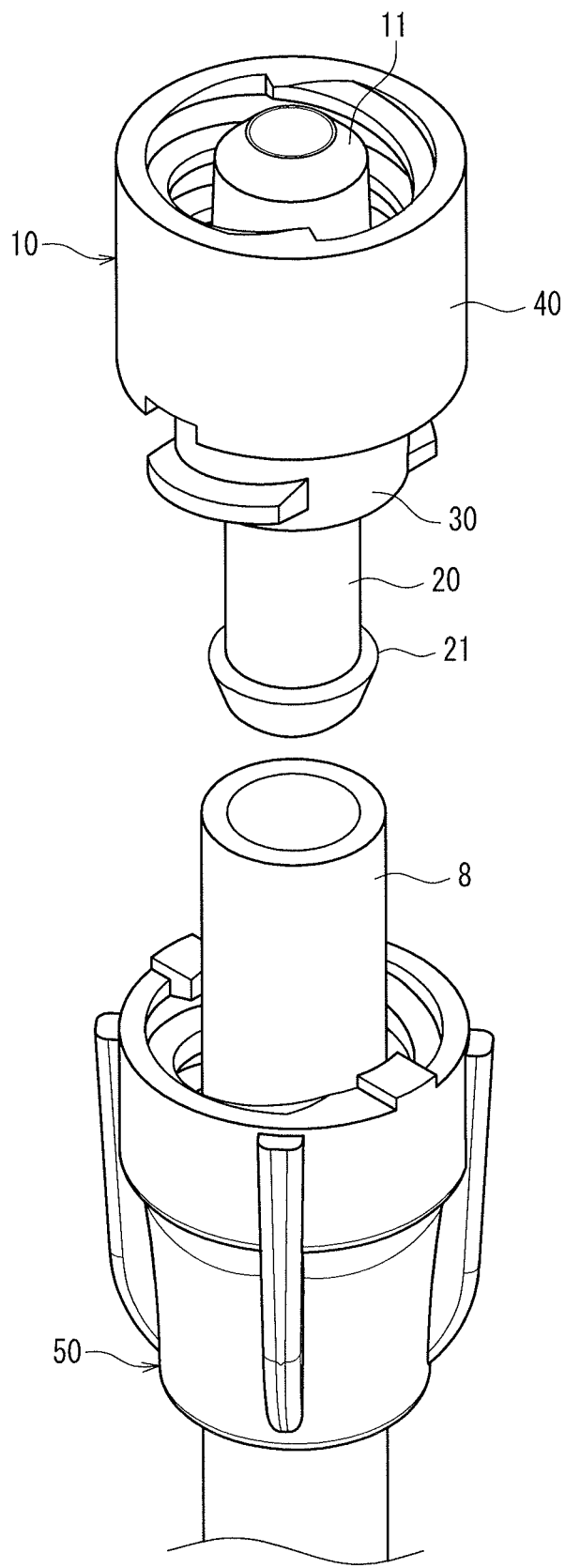
FIG. 4A is a perspective diagram showing one step for attaching the male connector according to Embodiment 1 of the present invention to a tube.

First, as shown in FIG. 4A the tube 8 is inserted into the lock nut 50. The connector body 10 is then arranged so as to oppose the upstream end of the tube 8.

Figure 4B:
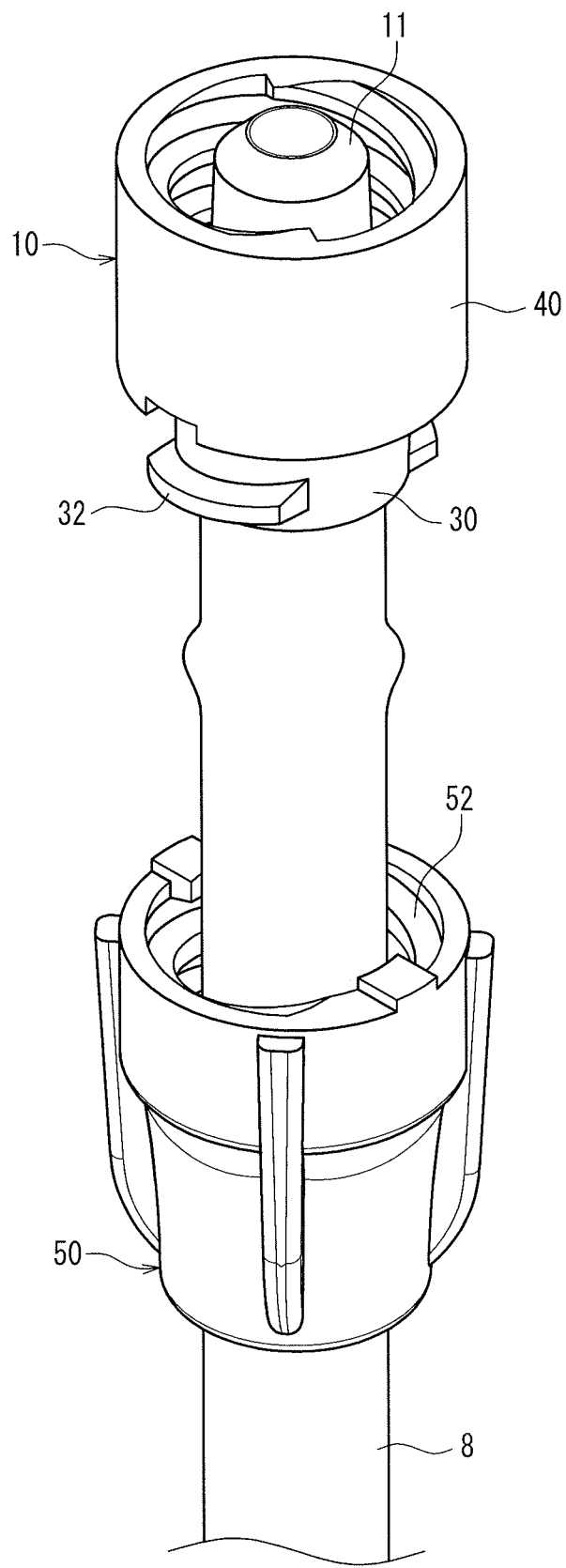
FIG. 4B is a perspective diagram showing one step for attaching the male connector according to Embodiment 1 of the present invention to a tube.

Next, as shown in FIG. 4B, the base end portion 20 of the connector body 10 is inserted into the tube 8. The maximum outer diameter of the fixed protrusion 21 (see FIGS. 2A and 2B) provided on the outer circumferential face of the base end portion 20 is preferably set slightly larger than the inner diameter of the tube 8. Accordingly, the tube 8 is widened by the fixed protrusion 21 at the position corresponding to the fixed protrusion 21. It is preferable that approximately the entirety of the base end portion 20 is inserted in the tube 8 so that the upstream end of the tube 8 comes into contact with the tubular portion 30 of the connector body 10.

Figure 4C:
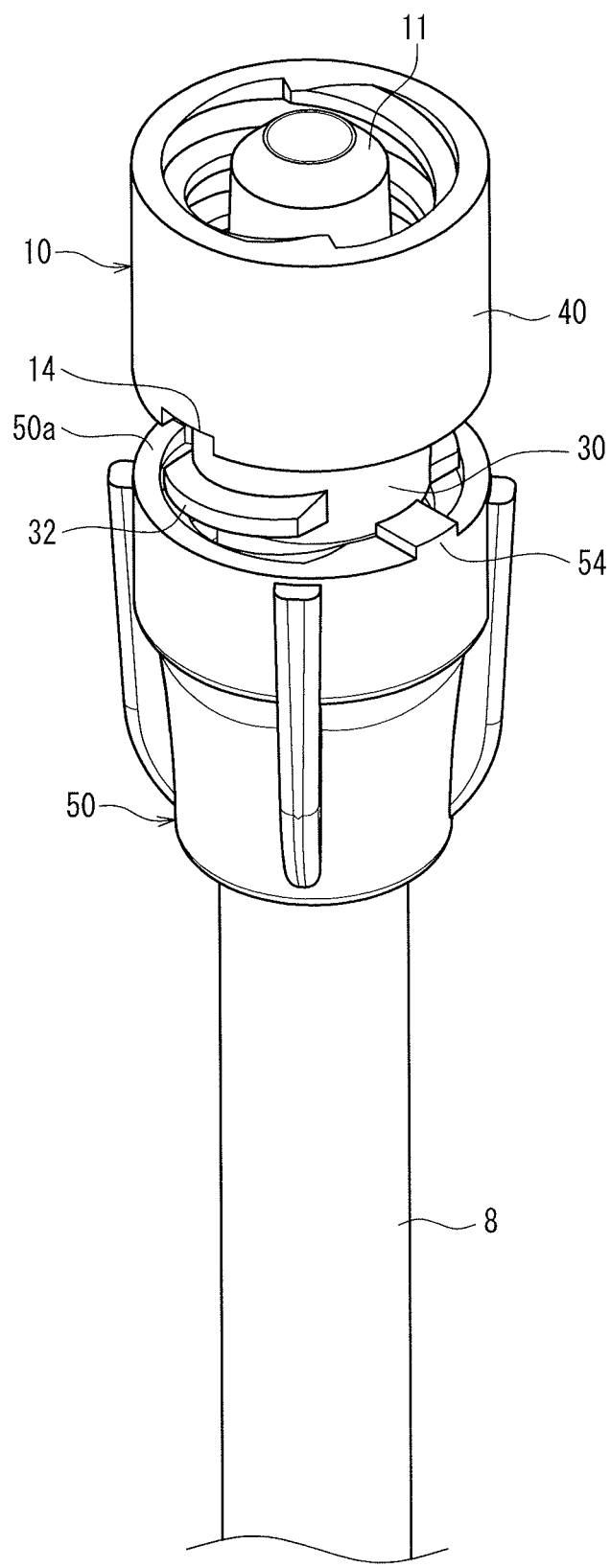
FIG. 4C is a perspective diagram showing one step for attaching the male connector according to Embodiment 1 of the present invention to a tube.

Next, as shown in FIG. 4C, the lock nut 50 is moved toward the connector body 10. The thread ridge of the female threading 52 of the lock nut 50 collides with the spiral protrusion 32 of the connector body 10. The lock nut 50 is rotated relative to the connector body 10, thus screwing the spiral protrusion 32 and the female threading 52 together. As the lock nut 50 is rotated, the tubular portion 30 advances inside the lock nut 50. The pair of protruding portions 54 of the lock nut 50 soon come into contact with the lower face 13*a* (see FIG. 2B) of the flange 13 of the connector body 10, and slide thereon. Finally, the pair of protruding portions 54 are fitted into the pair of receding portions 14 of the connector body 10, and, at the same time, the upper face 50*a* of the lock nut 50 and the lower face 13*a* of the flange 13 come into contact or approach each other. When the pair of protruding portions 54 are fitted into the pair of receding portions 14, the rotation torque for rotating the lock nut 50 changes, and the operator can feel that change as a clicking sensation through their fingers.

Thus, the male connector 1 is attached to the upstream end of the tube 8 as shown in FIGS. 1A and 1B. As shown in FIG. 1A, the protruding portions 54 of the lock nut 50 are fitted into the receding portions 14 of the connector body 10. As shown in FIG. 1B, the fixed protrusion 21 and the small diameter portion 53 oppose each other and clamp the tube 8 while compressing it in the radial direction. The spiral protrusion 32 of the connector body 10 is screwed together with the female threading 52 of the lock nut 50. The channel 17 that passes through the connector body 10 is in communication with the tube 8.

The male connector 1 that is attached to the tube 8 as shown in FIGS. 1A and 1B is removed from the tube 8 as follows.

First, the lock nut 50 is rotated relative to the connector body 10, in the direction opposite to that during attachment. In order to begin rotation, the protruding portions 54 and the receding portions 14 need to be disengaged, and a somewhat large amount of rotation torque needs to be applied for disengagement. After the protruding portions 54 have escaped the receding portions 14, the lock nut 50 can be rotated relative to the connector body 10 with a small rotation torque.

After the lock nut 50 has been separated from the connector body 10 as shown in FIG. 4B, the connector body 10 is pulled out from the tube 8 (FIG. 4A). Thereafter, the tube 8 is pulled out from the lock nut 50.

The male connector 1 can be repeatedly attached to and detached from the tube 8 any number of times. When the lock nut 50 is rotated, rotation torque is easily applied by catching the ribs 57 with one's fingers.

Method of Use

The following describes a method of using the male connector 1 in the case where the male connector 1 is attached to the upstream end of a PEG catheter. In this case, the tube 8 is a PEG catheter, and the lower end thereof (not shown) in FIGS. 1A and 1B is inserted into the patient's stomach. The male connector 1 is indwelled in the patient along with the tube 8 (PEG catheter) in the state of being fixed to the upstream end of the tube 8 as shown in FIGS. 1A and 1B.

In the case of performing enteral feeding, the female connector connected to the downstream end of a tube (container-side tube) connected to the container storing an enteral nutrient is connected to the male connector 1. The female connector is the female connector 920 compliant with ISO 80369-3 (FIGS. 25A and 25B). The male connector 1 and the female connector 920 can be connected by inserting the male luer 11 into the insertion portion 921 and screwing the female threading 41 and the male threading 926 together. At this time, rotation torque can be easily applied to the male connector 1 by catching the ribs 57 of the lock nut 50 with one's fingers. The protruding portions 54 of the lock nut 50 are fitted into the receding portions 14 of the connector body 10, the upper face 50a of the lock nut 50 is in contact with the lower face 13a of the flange 13 of the connector body 10, and the fixed protrusion 21 and the small diameter portion 53 clamp the tube 8. Accordingly, when the lock nut 50 is rotated relative to the female connector 920, the connector body 10 rotates integrally with the lock nut 50.

The outer circumferential face 12 of the male luer 11 is a tapered face that has the same taper angle as the inner circumferential face 922 of the insertion portion 921. Accordingly, they come into liquid-tight surface contact with each other. The connection between the male connector 1 and the female connector 920 is excellent in terms of liquid-tightness and connection strength, similarly to the connection between the male connector 910 (FIGS. 24A and 24B) and the female connector 920. When the male connector 1 and the female connector 920 are in the connected state, an enteral nutrient is administered to the patient via the channel 17 and the tube 8.

Thereafter, the male connector 1 and the female connector 920 are separated. Separation can be performed by rotating the female connector 920 relative to the male connector 1 in the direction opposite to that during attachment so as to unscrew the female threading 41 and the male threading 926. At this time as well, rotation torque in the direction opposite to that during connection can be applied to the lock nut 50 by catching the ribs 57 of the lock nut 50 with one's fingers. The protruding portions 54 of the lock nut 50 are fitted into the receding portions 14 of the connector body 10, and the fixed protrusion 21 and the small diameter portion 53 clamp the tube 8. Accordingly, when the lock nut 50 is rotated relative to the female connector 920, the connector body 10 rotates integrally with the lock nut 50. According to this configuration, the screwing together of the female threading 41 and the male threading 926 is selectively loosened, without loosening the screwing together of the spiral protrusion 32 and the female threading 52.

There are cases where an enteral nutrient has become stuck on the male connector 1 after the female connector 920 has been separated. In this case, the male connector 1 can be further separated from the tube 8 in order to clean the male connector 1. The detached and disassembled connector body 10 and lock nut 50 can each be cleaned by washing with water or the like. The cleaned connector body 10 and lock nut 50 are then attached to the tube 8 again. If the connector body 10 and/or the lock nut 50 are very dirty, they can be replaced with new ones instead of being cleaned.

Although this will not be described in detail, in the case of installing a gastrostomy, the tube (PEG catheter) 8 without the male connector 1 attached thereto is inserted into the patient's stomach through their mouth, and then the tip (upstream end) is pulled out of the patient's body through their abdomen. After the tube 8 has been fixed to the patient, the male connector 1 is attached to the tip.

Effects

As described above, the male connector 1 of Embodiment 1 includes the male luer 11 and the female threading (first female threading) 41 that surrounds the male luer 11. Accordingly, the male connector 1 can be connected to the female connector 920 that is compliant with ISO 80369-3 and includes the insertion portion 921 for receiving insertion of the male luer 11 and the male threading 926 that is to be screwed together with the female threading 41.

The male connector 1 is made up of two parts, namely the connector body 10 and the lock nut 50. After the base end portion 20 of the connector body 10 has been inserted into the tube 8, when the spiral protrusion 32 of the connector body 10 and the female threading (second female threading) 52 of the lock nut 50 are screwed together, the fixed protrusion 21 of the connector body 10 and the small diameter portion 53 of the lock nut 50 clamp the tube 8 in the radial direction. The tube 8 is locally compressed by the tip of the fixed protrusion 21, which has a wedge-shaped cross-sectional shape, and the inner circumferential face of the small diameter portion 53. Accordingly, the male connector 1 can be firmly attached to the tube 8. An enteral nutrient does not leak from the joining portion of the male connector 1 and the tube 8 due to pressure applied to the enteral nutrient flowing through the channel 17 and the tube 8, and the male connector 1 and the tube 8 do not unintentionally become separated due to tensile force acting on the tube 8.

When the spiral protrusion 32 and the female threading 52 are unscrewed, the small diameter portion 53 moves downstream along the lengthwise direction of the tube 8 relative to the fixed protrusion 21, and the clamping of the tube 8 by the fixed protrusion 21 and the small diameter portion 53 is released. Accordingly, the male connector 1 can be removed from the tube 8.

For this reason, while keeping the tube 8 indwelled in the patient, it is possible to remove the male connector 1 from the tube 8 and clean the connector body 10 and the lock nut 50 that constitute the male connector 1. If impurities are firmly stuck to the connector body 10 and/or the lock nut 50, it is also possible to replace them with new ones. Accordingly, the male connector 1 of Embodiment 1 includes the male luer 11 and the female threading 41 that surrounds the male luer 11, and can be easily maintained in a sanitary state.

Also, in the case of installing a gastrostomy, the tube 8 without the male connector 1 attached thereto can be fixed to the patient, and then the male connector 1 can be attached to the tip of the tube 8. Accordingly, the operation of adding a gastrostomy is easy.

The clamping of the tube 8 by the fixed protrusion 21 and the small diameter portion 53 and the releasing thereof are performed using screwing structures constituted by the spiral protrusion 32 and the female threading (second female threading) 52. The screwing structures convert rotation of the lock nut 50 relative to the connector body 10 into movement of the lock nut 50 along the central axis 1a. Accordingly, the operations of clamping the tube 8 by the fixed protrusion 21 and the small diameter portion 53 and releasing it can be performed with a relatively small amount of force.

The pair of receding portions 14 of the connector body 10 and the pair of protruding portions 54 of the lock nut 50 are fitted together. By engaging with each other (fitting together), the receding portions 14 and the protruding portions 54 constitute first rotation prevention mechanisms for preventing the lock nut 50 from rotating relative to the connector body 10. By engaging in the circumferential direction, the protruding portions 54 and the receding portions 14 that constitute the first rotation prevention mechanisms prevent relative rotation between the connector body 10 and the lock nut 50. Accordingly, it is possible to prevent the screwing together of the spiral protrusion 32 and the second female threading 52 from becoming loosened unintentionally. It is possible to release the locked state of the first rotation prevention mechanisms (i.e., the engaged state of the receding portions 14 and the protruding portions 54) and rotate the lock nut 50 relative to the connector body 10, but a relatively large amount of force is necessary. For this reason, when the lock nut 50 and the female connector 920 are respectively gripped and rotated in mutually opposite directions in order to separate the male connector 1 and the female connector 920 that are connected to each other, the first rotation prevention mechanisms cause the connector body 10 to rotate integrally with the lock nut 50, and therefore the screwing together of the female threading 41 and the male threading 926 is selectively loosened, without the screwing together of the spiral protrusion 32 and the female threading 52 being loosened. Accordingly, the male connector 1 and the female connector 920 can be separated without the male connector 1 becoming disassembled. The amount of force (rotation torque) necessary for putting the first rotation prevention mechanisms into the locked state and releasing the locked state can be adjusted by appropriately changing the dimensions, shape, and the like of the protruding portions 54 and the receding portions 14. For example, the aforementioned force (rotation torque) can be reduced by, for example, reducing the protruding height of the protruding portions 54 from the upper face 50a of the lock nut 50, rounding or chamfering the tips of the protruding portions 54, or chamfering the edges of the openings of the receding portions 14.

The first rotation prevention mechanisms also are useful in firmly screwing the female threading 41 and the male threading 926 together by respectively gripping the lock nut 50 and the female connector 920 when connecting the female connector 920 to the male connector 1.

Although the male connector 1 is constituted by two parts, namely the connector body 10 and the lock nut 50, it includes the first rotation prevention mechanisms, and therefore the operability of connection to and separation from the female connector 920 is equivalent to the operability when the male connector 910 constituted by one part is connected to and separated from the female connector 920.

Note that in addition to the first rotation prevention mechanisms described above, frictional force between the fixed protrusion 21 and the small diameter portion 53 applied via the tube 8 also contributes to preventing rotation of the lock nut 50 relative to the connector body 10.

Embodiment 2

Configuration

A male connector 2 of Embodiment 2 is different from the male connector 1 of Embodiment 1 with respect to the configuration of the first rotation prevention mechanisms that prevent the lock nut from rotating relative to the connector body. The male connector 2 of Embodiment 2 will be described with focus on differences from the male connector 1 of Embodiment 1. In the drawings referenced below, elements the same as or corresponding to elements of the male connector 1 of Embodiment 1 are denoted by the same reference signs, and detailed descriptions will not be given for them.

Figure 5A:
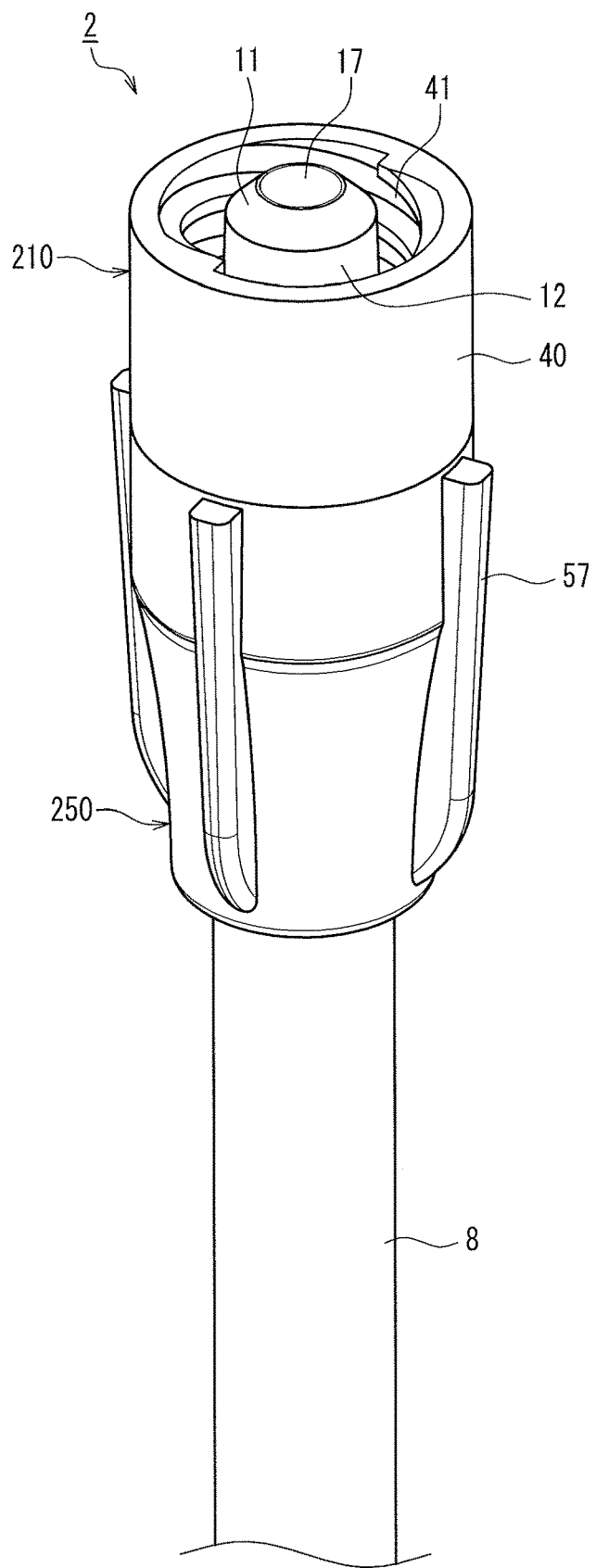
FIG. 5A is a perspective view of a male connector according to Embodiment 2 of the present invention.
Figure 5B:
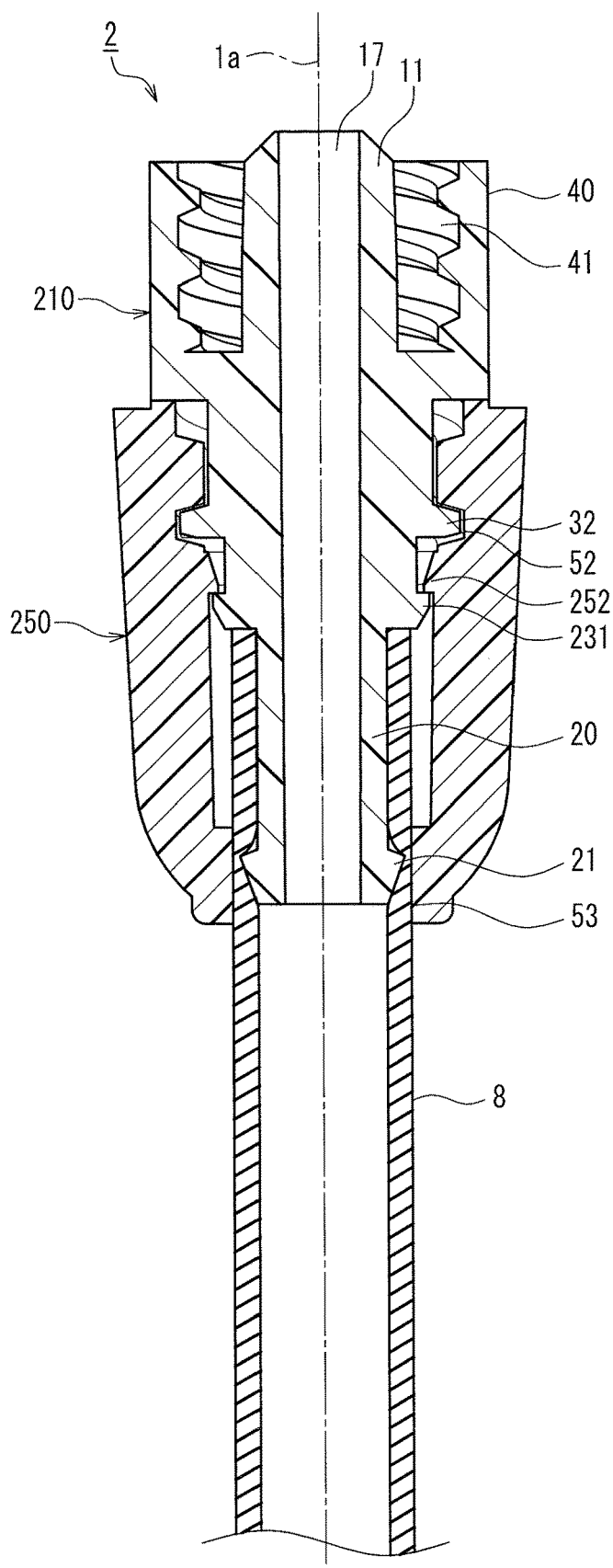
FIG. 5B is a cross-sectional view of the male connector according to Embodiment 2 of the present invention.

FIG. 5A is a perspective view of the male connector 2 according to Embodiment 2 of the present invention. FIG. 5B is a cross-sectional view taken along a plane that passes through the central axis 1a of the male connector 2. Similarly to the male connector 1 of Embodiment 1, the male connector 2 of Embodiment 2 includes a connector body 210 and a lock nut 250.

Figure 6A:
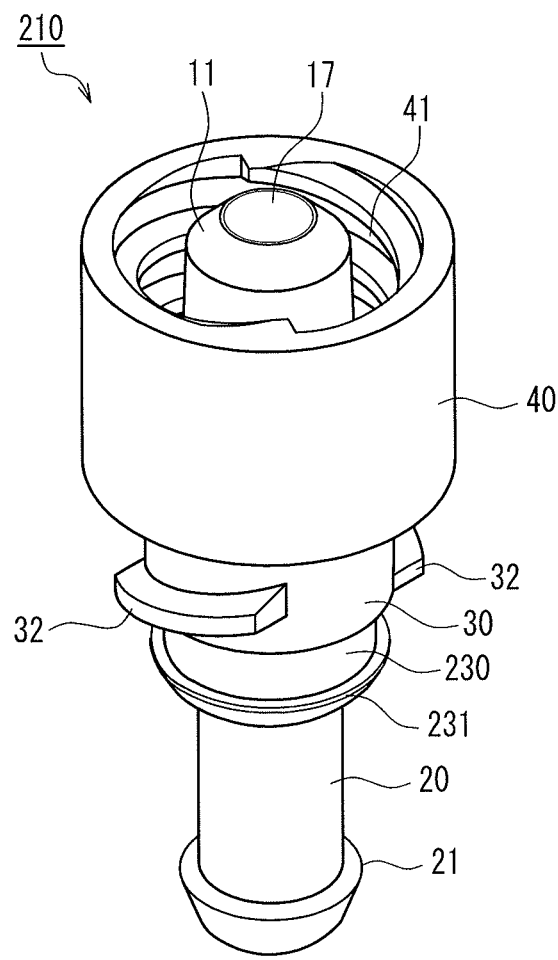
FIG. 6A is a perspective view of a connector body that constitutes the male connector according to Embodiment 2 of the present invention, as viewed from above.
Figure 6B:
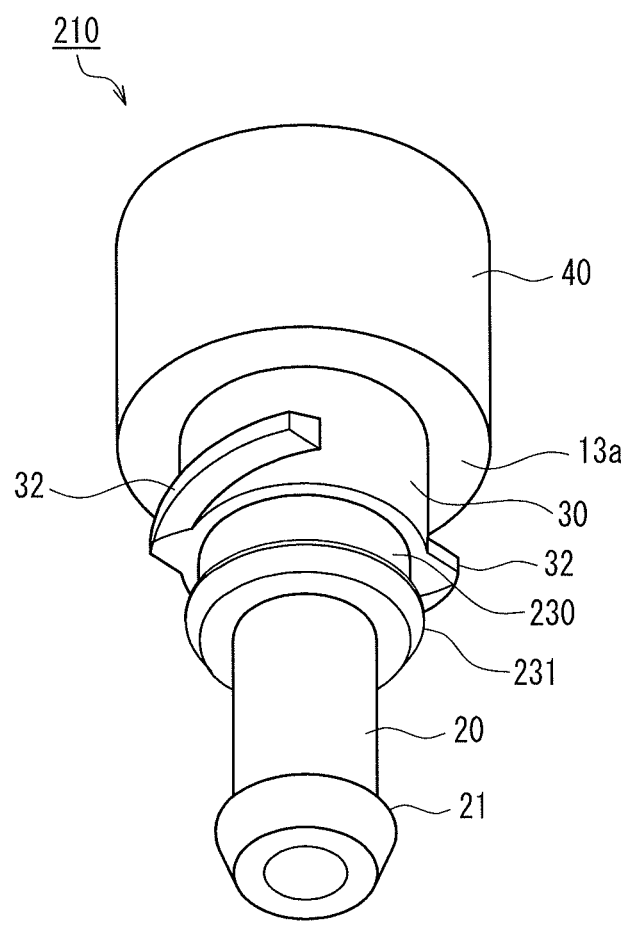
FIG. 6B is a perspective view of the connector body that constitutes the male connector according to Embodiment 2 of the present invention, as viewed from below.
Figure 6C:
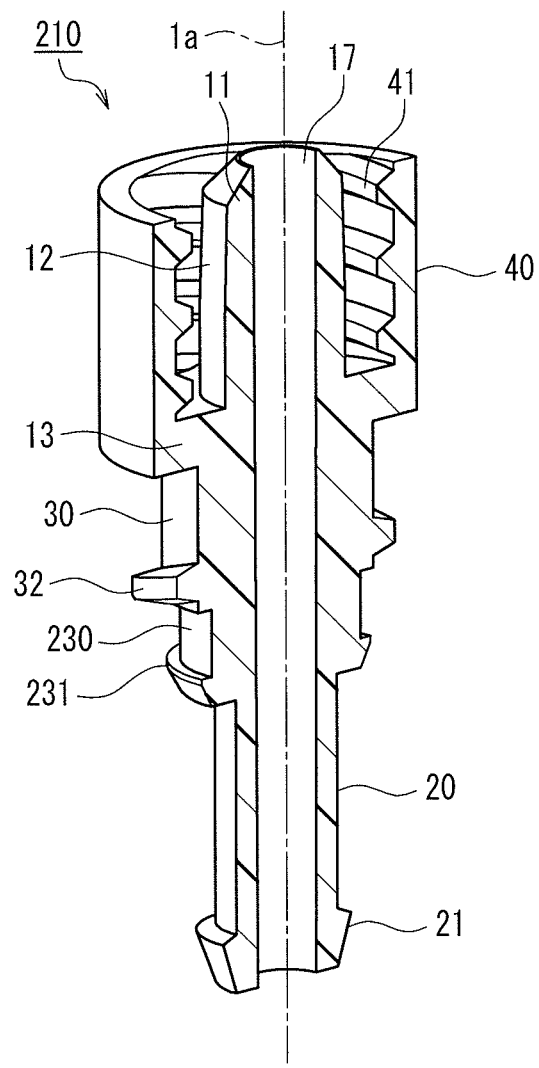
FIG. 6C is a perspective cross-sectional view of the connector body that constitutes the male connector according to Embodiment 2 of the present invention.

FIG. 6A is a perspective view of the connector body 210 as viewed from above, FIG. 6B is a perspective view of the connector body 210 as viewed from below, and FIG. 6C is a perspective cross-sectional view of the connector body 210 taken along a plane that includes the central axis 1a.

As shown most clearly in FIG. 6B, the pair of receding portions 14 (FIG. 2B) formed in the connector body 10 of Embodiment 1 are not formed in the lower face 13a of the flange 13.

In Embodiment 2, a first engaging protrusion 231 that is continuous in the circumferential direction protrudes outward between the tubular portion 30 and the base end portion 20. As shown in FIG. 6C, the upper face of the first engaging protrusion 231 is a flat face that is perpendicular to the central axis 1a. The outer circumferential edge of this flat face is the apex portion (portion with the maximum outer diameter) of the first engaging protrusion 231. The face below the apex portion is a tapered face (conical face) whose outer diameter decreases as it moves downward from the apex portion.

A second tubular portion 230 is formed between the tubular portion 30 and the first engaging protrusion 231. The outer circumferential face of the second tubular portion 230 is a cylindrical face whose outer diameter is constant in the central axis 1a direction. The outer diameter of the second tubular portion 230 is smaller than the outer diameter of the tubular portion (first tubular portion) 30. The first engaging protrusion 231 is formed on the lower end of the second tubular portion 230.

Figure 7A:
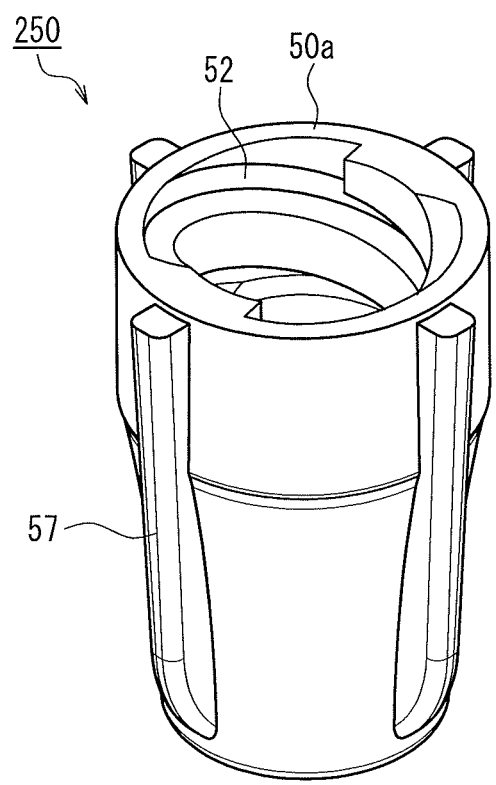
FIG. 7A is a perspective view of a lock nut that constitutes the male connector according to Embodiment 2 of the present invention, as viewed from above.
Figure 7B:
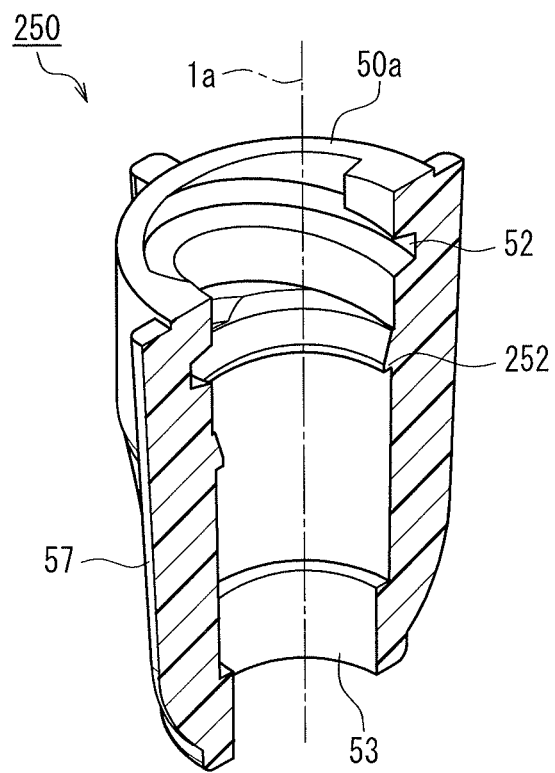
FIG. 7B is a perspective cross-sectional view of the lock nut that constitutes the male connector according to Embodiment 2 of the present invention.

FIG. 7A is a perspective view of the lock nut 250 as viewed from above, and FIG. 7B is a perspective cross-sectional view of the lock nut 250 taken along a plane that includes the central axis 1a.

As shown in FIG. 7A, the pair of protruding portions 54 (FIG. 3A) formed on the lock nut 50 of Embodiment 1 are not formed on the upper face 50a of the lock nut 250. As shown in FIG. 7B, a second engaging protrusion 252 that is continuous in the circumferential direction protrudes toward the central axis 1a from the inner circumferential face of the lock nut 250, at a position between the female threading 52 and the small diameter portion 53. The lower face of the second engaging protrusion 252 is a flat face that is perpendicular to the central axis 1a. The inner circumferential edge of this flat face is the apex portion (portion with the minimum inner diameter) of the second engaging protrusion 252. The face above the apex portion is a tapered face (conical face) whose inner diameter increases as it moves upward from the apex portion.

The configuration of the male connector 2 is the same as the male connector 1 of Embodiment 1 with the exception of the content described above.

Attachment to and Detachment from Tube

The male connector 2, which has the above-described configuration and is constituted by the connector body 210 and the lock nut 250, is removably attached to the upstream end of the tube 8 (FIGS. 5A and 5B).

The male connector 2 is attached to the tube 8 as follows.

Figure 8A:
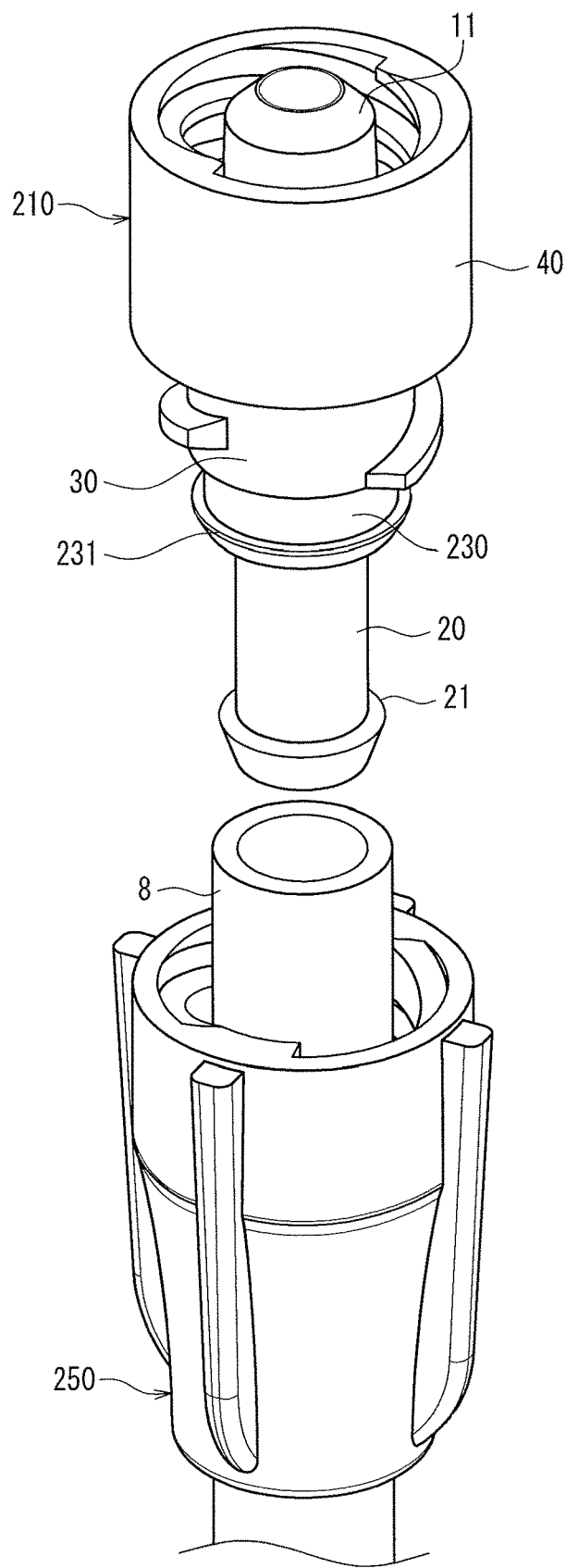
FIG. 8A is a perspective diagram showing one step for attaching the male connector according to Embodiment 2 of the present invention to a tube.

First, as shown in FIG. 8A, the tube 8 is inserted into the lock nut 250. The connector body 210 is then arranged so as to oppose the upstream end of the tube 8.

Figure 8B:
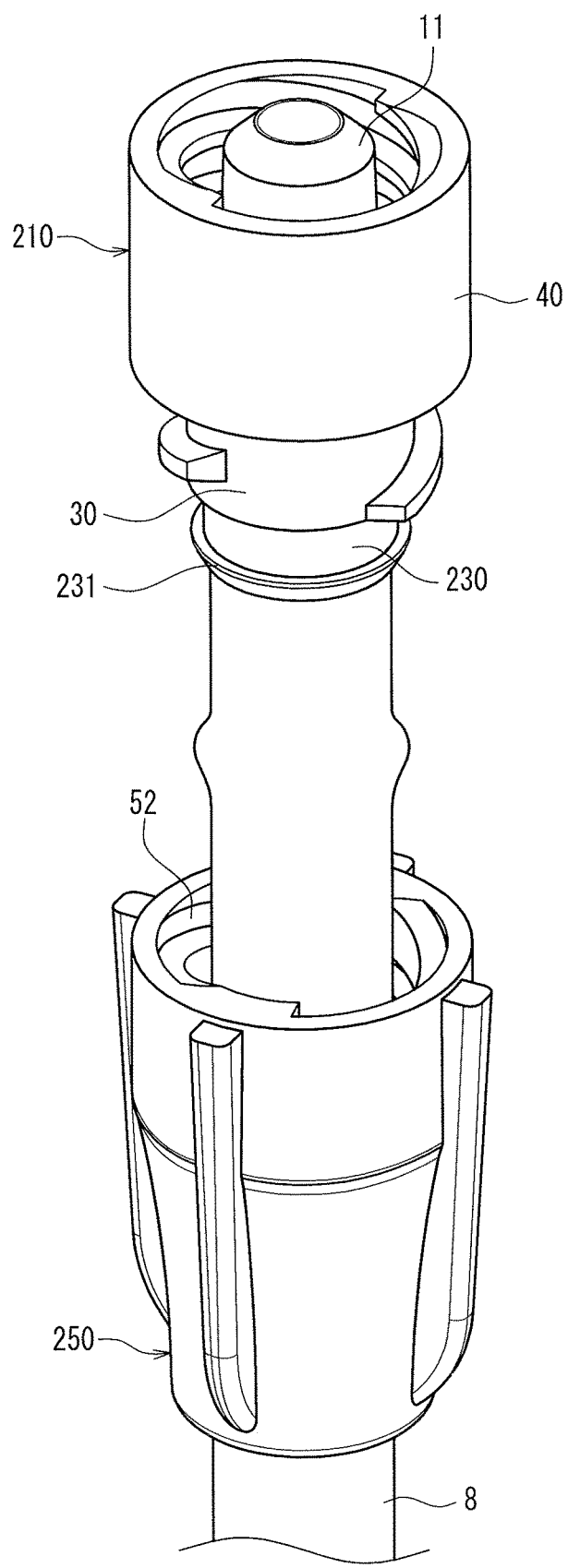
FIG. 8B is a perspective diagram showing one step for attaching the male connector according to Embodiment 2 of the present invention to a tube.

Next, as shown in FIG. 8B, the base end portion 20 of the connector body 210 is inserted into the tube 8. Similarly to Embodiment 1, the tube 8 is widened by the fixed protrusion 21 at the position corresponding to the fixed protrusion 21.

Figure 8C:
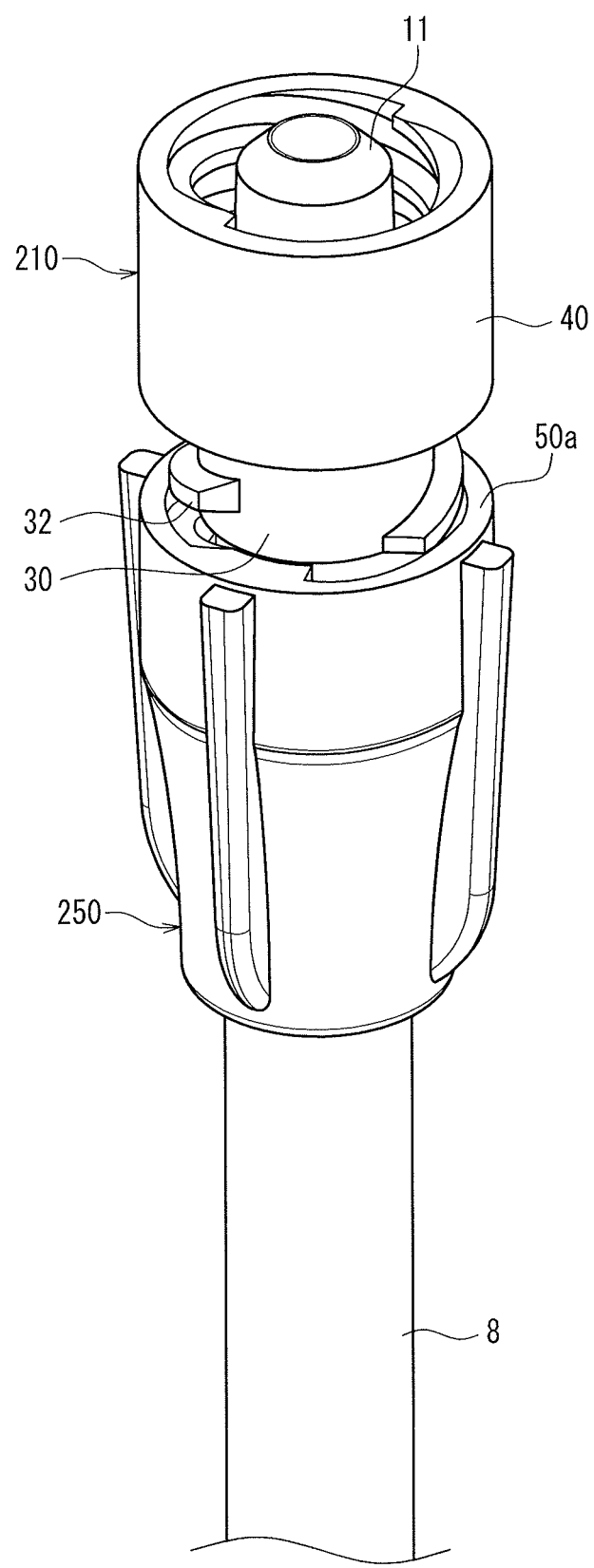
FIG. 8C is a perspective diagram showing one step for attaching the male connector according to Embodiment 2 of the present invention to a tube.

Next, as shown in FIG. 8C, the lock nut 250 is moved toward the connector body 210. The lock nut 250 is rotated relative to the connector body 210, thus screwing the spiral protrusion 32 and the female threading 52 together. As the lock nut 250 is rotated, the tubular portion 30 advances inside the lock nut 250. The second engaging protrusion 252 (FIG. 7B) of the lock nut 250 soon collides with the first engaging protrusion 231 (FIGS. 6A to 6C) of the connector body 210, and rides over the first engaging protrusion 231. At the same time as this, the upper face 50a of the lock nut 250 and the lower face 13a of the flange 13 come into contact or approach each other. When the second engaging protrusion 252 rides over the first engaging protrusion 231, the rotation torque for rotating the lock nut 250 changes, and the operator can feel that change as a clicking sensation through their fingers.

Thus, the male connector 2 is attached to the upstream end of the tube 8 as shown in FIGS. 5A and 5B. As shown in FIG. 5B, the first engaging protrusion 231 and the second engaging protrusion 252 are engaged with each other. The fixed protrusion 21 and the small diameter portion 53 oppose each other and clamp the tube 8 while compressing it in the radial direction. The spiral protrusion 32 of the connector body 210 is screwed together with the female threading 52 of the lock nut 250. The channel 17 that passes through the connector body 210 is in communication with the tube 8.

The male connector 2 that is attached to the tube 8 as shown in FIGS. 5A and 5B is removed from the tube 8 as follows.

First, the lock nut 250 is rotated relative to the connector body 210, in the direction opposite to that during attachment. In order to loosen the screwing together of the spiral protrusion 32 and the female threading 52, the first engaging protrusion 231 and the second engaging protrusion 252 need to be disengaged, and a somewhat large amount of rotation torque needs to be applied for disengagement. After the second engaging protrusion 252 has ridden over the first engaging protrusion 231, the lock nut 250 can be rotated relative to the connector body 210 with a small rotation torque.

After the lock nut 250 has been separated from the connector body 210 as shown in FIG. 8B, the connector body 210 is pulled out from the tube 8 (FIG. 8A). Thereafter, the tube 8 is pulled out from the lock nut 250.

The male connector 2 can be repeatedly attached to and detached from the tube 8 any number of times. When the lock nut 250 is rotated, rotation torque is easily applied by catching the ribs 57 with one's fingers.

Method of Use

The method of use of the male connector 2 is approximately the same as the method of use of the male connector 1 of Embodiment 1. Similarly to Embodiment 1, it is possible to connect the female connector 920 compliant with ISO 80369-3 (FIGS. 25A and 25B) to the male connector 2, perform enteral feeding, and thereafter separate the female connector 920 from the male connector 2. When the lock nut 250 is rotated relative to the female connector 920, the connector body 210 rotates integrally with the lock nut 250. The connection between the male connector 2 and the female connector 920 is excellent in terms of liquid-tightness and connection strength, similarly to the connection between the male connector 910 (FIGS. 24A and 24B) and the female connector 920.

Similarly to Embodiment 1, after enteral feeding has been performed, it is possible to remove the male connector 2 from the tube 8 and clean the connector body 210 and the lock nut 250 by washing them with water separately. The cleaned connector body 210 and lock nut 250 are then attached to the tube 8 again. The connector body 210 and/or the lock nut 250 may be replaced with new ones instead of being cleaned.

Similarly to Embodiment 1, in the case of installing a gastrostomy, the tube 8 is fixed to the patient, and then the male connector 2 is attached to the tip of the tube 8 that has been pulled out from the patient.

Effects

In Embodiment 2, the first engaging protrusion 231 of the connector body 210 and the second engaging protrusion 252 of the lock nut 250 engage with each other. By engaging with each other, the first engaging protrusion 231 and the second engaging protrusion 252 constitute the first rotation prevention mechanisms that prevent the lock nut 250 from rotating relative to the connector body 210. The first engaging protrusion 231 and the second engaging protrusion 252 that constitute the first rotation prevention mechanisms engage in the central axis 1a direction, and thus, in cooperation with the spiral protrusion 32 and the female threading 52, prevent relative rotation between the connector body 210 and the lock nut 250. Accordingly, it is possible to prevent the screwing together of the spiral protrusion 32 and the second female threading 52 from becoming loosened unintentionally. It is possible to release the locked state of the first rotation prevention mechanisms (i e, the engaged state of the first engaging protrusion 231 and the second engaging protrusion 252) and rotate the lock nut 250 relative to the connector body 210, but a relatively large amount of force is necessary. For this reason, when the lock nut 250 and the female connector 920 are respectively gripped and rotated in mutually opposite directions in order to separate the male connector 2 and the female connector 920 that are connected to each other, the first rotation prevention mechanisms cause the connector body 210 to rotate integrally with the lock nut 250, and therefore the screwing together of the female threading 41 and the male threading 926 is selectively loosened, without the screwing together of the spiral protrusion 32 and the female threading 52 being loosened. Accordingly, the male connector 2 and the female connector 920 can be separated without the male connector 2 becoming disassembled. The amount of force (rotation torque) necessary for putting the first rotation prevention mechanisms into the locked state and releasing the locked state can be adjusted by appropriately changing the dimensions and the like of the first engaging protrusion 231 and the second engaging protrusion 252. For example, the aforementioned force (rotation torque) can be reduced by, for example, reducing the size of the overlapping area of the first engaging protrusion 231 and the second engaging protrusion 252 when viewed along the central axis 1a.

Note that in addition to the first rotation prevention mechanisms described above, frictional force between the fixed protrusion 21 and the small diameter portion 53 applied via the tube 8 also contributes to preventing rotation of the lock nut 250 relative to the connector body 210.

Embodiment 2 has effects similar to those of Embodiment 1 with the exception of the content described above.

Embodiment 2 is the same as Embodiment 1 with the exception of the content described above. The description of Embodiment 1 applies to Embodiment 2 as well.

Embodiment 3

Configuration

A male connector 3 of Embodiment 3 is different from the male connector 1 of Embodiment 1 with respect to the configuration of the connector body. More specifically, in Embodiment 3, the connector body 10 of Embodiment 1 is divided into two parts, namely the outer tube 40 with the female threading 41 formed therein, and the remaining portion. The male connector 3 of Embodiment 3 will be described with focus on differences from the male connector 1 of Embodiment 1. In the drawings referenced below, elements the same as or corresponding to elements of the male connector 1 of Embodiment 1 are denoted by the same reference signs, and detailed descriptions will not be given for them.

Figure 9A:
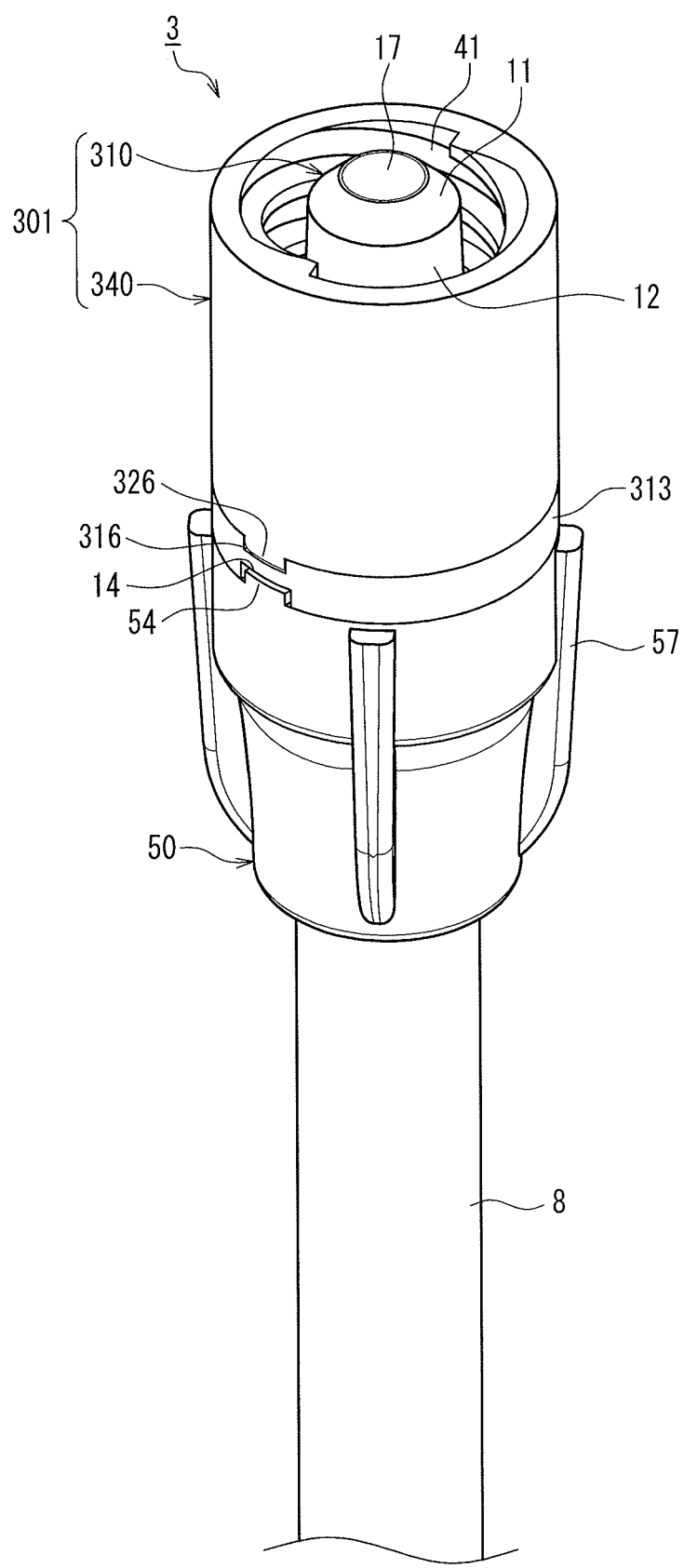
FIG. 9A is a perspective view of a male connector according to Embodiment 3 of the present invention.
Figure 9B:
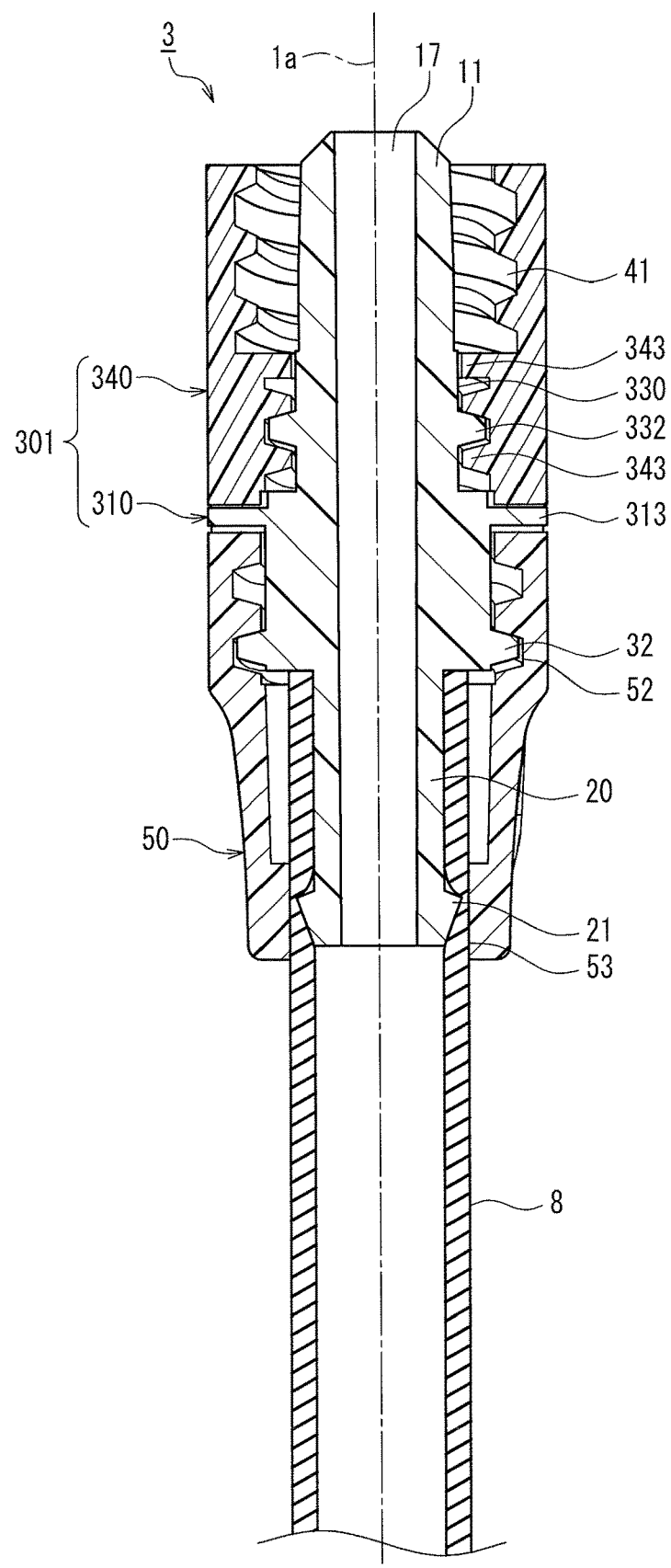
FIG. 9B is a cross-sectional view of the male connector according to Embodiment 3 of the present invention.

FIG. 9A is a perspective view of the male connector 3 according to Embodiment 3 of the present invention. FIG. 9B is a cross-sectional view taken along a plane that passes through the central axis 1a of the male connector 3. The male connector 3 of Embodiment 3 includes a luer portion 310, a lock portion 340, and the lock nut 50. The luer portion 310 and the lock portion 340 constitute a connector body 301.

Figure 10A:
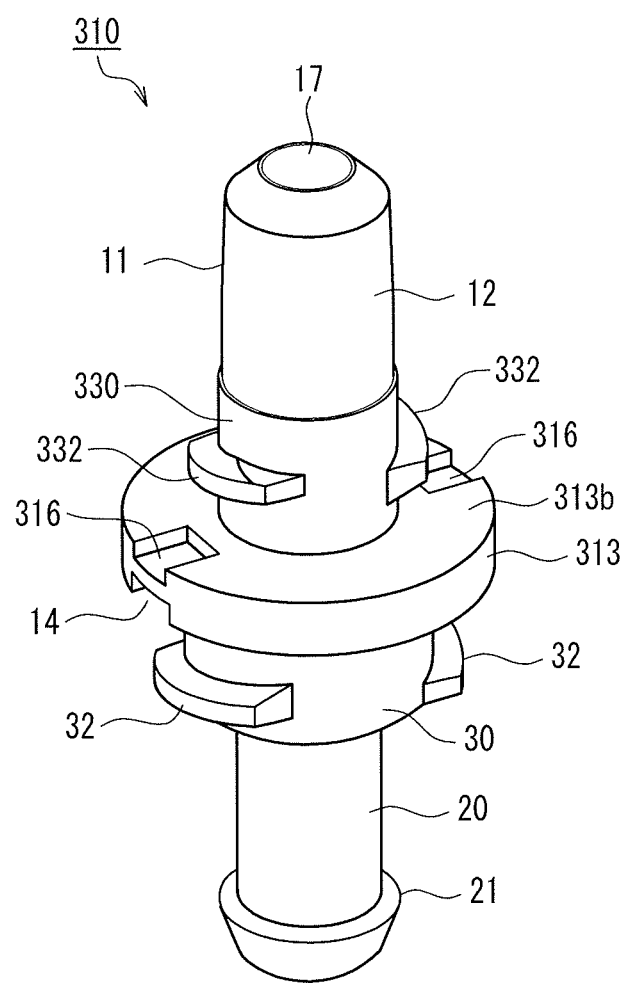
FIG. 10A is a perspective view of a luer portion that constitutes the male connector according to Embodiment 3 of the present invention, as viewed from above.
Figure 10B:
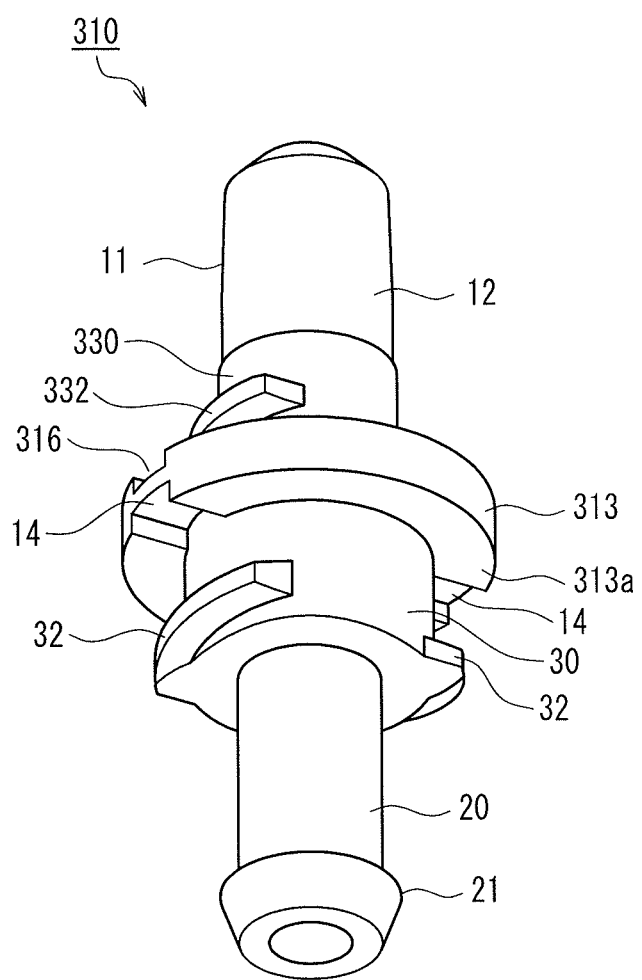
FIG. 10B is a perspective view of the luer portion that constitutes the male connector according to Embodiment 3 of the present invention, as viewed from below.
Figure 10C:
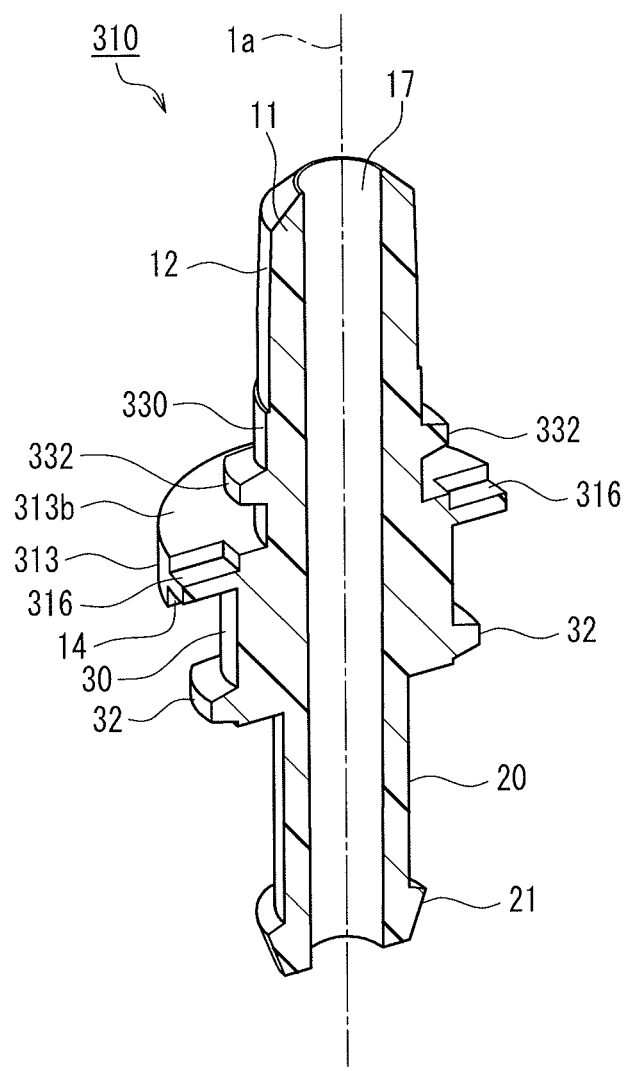
FIG. 10C is a perspective cross-sectional view of the luer portion that constitutes the male connector according to Embodiment 3 of the present invention.

FIG. 10A is a perspective view of the luer portion 310 as viewed from above, FIG. 10B is a perspective view of the luer portion 310 as viewed from below, and FIG. 10C is a perspective cross-sectional view of the luer portion 310 taken along a plane that includes the central axis 1a. The luer portion 310 includes the tubular male luer 11 at one end, and includes the tubular base end portion 20 at the other end. A disc-shaped flange 313 protrudes outward along the radial direction from a position between the male luer 11 and the base end portion 20. A lower face (face on the base end portion 20 side) 313a and an upper face (face on the male luer 11 side) 313b of the flange 313 are both a flat face that is perpendicular to the central axis 1a. A pair of receding portions (first receding portions) 14 are formed on the lower face 313a of the flange 313. A pair of receding portions (second receding portions) 316 are formed on the upper face 313b of the flange 313. The pair of receding portions 14 and the pair of receding portions 316 are both in rotation symmetry (two-fold symmetry) about the central axis 1a. The positions of the receding portions 14 and the receding portions 316 in the circumferential direction are the same in this example, but they may be different.

A tubular portion (third tubular portion) 330 is provided between the male luer 11 and the flange 313. The outer circumferential face of the tubular portion 330 is a cylindrical face whose outer diameter is constant in the central axis 1a direction. A spiral protrusion (second spiral protrusion) 332 protrudes from the outer circumferential face of the tubular portion 330. The spiral protrusion 332 is a so-called discontinuous thread, in which the thread ridge of the male threading is divided so as to be discontinuous in the circumferential direction.

Figure 11A:
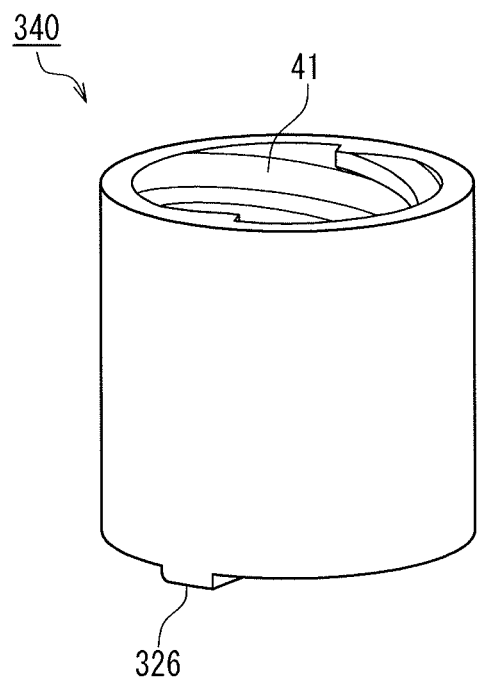
FIG. 11A is a perspective view of a lock portion that constitutes the male connector according to Embodiment 3 of the present invention, as viewed from above.
Figure 11B:
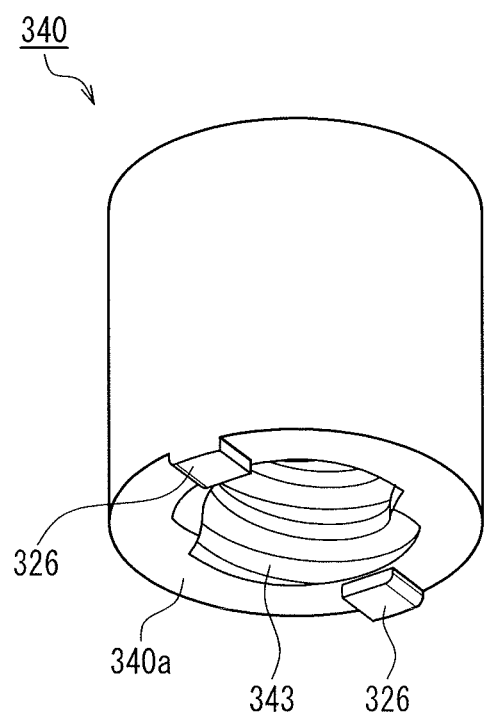
FIG. 11B is a perspective view of the lock portion that constitutes the male connector according to Embodiment 3 of the present invention, as viewed from below.
Figure 11C:
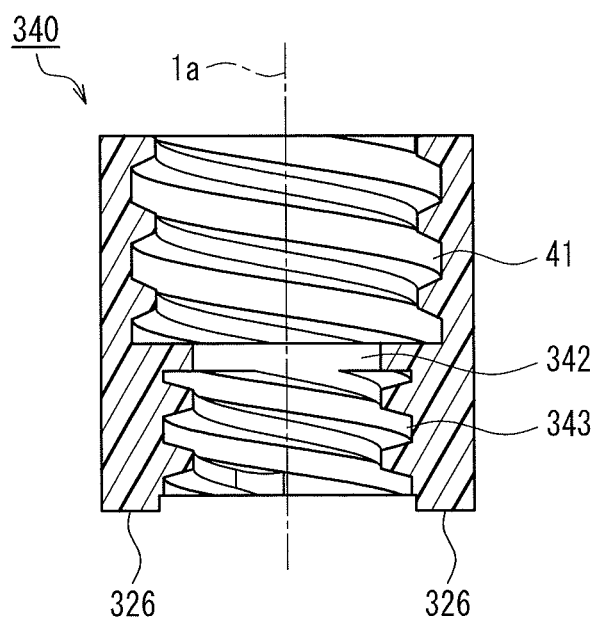
FIG. 11C is a cross-sectional view of the lock portion that constitutes the male connector according to Embodiment 3 of the present invention.

FIG. 11A is a perspective view of the lock portion 340 as viewed from above, FIG. 11B is a perspective view of the lock portion 340 as viewed from below, and FIG. 11C is a cross-sectional view of the lock portion 340 taken along a plane that includes the central axis 1a.

The lock portion 340 has a hollow, approximately cylindrical shape, and is open at the two ends in the up-down direction. As shown in FIG. 11C, in order from the top, female threading 41 (first female threading) and female threading (third female threading) 343 are formed in the inner circumferential face of the lock portion 340, and are adjacent in the central axis 1a direction. The spiral directions of the female threading 41 and the female threading 343 are the same (right-handed threading in the present embodiment), and the effective diameter of the female threading 41 is larger than that of the female threading 343.

As shown in FIG. 11B, the lower face 340a of the lock portion 340 is a flat face that is perpendicular to the central axis 1a. A pair of protruding portions (second protruding portions) 326 protrude downward from the lower face 340a of the lock portion 340. The pair of protruding portions 326 are in rotation symmetry (two-fold symmetry) about the central axis 1a.

The luer portion 310 and the lock portion 340 are made of a material that is hard (a hard material) and has a mechanical strength (rigidity) to the extent of substantially not deforming under external force. Although there are no limitations on this hard material, it is possible to use the same resin material as the material of the connector body 10 described in Embodiment 1, for example. The luer portion 310 and the lock portion 340 can each be formed in an integrated manner using injection molding or the like and the aforementioned resin materials. The materials constituting the luer portion 310 and the lock portion 340 may be the same or different from each other.

In the case where the luer portion 310 and the lock portion 340 are constituted by different materials, it is preferable that the luer portion 310 is made of a material that is relatively harder than that of the lock portion 340. For example, it is possible for the luer portion 310 to be constituted by ABS, and the lock portion 340 to be constituted by PP.

The lock nut 50 is the same as the lock nut 50 described in Embodiment 1.

Attachment to and Detachment from Tube

The male connector 3, which has the above-described configuration and is constituted by the luer portion 310, the lock portion 340, and the lock nut 50, is removably attached to the upstream end of the tube 8 (FIGS. 9A and 9B).

The male connector 3 is attached to the tube 8 as follows.

Figure 12A:
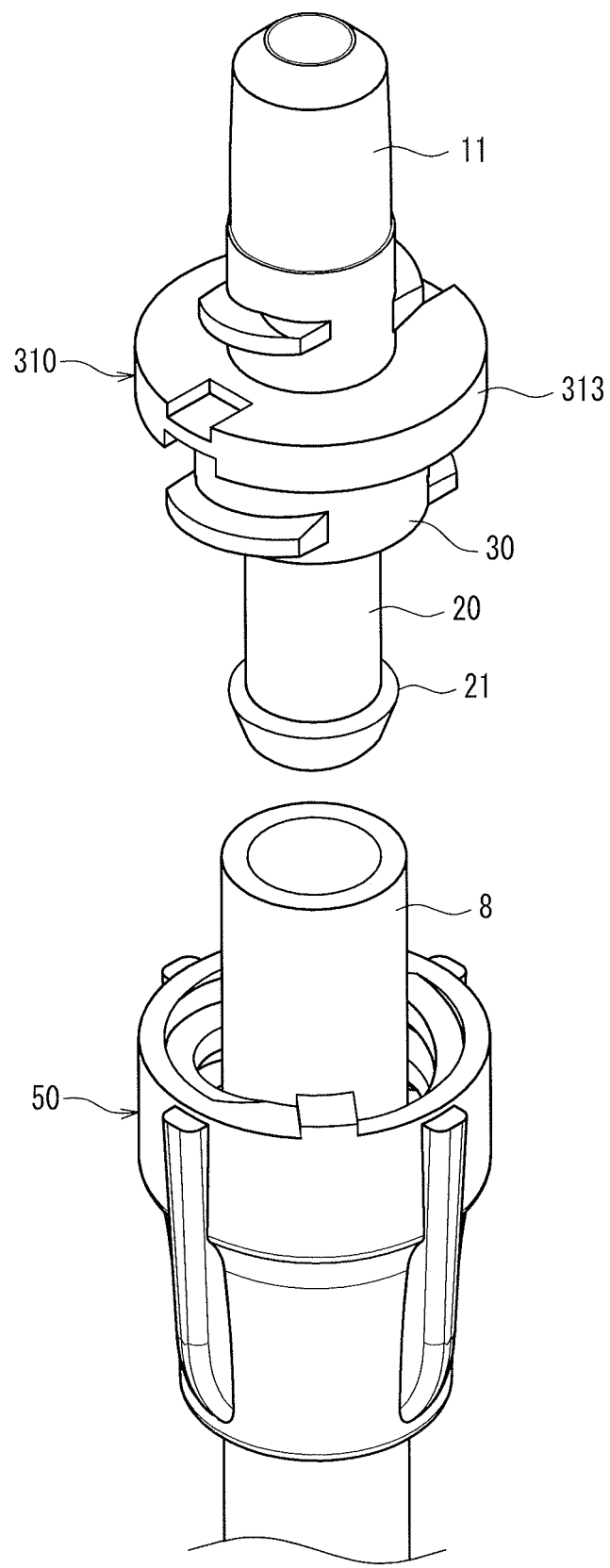
FIG. 12A is a perspective diagram showing one step for attaching the male connector according to Embodiment 3 of the present invention to a tube.

First, as shown in FIG. 12A, the tube 8 is inserted into the lock nut 50. The luer portion 310 is then arranged so as to oppose the upstream end of the tube 8.

Figure 12B:
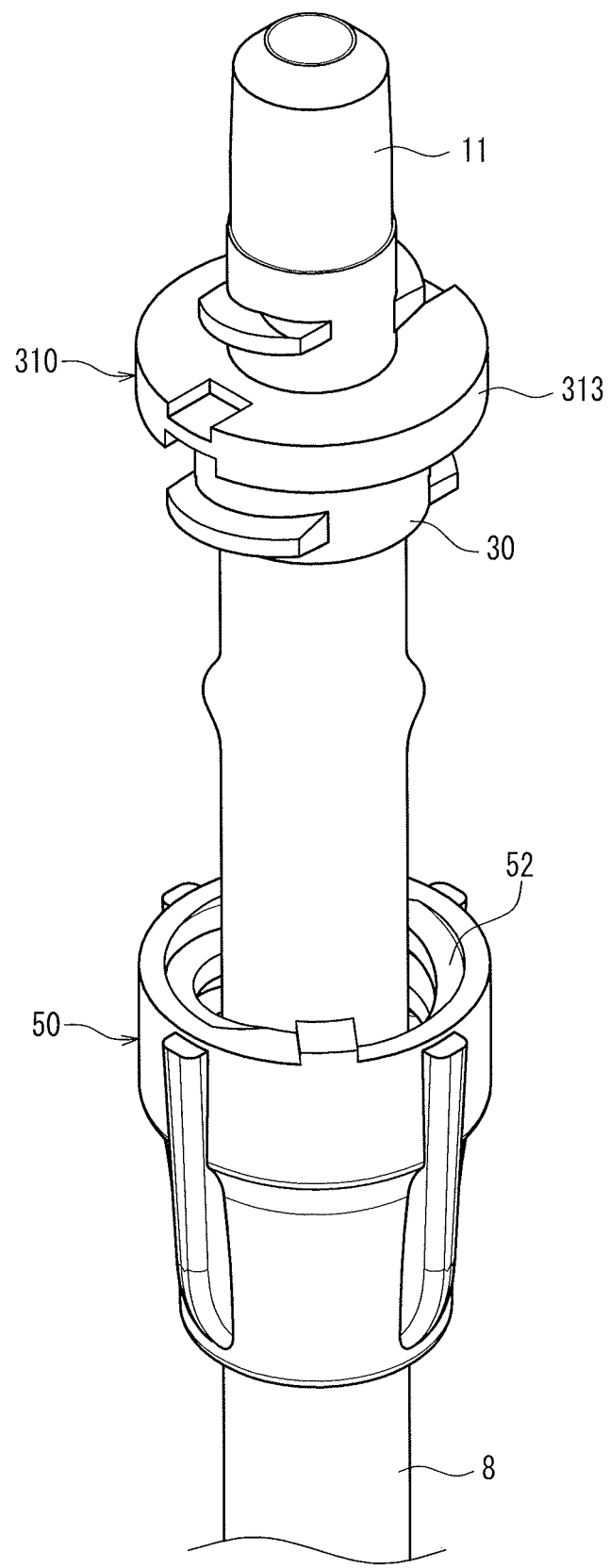
FIG. 12B is a perspective diagram showing one step for attaching the male connector according to Embodiment 3 of the present invention to a tube.

Next, as shown in FIG. 12B, the base end portion 20 of the luer portion 310 is inserted into the tube 8. Similarly to Embodiment 1, the tube 8 is widened by the fixed protrusion 21 at the position corresponding to the fixed protrusion 21.

Figure 12C:
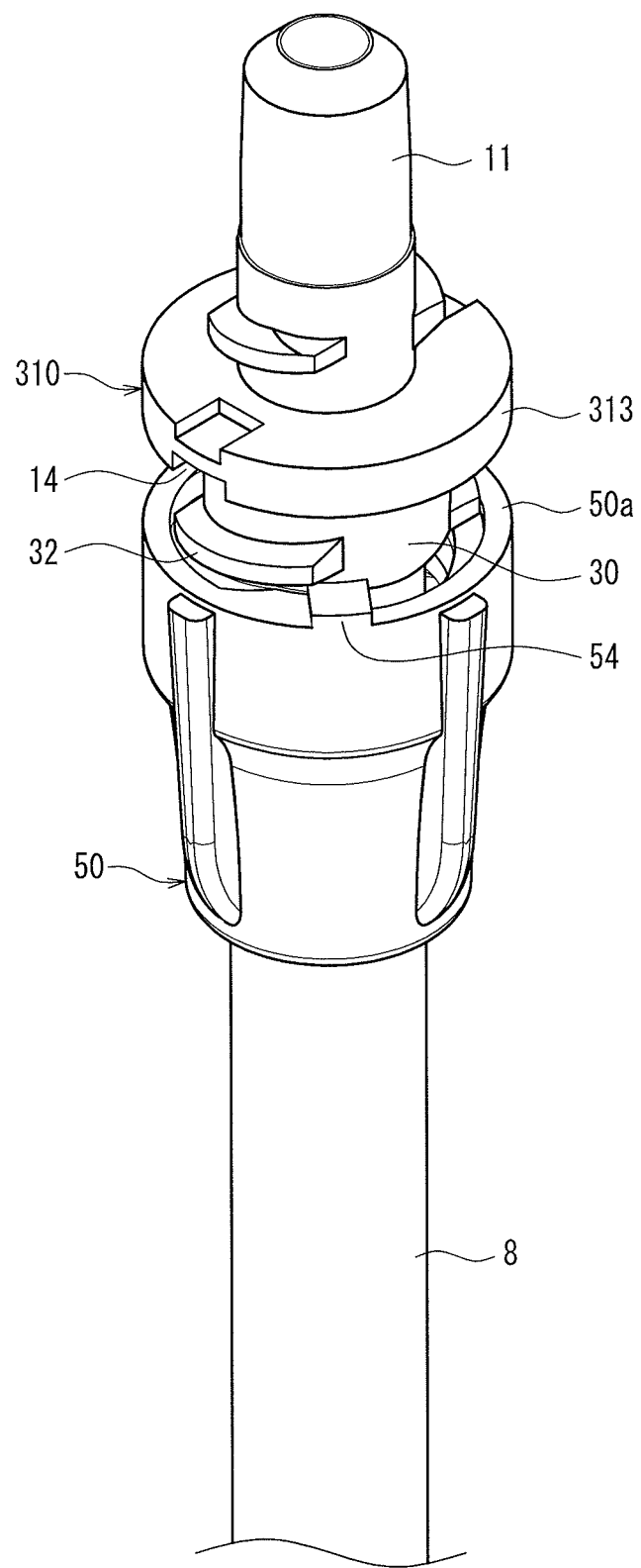
FIG. 12C is a perspective diagram showing one step for attaching the male connector according to Embodiment 3 of the present invention to a tube.

Next, as shown in FIG. 12C, the lock nut 50 is moved toward the luer portion 310. The thread ridge of the female threading 52 of the lock nut 50 collides with the spiral protrusion 32 of the luer portion 310. The lock nut 50 is rotated relative to the luer portion 310, thus screwing the spiral protrusion 32 and the female threading 52 together. As the lock nut 50 is rotated, the tubular portion 30 advances inside the lock nut 50. The pair of protruding portions 54 of the lock nut 50 soon come into contact with the lower face 313a (see FIG. 10B) of the flange 313 of the luer portion 310, and slide thereon. Finally, the pair of protruding portions 54 are fitted into the pair of receding portions 14 of the luer portion 310, and, at the same time, the upper face 50a of the lock nut 50 and the lower face 313a of the flange 313 come into contact or approach each other. When the pair of protruding portions 54 are fitted into the pair of receding portions 14, the rotation torque for rotating the lock nut 50 changes, and the operator can feel that change as a clicking sensation through their fingers.

Figure 12D:
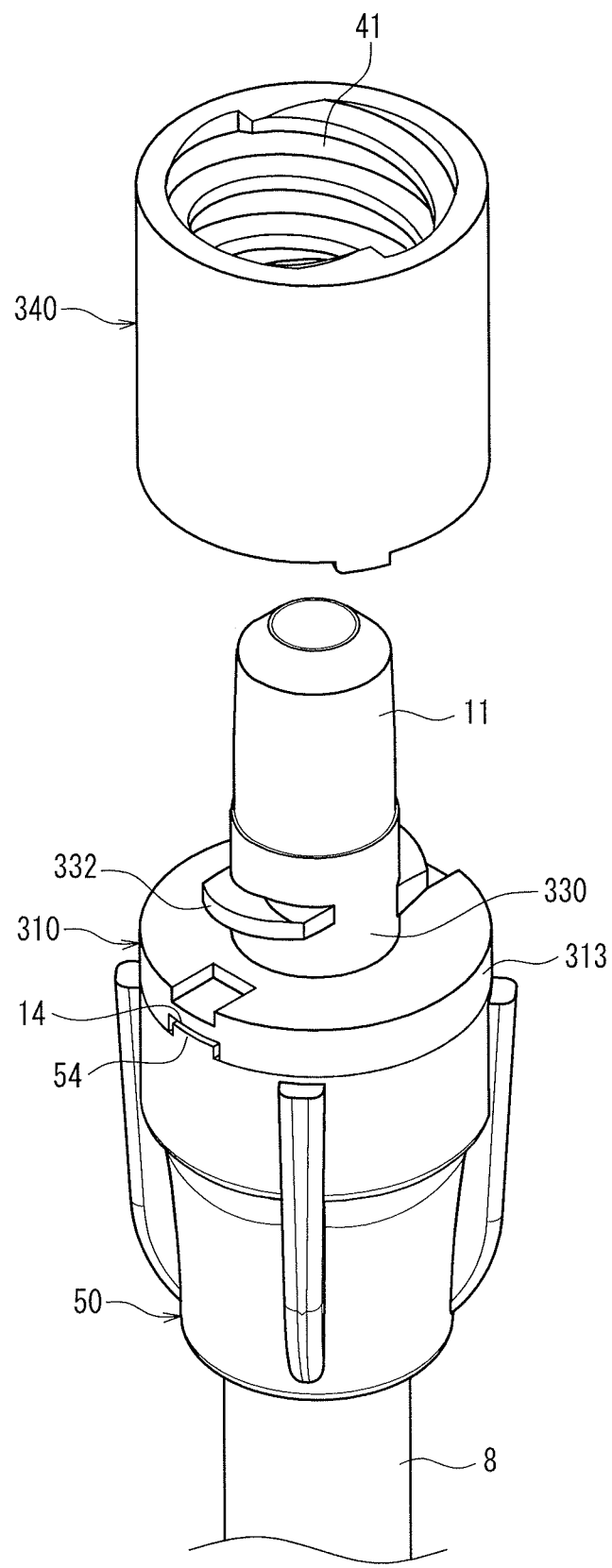
FIG. 12D is a perspective diagram showing one step for attaching the male connector according to Embodiment 3 of the present invention to a tube.

Thus, as shown in FIG. 12D, the luer portion 310 and the lock nut 50 are fixed to the upstream end of the tube 8. The protruding portions 54 of the lock nut 50 are fitted into the receding portions 14 of the luer portion 310. Although not illustrated, at this stage, similarly to Embodiment 1, the fixed protrusion 21 and the small diameter portion 53 oppose each other and clamp the tube 8 in the radial direction. The spiral protrusion 32 of the luer portion 310 is screwed together with the female threading 52 of the lock nut 50 (see FIG. 9B).

Figure 12E:
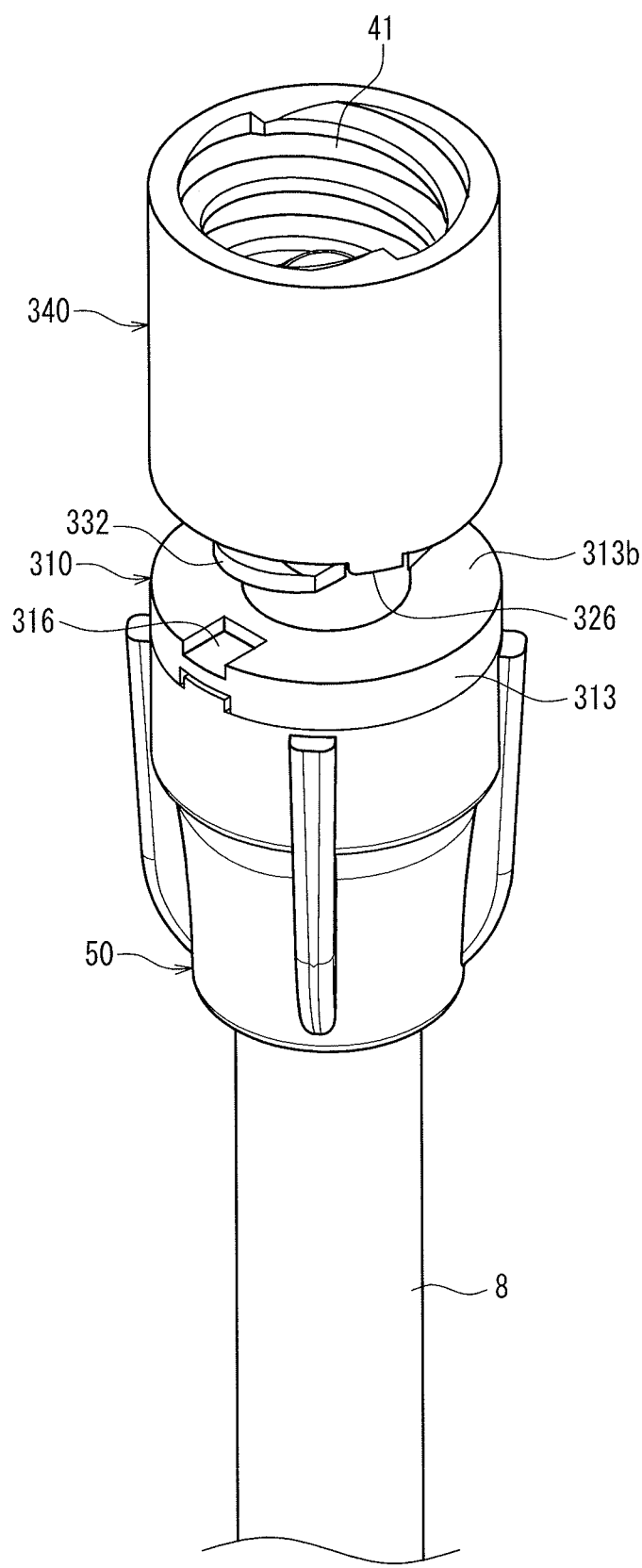
FIG. 12E is a perspective diagram showing one step for attaching the male connector according to Embodiment 3 of the present invention to a tube.

Next, the lock portion 340 is arranged so as to oppose the luer portion 310. The male luer 11 is inserted into the lock portion 340 from the lower side thereof. In FIG. 12E, the spiral protrusion 332 of the luer portion 310 collides with the thread ridge of the female threading 343 (FIGS. 11B and 11C) of the lock portion 340. The lock portion 340 is rotated relative to the luer portion 310, thus screwing the spiral protrusion 332 and the female threading 343 together. As the lock portion 340 is rotated, the male luer 11 and the tubular portion 330 advance inside the lock portion 340. The pair of protruding portions 326 of the lock portion 340 soon come into contact with the upper face 313b of the flange 313 of the luer portion 310, and slide thereon. Finally, the pair of protruding portions 326 are fitted into the pair of receding portions 316 of the luer portion 310, and, at the same time, the lower face 340a (FIG. 11B) of the lock portion 340 and the upper face 313b of the flange 313 come into contact or approach each other. When the pair of protruding portions 326 are fitted into the pair of receding portions 316, the rotation torque for rotating the lock portion 340 changes, and the operator can feel that change as a clicking sensation through their fingers.

Thus, the lock portion 340 is attached to the luer portion 310, as shown in FIGS. 9A and 9B. The protruding portions 326 are fitted into the receding portions 316. The spiral protrusion 332 and the female threading 343 have been screwed together. The channel 17 that passes through the connector body 10 is in communication with the tube 8. The male luer 11 and the female threading 41 that surrounds the male luer 11 are compliant with the above-described male connector 910 of ISO 80369-3 (FIGS. 24A and 24B). Accordingly, the male connector 3 can be connected to the female connector 920 compliant with ISO 80369-3 (FIGS. 25A and 25B).

The male connector 3 that is attached to the tube 8 as shown in FIGS. 9A and 9B is removed from the tube 8 as follows.

First, the lock portion 340 is rotated relative to the luer portion 310 in the direction opposite to that during attachment. In order to begin rotation, the protruding portions 326 and the receding portions 316 need to be disengaged, and a somewhat large amount of rotation torque needs to be applied for disengagement. After the protruding portions 326 have escaped the receding portions 316, the lock portion 340 can be easily rotated relative to the luer portion 310 with a small rotation torque. Thus, the lock portion 340 can be separated from the luer portion 310 as shown in FIG. 12D.

Next, the lock nut 50 is rotated relative to the luer portion 310 in the direction opposite to that during attachment. In order to begin rotation, the protruding portions 54 and the receding portions 14 need to be disengaged, and a somewhat large amount of rotation torque needs to be applied for disengagement. After the protruding portions 54 have escaped the receding portions 14, the lock nut 50 can be rotated relative to the luer portion 310 with a small rotation torque.

After the lock nut 50 has been separated from the luer portion 310 as shown in FIG. 12B, the luer portion 310 is pulled out from the tube 8 (FIG. 12A). Thereafter, the tube 8 is pulled out from the lock nut 50.

The method of attaching the connector 3 to the tube 8 is not limited to the above description. For example, the connector body 301 may be assembled first by attaching the lock portion 340 to the luer portion 310. Next, the base end portion 20 of the assembled connector body 301 is inserted into the upstream end of the tube 8 that has been inserted into the lock nut 50. Lastly, the lock nut 50 is attached to the connector body 301.

The method of removing the connector 3 from the tube 8 is also not limited to the above description. For example, first, the lock nut 50 may be separated from the luer portion 310 by rotating the lock nut 50. In this case, the luer portion 310 and the lock portion 340 may next be integrally pulled out from the tube 8, or a configuration is possible in which the lock portion 340 is separated from the luer portion 310, and then the luer portion 310 is pulled out from the tube 8.

The male connector 3 can be repeatedly attached to and detached from the tube 8 any number of times.

Method of Use

The method of use of the male connector 3 is approximately the same as the method of use of the male connector 1 of Embodiment 1. Similarly to Embodiment 1, it is possible to connect the female connector 920 compliant with ISO 80369-3 (FIGS. 25A and 25B) to the male connector 3, perform enteral feeding, and thereafter separate the female connector 920 from the male connector 3. When the lock nut 50 is rotated relative to the female connector 920, the luer portion 310 and the lock portion 340 rotate integrally with the lock nut 50. The connection between the male connector 3 and the female connector 920 is excellent in terms of liquid-tightness and connection strength, similarly to the connection between the male connector 910 (FIGS. 24A and 24B) and the female connector 920.

Similarly to Embodiment 1, after enteral feeding has been performed, it is possible to remove the male connector 3 from the tube 8 and clean the luer portion 310, the lock portion 340, and the lock nut 50 by washing them with water separately. The cleaned luer portion 310, lock portion 340, and lock nut 50 are then attached to the tube 8 again. Any or all of the luer portion 310, the lock portion 340, and the lock nut 50 may be replaced with new ones instead of being cleaned.

Similarly to Embodiment 1, in the case of installing a gastrostomy, the tube 8 is fixed to the patient, and then the male connector 3 is attached to the tip of the tube 8 that has been pulled out from the patient.

Effects

In Embodiment 3, the male luer 11 and the female threading (first female threading) 41 are formed on separate members (i.e., the luer portion 310 and the lock portion 340). However, when the lock portion 340 is attached to the luer portion 310 as shown in FIGS. 9A and 9B, the female threading 41 surrounds the male luer 11. Accordingly, similarly to Embodiment 1, the male connector 3 of Embodiment 3 can be connected to the female connector 920 that is compliant with ISO 80369-3 and includes the insertion portion 921 for receiving insertion of the male luer 11 and the male threading 926 that is to be screwed together with the female threading 41.

The male connector 3 is made up of three parts, namely the luer portion 310 that includes the male luer 11, the lock portion 340 that includes the female threading 41, and the lock nut 50. These three parts can be repeatedly attached to and detached from each other. Accordingly, if the male connector 3 becomes dirty due to an enteral nutrient becoming stuck to it, it is possible to disassemble the male connector 3 into the luer portion 310, the lock portion 340, and the lock nut 50, and clean them separately. After the lock portion 340 is removed from the luer portion 310, the outer circumferential face 12 of the male luer 11 is exposed (see FIG. 10A), and therefore can be cleaned easily. The spiral protrusion 332 is a discontinuous thread, and therefore the vicinity of the spiral protrusion 332 can also be cleaned easily. On the other hand, the lock portion 340 removed from the luer portion 310 is open at both ends, and the luer 11 is not present therein, thus making cleaning easy. An enteral nutrient stuck to the valleys of the female threading 41 and 343 can be removed by insertion of a brush or the like. If impurities are firmly stuck to the lock portion 340, it is also possible to replace only the lock portion 340 with a new one. In this way, the connector body 10, which is particularly likely to be become dirty among the parts constituting the connector 1 of Embodiment 1, is divided into the luer portion 310 and the lock portion 340 in Embodiment 3. Accordingly, the male connector 3 of Embodiment 3 includes the male luer 11 and the female threading 41 that surrounds the male luer 11, and can be maintained in a sanitary state more easily than in Embodiment 1.

The spiral protrusion 332 of the luer portion 310 and the female threading 343 of the lock portion 340 are screwed together. By being engaged (screwed) with each other, the spiral protrusion 332 and the female threading 343 constitute separation prevention mechanisms for preventing the luer portion 310 and the lock portion 340 from becoming separated along the central axis 1a direction. The spiral protrusion 332 and the female threading 343 that constitute the separation prevention mechanisms engage with each other in the central axis 1a direction. When the spiral protrusion 332 and the female threading 343 are screwed together, the connection strength between the luer portion 310 and the lock portion 340 in the central axis 1a direction is very large. Accordingly, the male connector 3 and the female connector 920 can be connected with liquid-tightness and a connection strength that are in compliance with ISO 80369-3. For example, when performing enteral feeding, enteral nutrients do not leak from the joining portion of the male connector 3 and the female connector 920, and the male connector 3 and the female connector 920 do not unintentionally become separated due to pressure applied to the enteral nutrient, tensile force acting on the tube 8, or the like.

Since the separation prevention mechanisms are constituted by screwing structures, the luer portion 310 and the lock portion 340 can be firmly connected, and moreover, the luer portion 310 and the lock portion 340 are easily connected/separated.

The pair of receding portions 316 of the luer portion 310 and the pair of protruding portions 326 of the lock portion 340 are fitted together. By engaging with each other (fitting together), the receding portions 316 and the protruding portions 326 constitute second rotation prevention mechanisms for preventing the lock portion 340 from rotating relative to the luer portion 310. By engaging in the circumferential direction, the protruding portions 326 and the receding portions 316 that constitute the second rotation prevention mechanisms prevent relative rotation between the luer portion 310 and the lock portion 340. Accordingly, it is possible to prevent the screwing together of the spiral protrusion (second spiral protrusion) 332 and the third female threading 343 from becoming loosened unintentionally. It is possible to release the locked state of the second rotation prevention mechanisms (i.e., the engaged state of the receding portions 316 and the protruding portions 326) and rotate the lock portion 340 relative to the luer portion 310, but a relatively large amount of force is necessary.

Furthermore, similarly to Embodiment 1, the male connector 3 includes the pair of receding portions 14 of the luer portion 310 and the pair of protruding portions 54 of the lock nut 50 that engage with (are fitted to) each other as the first rotation prevention mechanisms that prevent the lock nut 50 from rotating relative to the luer portion 310.

For this reason, when the lock nut 50 and the female connector 920 are respectively gripped and rotated in mutually opposite directions in order to separate the male connector 3 and the female connector 920 that are connected to each other, the first and second rotation prevention mechanisms cause the lock portion 340 and the luer portion 310 to rotate integrally with the lock nut 50, and therefore the screwing together of the female threading 41 and the male threading 926 is selectively loosened, without the screwing together of the spiral protrusion 32 and the female threading 52 and the screwing together of the spiral protrusion 332 and the female threading 343 being loosened. Accordingly, the male connector 3 and the female connector 920 can be separated without the male connector 3 becoming disassembled.

The amount of force (rotation torque) necessary for putting the second rotation prevention mechanisms into the locked state and releasing the locked state can be adjusted by appropriately changing the dimensions, shape, and the like of the protruding portions 326 and the receding portions 316. For example, the aforementioned force (rotation torque) can be reduced by, for example, reducing the protruding height of the protruding portions 326 from the lower face 340a of the lock portion 340, rounding or chamfering the tips of the protruding portions 326, or chamfering the edges of the openings of the receding portions 316.

Similarly to the first rotation prevention mechanisms, the second rotation prevention mechanisms also are useful in firmly screwing the female threading 41 and the male threading 926 together by respectively gripping the lock nut 50 and the female connector 920 when connecting the female connector 920 to the male connector 3.

Although the male connector 3 is constituted by three parts, namely the luer portion 310, the lock portion 340, and the lock nut 50, it includes the first and second rotation prevention mechanisms, and therefore the operability of connection to and separation from the female connector 920 is equivalent to the operability when the male connector 910 constituted by one part is connected to and separated from the female connector 920.

Embodiment 3 has effects similar to those of Embodiment 1 with the exception of the content described above.

The connector body constituted by two parts, namely the luer portion 310 and the lock portion 340, described in Embodiment 3 can also be applied to Embodiment 2.

The separation prevention mechanisms may have a configuration other than the screwing structures constituted by the spiral protrusion 332 and the female threading 343. For example, the separation prevention mechanisms may be configured by engaging structures that can engage with each other in the central axis 1a direction (e.g., one protruding portion and another protruding portion, or a protruding portion and a receding portion).

The spiral protrusion 332 and the female threading 343 that constitute separation prevention mechanisms can be omitted. In this case, the connection strength between the luer portion 310 and the lock portion 340 can be adjusted by appropriately designing the fitting of the receding portions 316 of the luer portion 310 and the protruding portions 326 of the lock portion 340 that constitute the second rotation prevention mechanisms. Accordingly, in this case as well, the male connector 3 and the female connector 920 can be connected with liquid-tightness and a connection strength that are in compliance with ISO 80369-3.

In Embodiment 3, a liquid-tight seal may be formed between the luer portion 310 and the lock portion 340. It is preferable that the seal is formed at a position lower than (on the base end portion 18 side of) the male luer 11.

For example, a tapered face whose outer diameter decreases as it approaches the male luer 11 (a so-called male tapered face) can be formed on the outer circumferential face of the tubular portion (third tubular portion) 330 of the luer portion 310 (FIG. 10A). Also, a small diameter portion 342 (FIG. 11C) can be formed between the first female threading 41 and the third female threading 343 of the lock portion 340. The inner circumferential face of the small diameter portion 342 is a tapered face whose inner diameter increases as it approaches the third female threading 343 (a so-called female tapered face). The minimum inner diameter of the small diameter portion 342 is smaller than the minimum inner diameter of the first female threading 41 and the minimum inner diameter of the third female threading 343. The female tapered face of the small diameter portion 342 has the same taper angle and diameter as the male tapered face of the tubular portion 330 of the luer portion 310.

If the male tapered face is formed on the tubular portion 330 and the female tapered face is formed on the small diameter portion 342 as described above, the tubular portion 330 and the small diameter portion 342 are fitted to each other when the lock portion 340 is attached to the luer portion 310 as shown in FIG. 9B. Since the male tapered face of the tubular portion 330 and the female tapered face of the small diameter portion 342 have the same taper angle and diameter, a liquid-tight seal is formed between the tubular portion 330 and the small diameter portion 342.

The outer circumferential face 12 of the male luer 11 comes into liquid-tight surface contact with the inner circumferential face 922 of the insertion portion 921 of the female connector 920 (FIGS. 25A and 25B). Accordingly, when the male connector 3 and the female connector 920 are in the connected state, there is a low possibility of a nutrient leaking out from between the outer circumferential face 12 of the male luer 11 and the inner circumferential face 922 of the insertion portion 921. However, if the nutrient has been filled up to the edge of the opening of the insertion portion 921 immediately before the male connector 3 and the female connector 922 are connected, there are cases where the nutrient leaks out from the insertion portion 921 when the male luer 11 is inserted into the insertion portion 921. If a liquid-tight seal is formed between the tubular portion 330 and the small diameter portion 342, a leaked nutrient does not flow between the second spiral protrusion 332 and the third female threading 343. Accordingly, it is possible to lower the possibility that a nutrient leaks out of the male connector 3 between the lower face 340a of the lock portion 340 and the upper face 313b of the flange 313 and soils the patient's body or clothes. It is also possible to suppress the attachment of a nutrient to the luer portion 310 and the lock portion 340, and facilitate the operation of cleaning them. Furthermore, it is possible to reduce the possibility of a situation occurring in which a nutrient that leaked out from between the luer portion 310 and the lock portion 340 becomes stuck thereto and makes it difficult to separate the luer portion 310 and the lock portion 340.

The liquid-tight seal between the luer portion 310 and the lock portion 340 is not limited to being formed by a male tapered face and a female tapered face that are fitted to each other. For example, a liquid-tight seal may be formed by two cylindrical faces that can be fitted to each other. A liquid-tight seal may be formed by attaching an O-ring to either the luer portion 310 or the lock portion 340, and bringing the O-ring into close contact with the other one.

The position where the liquid-tight seal is formed may be any position, as long as the position is lower than (on the base end portion 18 side relative to) the male luer 11. For example, the seal may be formed below the second spiral protrusion 332 and the third female threading 343. The seal does not need to be formed at a position where the luer portion 310 and the lock portion 340 oppose each other in the radial direction, and it may be formed at a position where the luer portion 310 and the lock portion 340 oppose each other in the up-down direction (e.g., between the upper face 313b of the flange 313 and the lower face 340a of the lock portion 340), for example.

Embodiment 3 is the same as Embodiment 1 with the exception of the content described above. The description of Embodiment 1 applies to Embodiment 3 as well.

Embodiment 4

Configuration

A male connector 4 of Embodiment 4 has mainly the following two differences from the male connector 1 of Embodiment 1. Firstly, the connector body has a pair of extension portions that extend downward. Secondly, the configuration of the first rotation prevention mechanisms is different. The male connector 4 of Embodiment 4 will be described with focus on differences from the male connector 1 of Embodiment 1. In the drawings referenced below, elements the same as or corresponding to elements of the male connector 1 of Embodiment 1 are denoted by the same reference signs, and detailed descriptions will not be given for them.

Figure 13A:
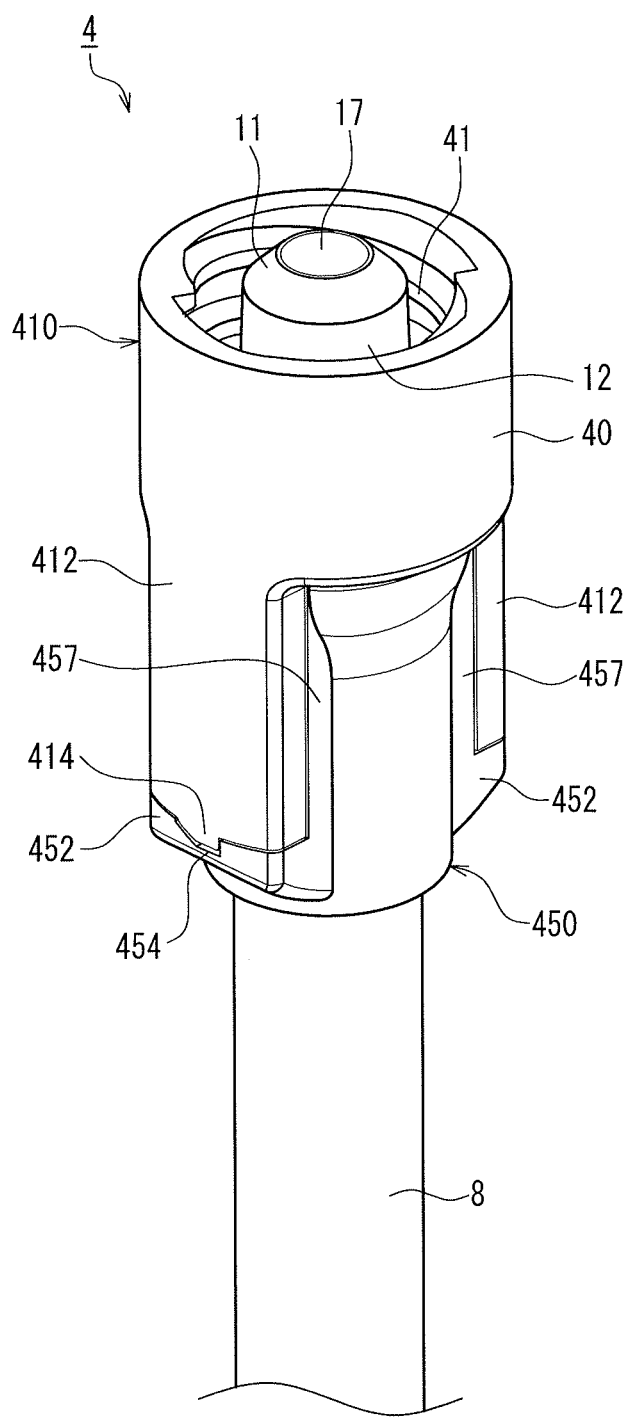
FIG. 13A is a perspective view of a male connector according to Embodiment 4 of the present invention.
Figure 13B:
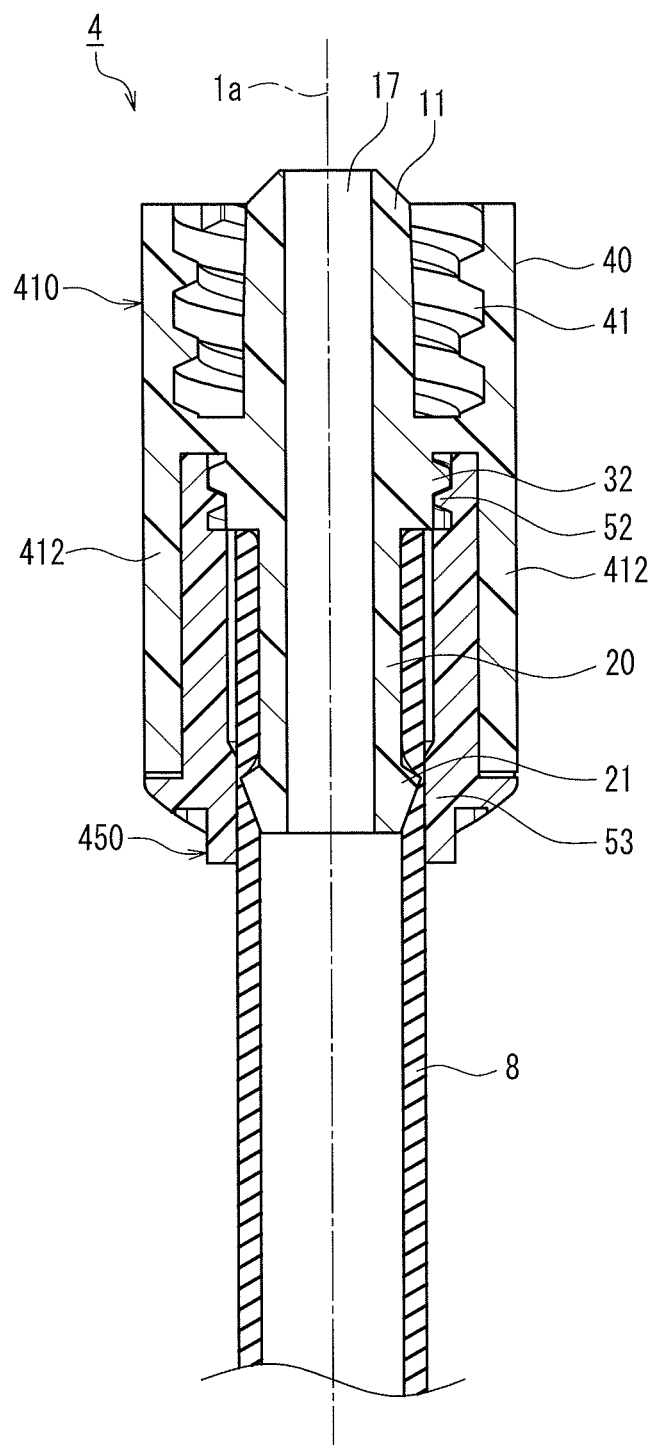
FIG. 13B is a cross-sectional view taken along a plane that includes the central axis of the male connector according to Embodiment 4 of the present invention.
Figure 13C:
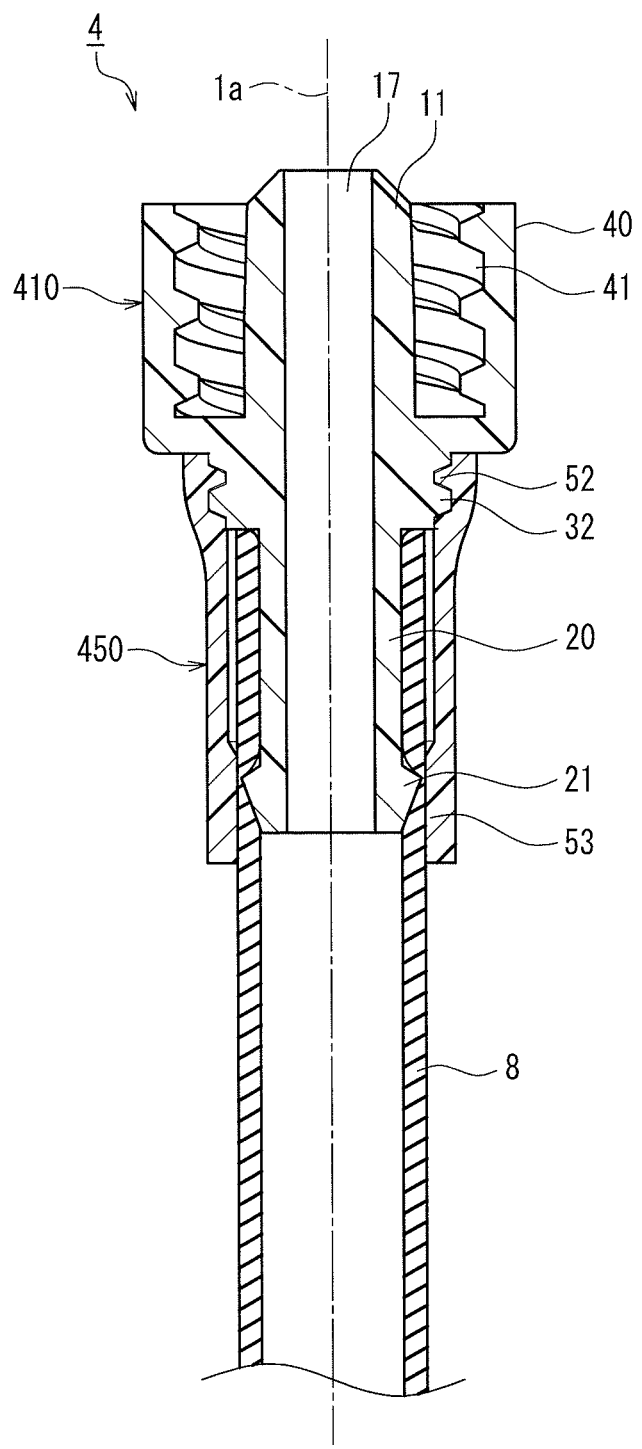
FIG. 13C is a cross-sectional view taken along a different plane that includes the central axis of the male connector according to Embodiment 4 of the present invention.

FIG. 13A is a perspective view of the male connector 4 according to Embodiment 4 of the present invention. FIG. 13B is a cross-sectional view taken along a plane that included the central axis 1a and extension portions 412 of the male connector 4. FIG. 13C is a cross-sectional view taken along a different plane that includes the central axis 1a of the male connector 4. The cross-section in FIG. 13C is orthogonal to the cross-section in FIG. 13B. Similarly to the male connector 1 of Embodiment 1, the male connector 4 of Embodiment 4 includes a connector body 410 and a lock nut 450.

Figure 14A:
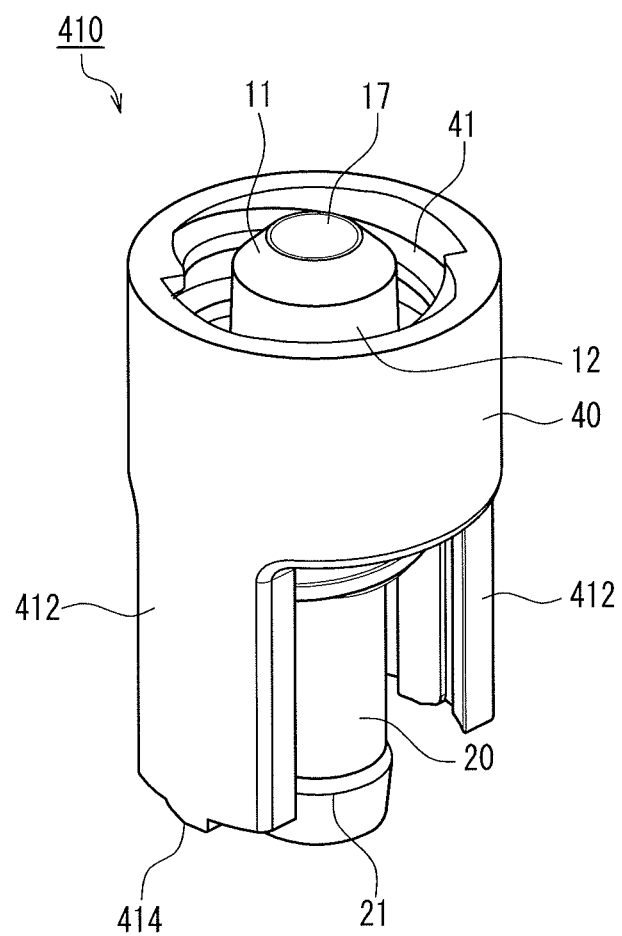
FIG. 14A is a perspective view of a connector body that constitutes the male connector according to Embodiment 4 of the present invention, as viewed from above.
Figure 14B:
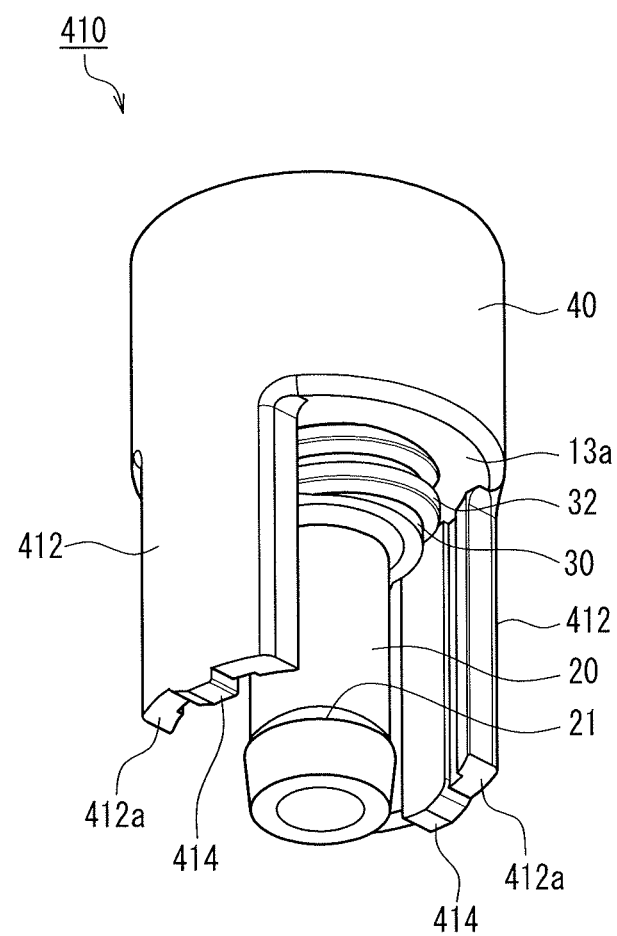
FIG. 14B is a perspective view of the connector body that constitutes the male connector according to Embodiment 4 of the present invention, as viewed from below.
Figure 14C:
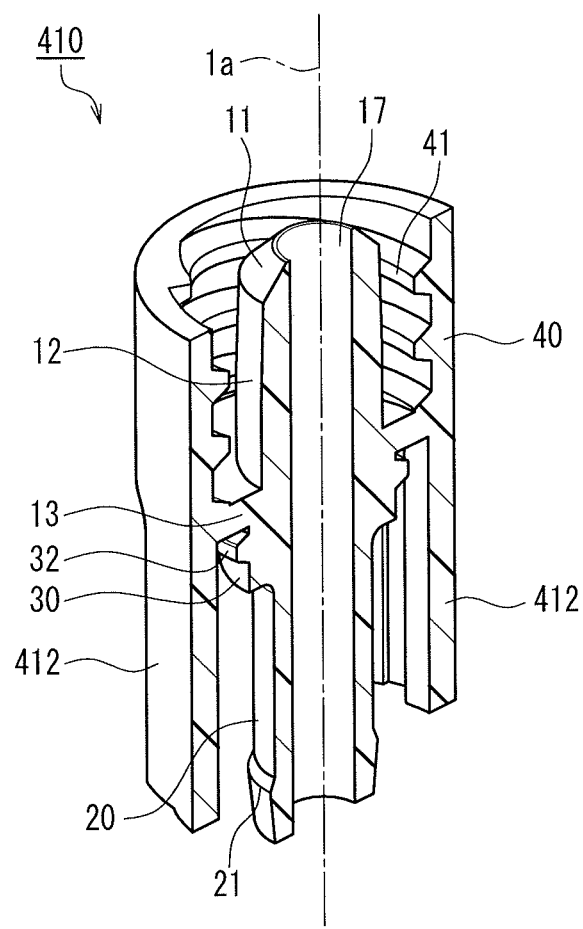
FIG. 14C is a perspective cross-sectional view of the connector body that constitutes the male connector according to Embodiment 4 of the present invention.

FIG. 14A is a perspective view of the connector body 410 as viewed from above, FIG. 14B is a perspective view of the connector body 410 as viewed from below, and FIG. 14C is a perspective cross-sectional view of the connector body 410 taken along a plane that includes the central axis 1a.

As shown most clearly in FIG. 14B, the pair of receding portions 14 (FIG. 2B) included in the connector body 10 of Embodiment 1 are not included in the connector body 410. A pair of extension portions 412 extend downward from the outer circumferential edge of the disc-shaped flange 13. The extension portions 412 are bar-shaped (arm-shaped) members that extend in the up-down direction. The gap between the pair of extension portions 412 is the same as or slightly larger than the maximum outer diameter of the portion of the lock nut 450 above a protrusion 452 (see FIG. 15A described later). The outer circumferential faces of the pair of extension portions 412 (the faces facing away from the central axis 1a) constitute a cylindrical face that is in common with the outer circumferential face of the outer tube 40. Lower faces 412a of the extension portions 412 are flat surfaces that are perpendicular to the central axis 1a. Protruding portions 414 protrude downward from the lower faces 412a of the extension portions 412. The pair of extension portions 412 and the pair of protruding portions 414 are in rotation symmetry (two-fold symmetry) about the central axis 1a.

In Embodiment 4, the spiral protrusion (first spiral protrusion) 32 formed on the outer circumferential face of the tubular portion 30 is a so-called continuous thread with a thread ridge that is continuous. It should be noted that the spiral protrusion 32 may be a discontinuous thread similar to the spiral protrusion 32 of Embodiment 1.

Figure 15A:
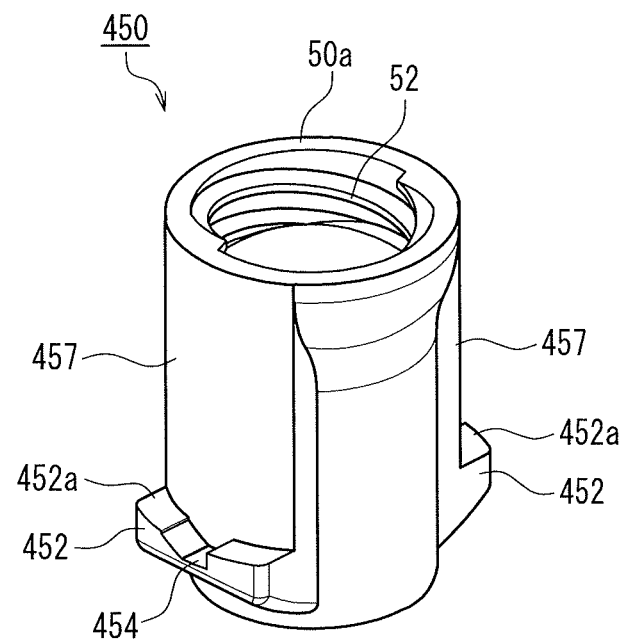
FIG. 15A is a perspective view of a lock nut that constitutes the male connector according to Embodiment 4 of the present invention, as viewed from above.
Figure 15B:
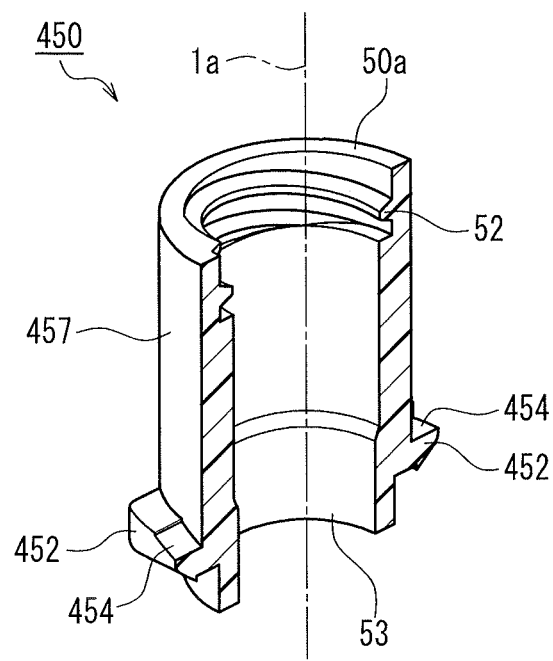
FIG. 15B is a perspective cross-sectional view of the lock nut that constitutes the male connector according to Embodiment 4 of the present invention.

FIG. 15A is a perspective view of the lock nut 450 as viewed from above, and FIG. 15B is a perspective cross-sectional view of the lock nut 450.

The protruding portions 54 (FIG. 3A) included on the lock nut 50 of Embodiment 1 are not included on the upper face 50a of the lock nut 450. Also, the ribs 57 (FIG. 3A) included on the lock nut 50 of Embodiment 1 are not included on the outer circumferential face of the lock nut 450.

A pair of ribs (protrusions) 457 that protrude outward are provided on the outer circumferential face of the lock nut 450. The ribs 457 extend downward in the up-down direction from the outer circumferential edge of the upper face 50a of the lock nut 450. The outer circumferential faces of the ribs 457 are cylindrical faces that are coaxial with the central axis 1a of the lock nut 450. A protrusion 452 protrudes outward in the radial direction from the lower end of each of the ribs 457. The protrusions 452 extend along the circumferential direction. Upper faces 452a of the protrusions 452 are flat surfaces that are perpendicular to the central axis 1a. Receding portions 454 are formed in the upper faces 452a of the protrusions 452. The pair of ribs 457, the pair of protrusions 452, and the pair of receding portions 454 are in rotation symmetry (two-fold symmetry) about the central axis 1a.

Although the ribs 457 protrude in the radial direction from the outer circumferential face of the lock nut 450 in the present embodiment, the ribs 457 may be omitted. In this case, the outer circumferential face of the lock nut 450 can be formed as a cylindrical face that has the same outer diameter as the ribs 457, for example.

The configuration of the male connector 4 is the same as the male connector 1 of Embodiment 1 with the exception of the content described above.

Attachment to and Detachment from Tube

The male connector 4, which has the above-described configuration and is constituted by the connector body 410 and the lock nut 450, is removably attached to the upstream end of the tube 8 (FIGS. 13A to 13C).

The male connector 4 is attached to the tube 8 as follows.

Figure 16A:
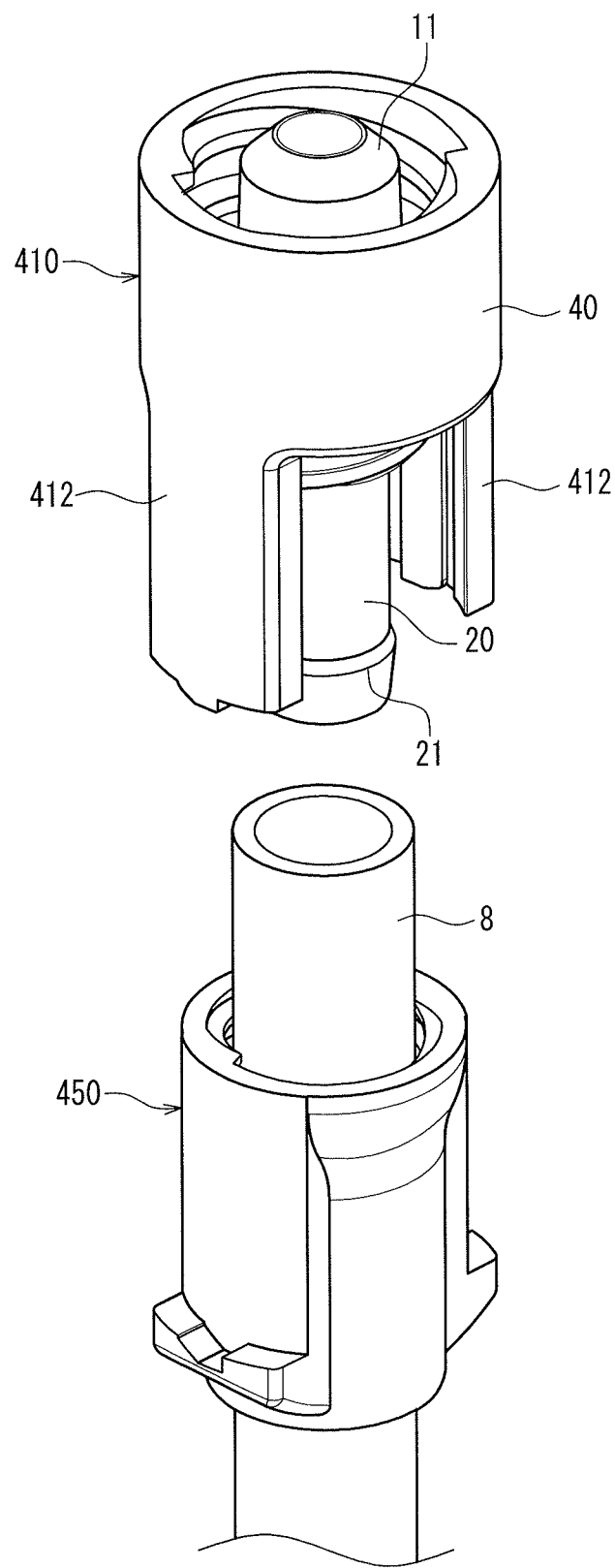
FIG. 16A is a perspective diagram showing one step for attaching the male connector according to Embodiment 4 of the present invention to a tube.

First, as shown in FIG. 16A, the tube 8 is inserted into the lock nut 450. The connector body 410 is then arranged so as to oppose the upstream end of the tube 8.

Figure 16B:
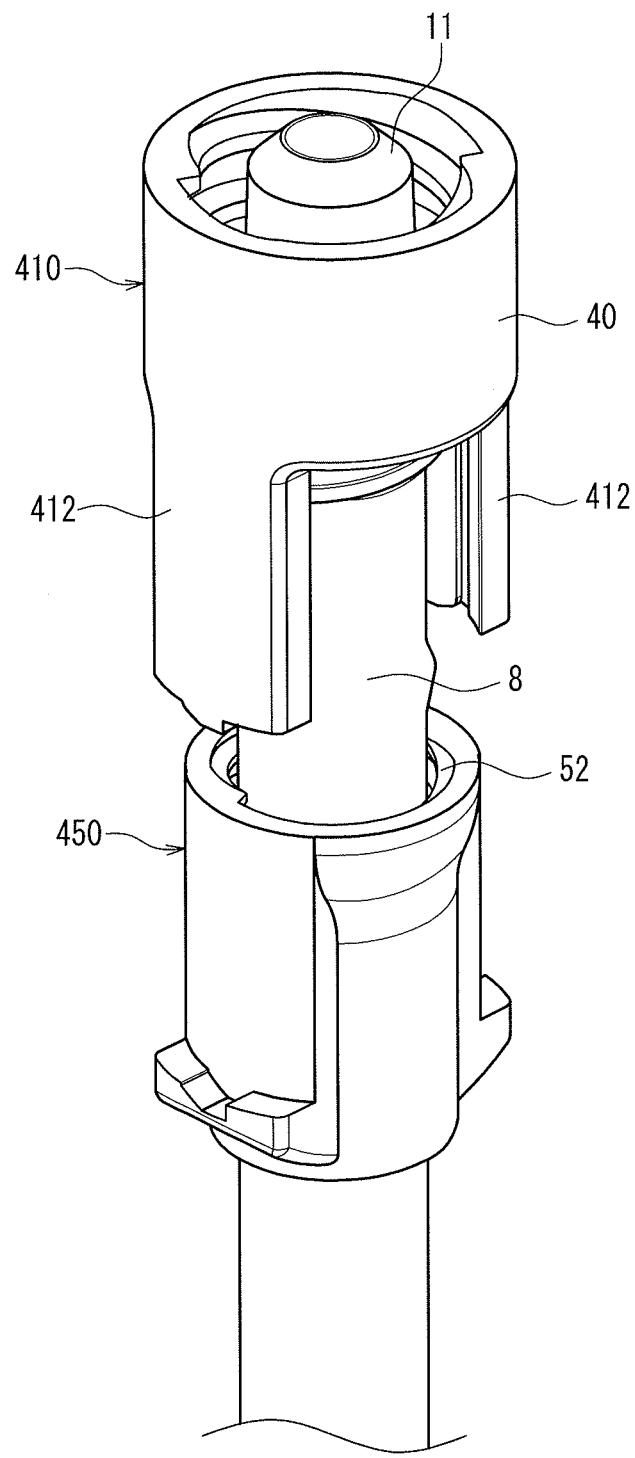
FIG. 16B is a perspective diagram showing one step for attaching the male connector according to Embodiment 4 of the present invention to a tube.

Next, as shown in FIG. 16B, the base end portion 20 of the connector body 410 is inserted into the tube 8. Similarly to Embodiment 1, the tube 8 is widened by the fixed protrusion 21 at the position corresponding to the fixed protrusion 21.

Figure 16C:
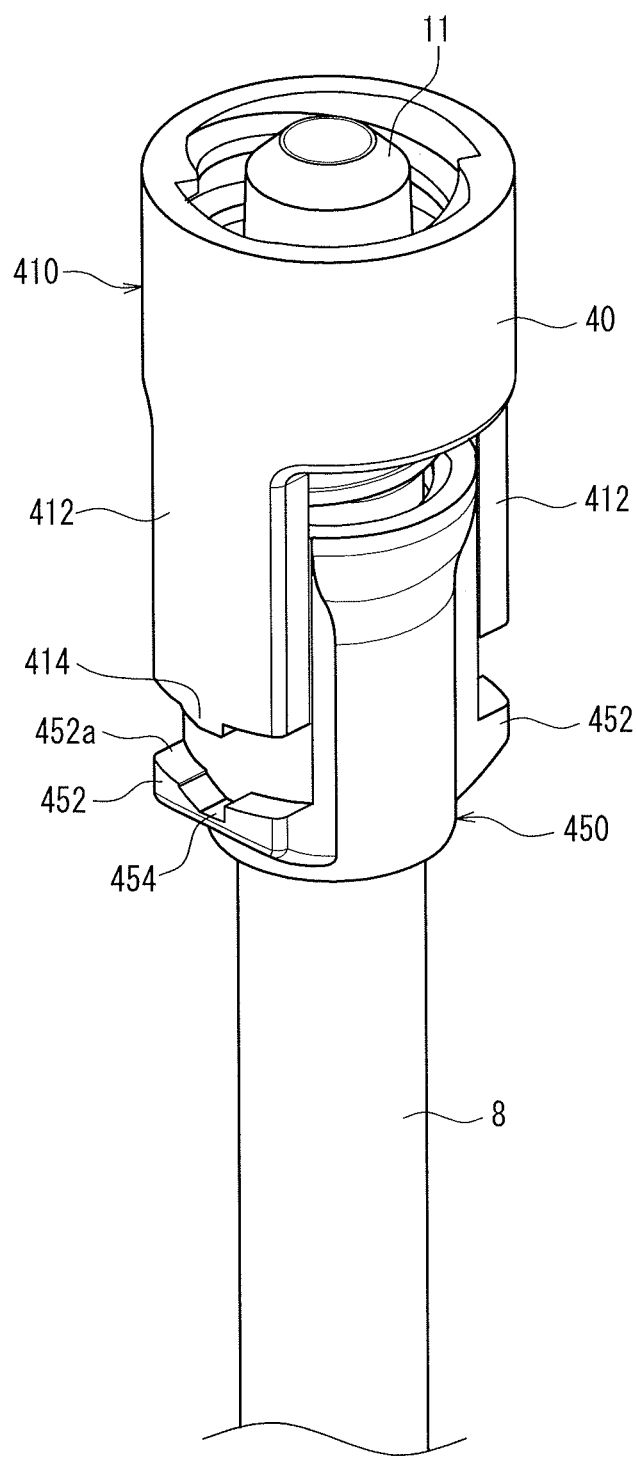
FIG. 16C is a perspective diagram showing one step for attaching the male connector according to Embodiment 4 of the present invention to a tube.

Next, as shown in FIG. 16C, the lock nut 450 is moved toward the connector body 410. The lock nut 450 is inserted between the pair of extension portions 412. The lock nut 450 is rotated relative to the connector body 410, thus screwing the spiral protrusion 32 (FIG. 14B) and the female threading 52 (FIG. 15A) together. The lock nut 450 approaches the outer tube 40 of the connector body 410. The protruding portions 414 of the extension portions 412 soon come into contact with the upper faces 452a of the protrusions 452, and slide thereon. Finally, the protruding portions 414 are fitted into the receding portions 454, and, at the same time, the lower faces 412a of the extension portions 412 and the upper faces 452a of the protrusions 452 oppose each other. When the pair of protruding portions 414 are fitted into the pair of receding portions 454, the rotation torque for rotating the lock nut 450 changes, and the operator can feel that change as a clicking sensation through their fingers.

Thus, the male connector 4 is attached to the upstream end of the tube 8 as shown in FIGS. 13A to 13C.

As shown in FIG. 13A, the pair of extension portions 412 of the connector body 410 are arranged on respective sides of the lock nut 450. The extension portions 412 and the ribs 457 of the lock nut 450 oppose each other in the radial direction, and the extension portions 412 and the protrusions 452 oppose each other in the up-down direction. The exposed outer faces of the extension portions 412 constitute an approximately continuous face with the side faces of the ribs 457 and the outer faces of the protrusions 452. The protruding portions 414 are fitted into the receding portions 454.

As shown in FIGS. 13B and 13C, the fixed protrusion 21 and the small diameter portion 53 oppose each other and clamp the tube 8 while compressing it in the radial direction. The spiral protrusion 32 of the connector body 410 is screwed together with the female threading 52 of the lock nut 450. The channel 17 that passes through the connector body 410 is in communication with the tube 8.

The male connector 4 that is attached to the tube 8 as shown in FIGS. 13A to 13C is removed from the tube 8 as follows.

First, the lock nut 450 is rotated relative to the connector body 410, in the direction opposite to that during attachment. In order to begin rotation, the protruding portions 414 and the receding portions 454 need to be disengaged, and a somewhat large amount of rotation torque needs to be applied for disengagement. After the protruding portions 414 have escaped the receding portions 454, the lock nut 450 can be rotated relative to the connector body 410 with a small rotation torque.

After the lock nut 450 has been separated from the connector body 410 as shown in FIG. 16B, the connector body 410 is pulled out from the tube 8 (FIG. 16A). Thereafter, the tube 8 is pulled out from the lock nut 450.

When the connector body 410 and the lock nut 450 are rotated in opposite directions, the outer tube 40 is pinched with one hand, and the pair of protrusions 452 are pinched with the other hand.

The male connector 4 can be repeatedly attached to and detached from the tube 8 any number of times.

Method of Use

The method of use of the male connector 4 is approximately the same as the method of use of the male connector 1 of Embodiment 1. Similarly to Embodiment 1, it is possible to connect the female connector 920 compliant with ISO 80369-3 (FIGS. 25A and 25B) to the male connector 4, perform enteral feeding, and thereafter separate the female connector 920 from the male connector 4. The connection between the male connector 4 and the female connector 920 is excellent in terms of liquid-tightness and connection strength, similarly to the connection between the male connector 910 (FIGS. 24A and 24B) and the female connector 920.

Similarly to Embodiment 1, after enteral feeding has been performed, it is possible to remove the male connector 4 from the tube 8 and clean the connector body 410 and the lock nut 450 by washing them with water separately. The cleaned connector body 410 and lock nut 450 are then attached to the tube 8 again. Either or both of the connector body 410 and the lock nut 450 may be replaced with new ones instead of being cleaned.

Similarly to Embodiment 1, in the case of installing a gastrostomy, the tube 8 is fixed to the patient, and then the male connector 4 is attached to the tip of the tube 8 that has been pulled out from the patient.

Effects

In Embodiment 4, the connector body 410 has the pair of extension portions 412 that extend downward. As shown in FIG. 13A, when the lock nut 450 has been attached to the connector body 410, the pair of extension portions 412 of the connector body 410 are arranged radially outward relative to the lock nut 450. The extension portions 412 protrude outward from the outer circumferential face of the lock nut 450. The extension portions 412 reach the vicinity of the lower end of the lock nut 450. The vertical dimension from the lower ends of the extension portions 412 to the lower end of the lock nut 450 is preferably greater than or equal to half of the vertical dimension of the lock nut 450, more preferably greater than or equal to ⅔ of the same, and particularly preferably greater than or equal to ¾ of the same. Also, the vertical dimension of the extension portions 412 is much larger than the vertical dimension of the protrusions 452. Accordingly, if the outer circumferential face of the lock nut 450 is gripped, the pair of extension portions 412 can also be gripped at the same time.

Similarly to Embodiment 1, the first female threading 41 and the male threading 926 need to be screwed together when connecting the male connector 4 and the female connector 920 (see FIGS. 25A and 25B), and the screwing together of the first female threading 41 and the male threading 926 needs to be loosened when separating the male connector 4 and the female connector 920. In such cases, the rotation torque for rotating the male connector 4 relative to the female connector 920 can be applied to the pair of extension portions 412 in Embodiment 4, rather than the lock nut 450. The pair of extension portions 412 and the first female threading 41 are provided on the connector body 410 in common. Accordingly, the rotation torque that is applied to the pair of extension portions 412 is reliably transmitted to the first female threading 41.

For example, if the male connector 4 and the female connector 920 (see FIGS. 25A and 25B) are firmly twisted during connection, there are cases where it is difficult to thereafter loosen the screwing together of the first female threading 41 and the male threading 926. In such a case as well, the screwing together of the first female threading 41 and the male threading 926 can be loosened by applying a large amount of rotation torque to the pair of extension portions 412.

In contrast, with the connector 1 (see FIG. 1A) of Embodiment 1, rotation torque is applied to the lock nut 50. Ribs 57 are provided on the lock nut 50 such that rotation torque is easily applied to the lock nut 50. The lock nut 50 to which rotation torque is applied is a separate member from the connector body 10 in which the first female threading 41 is provided. Rotation torque is transmitted from the lock nut 50 to the connector body 10 via the first rotation prevention mechanisms made up of the protruding portions 54 and the receding portions 14. Accordingly, in the case where the first female threading 41 and the male threading 926 have been screwed together firmly, if a large amount of rotation torque is applied to the lock nut 50, it is possible for a situation to occur in which instead of the screwing together of the first female threading 41 and the male threading 926 being loosened, the engagement (fitting together) of the protruding portions 54 and the receding portions 14 is released, and the screwing together of the spiral protrusion 32 and the second female threading 52 is loosened. In Embodiment 1, the engagement (fitting together) of the protruding portions 54 and the receding portions 14 needs to be firm in order to prevent such a situation from occurring. However, this reduces the operability of the connection/separation of the connector body 10 and the lock nut 50.

In Embodiment 4, the first rotation prevention mechanisms made up of the receding portions 454 and the protruding portions 414 are not arranged in the path of transmission of rotation torque applied to the male connector 4 during the connection/separation of the male connector 4 and the female connector 920. Accordingly, when separating the male connector 4 and the female connector 920, it is possible to reliably loosen the screwing together of the first female threading 41 and the male threading 926, without loosening the screwing together of the spiral protrusion 32 and the second female threading 52.

Similarly to Embodiment 1, in Embodiment 4 as well, by engaging with each other (fitting together), the pair of protruding portions 414 of the connector body 410 and the pair of receding portions 454 of the lock nut 450 constitute first rotation prevention mechanisms for preventing the lock nut 450 from rotating relative to the connector body 410. The first rotation prevention mechanisms of Embodiment 4 need only be able to prevent the screwing together of the spiral protrusion 32 and the second female threading 52 from becoming loosened unintentionally. The first rotation prevention mechanisms made up of the protruding portions 414 and the receding portions 454 of the present embodiment do not need to transmit a large amount of rotation torque, unlike the first rotation prevention mechanisms made up of the receding portions 14 and the protruding portions 54 in Embodiment 1, and thus there is an improvement in the degree of freedom in design. Also, there is an improvement in the operability of the connection/separation of the connector body 410 and the lock nut 450.

Although the male connector 4 is constituted by two parts, namely the connector body 410 and the lock nut 450, it has a configuration in which the lock nut 450 and the pair of extension portions 412 of the connector body 410 can be gripped integrally, and therefore the operability of connection to and separation from the female connector 920 is equivalent to the operability when the male connector 910 constituted by one part is connected to and separated from the female connector 920.

When the connector body 410 and the lock nut 450 have been connected, the extension portions 412 of the connector body 410 and the protrusions 452 and the ribs 457 of the lock nut 450 are continuous in the up-down direction and the radial direction as if they were one object (see FIG. 13A). Accordingly, when the lock nut 450 is gripped, even if the extension portions 412 and the protrusions 452 and/or the ribs 457 are gripped at the same time, relative rotation force does not act between the connector body 410 and the lock nut 450. Accordingly, in view of this point as well, the screwing together of the spiral protrusion 32 and the second female threading 52 does not become loosened during the operations for connecting/separating the male connector 4 to/from the female connector 920.

Figure 17A:
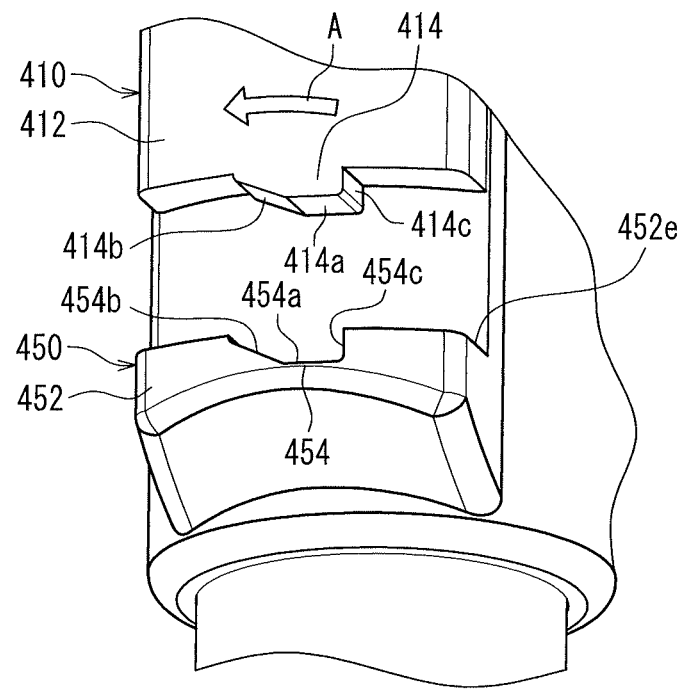
FIG. 17A is a perspective diagram showing a protruding portion and a receding portion that constitute first rotation prevention mechanisms of the male connector according to Embodiment 4 of the present invention.

FIG. 17A is a perspective view of a protruding portion 414 and a receding portion 454 that constitute the first rotation prevention mechanisms. The protruding portion 414 includes a top face (most protruding face) 414a that is parallel with the horizontal direction, an inclined face 414b that is inclined relative to the horizontal direction and is adjacent to the top face 414a on one side in the circumferential direction, and a vertical face 414c that is parallel with the up-down direction and is adjacent to the top face 414a on the other side in the circumferential direction. The receding portion 454 includes a bottom face 454a, an inclined face 454b, and a vertical face 454c that respectively correspond to the top face 414a, the inclined face 414b, and the vertical face 414c of the protruding portion 414. An arrow A indicates the direction of movement of the protruding portion 414 relative to the receding portion 454 when the lock nut 450 provided with the receding portion 454 is rotated relative to the connector body 410 provided with the protruding portion 414 so as to connect the lock nut 450 to the connector body 410. The protruding portion 414 includes the inclined face 414b on the forward side of the arrow A, and therefore the protruding portion 414 and the receding portion 454 can be engaged (fitted together) relatively easily. For example, even if the inclined face 414b of the protruding portion 414 collides with an edge 452e of the protrusion 452, the protruding portion 414 can easily ride over the edge 452e.

Figure 17B:
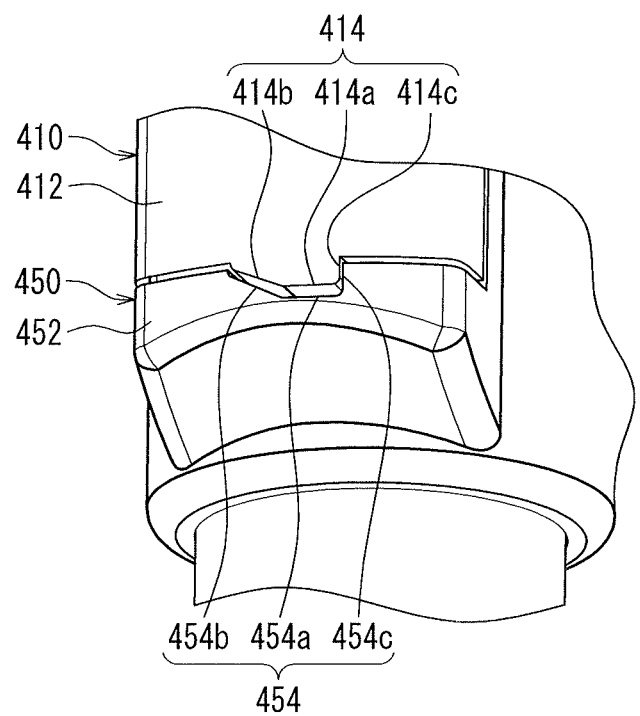
FIG. 17B is a perspective diagram showing a state in which the protruding portion and the receding portion shown in FIG. 17A are fitted together.

FIG. 17B is a perspective diagram showing a state in which the connector body 410 and the lock nut 450 have been connected, and the protruding portion 414 and the receding portion 454 have been engaged (fitted together). The top face 414a, the inclined face 414b, and the vertical face 414c of the protruding portion 414 respectively oppose the bottom face 454a, the inclined face 454b, and the vertical face 454c of the receding portion 454. The vertical face 414c and the vertical face 454c oppose each other in the circumferential direction, and therefore a relatively large amount of force is needed in order to release the engagement (fitting together) of the protruding portion 414 and the receding portion 454.

Due to the first rotation prevention mechanisms being constituted by the protruding portion 414 and the receding portion 454 that are asymmetrical in the circumferential direction in this way, the male connector 4 of Embodiment 4 makes assembly relatively easy and makes disassembly relatively difficult. Accordingly, it is possible to reduce the possibility of the connector body 410 and the lock nut 450 becoming separated unintentionally.

In FIGS. 17A and 17B, the faces that constitute the protruding portion 414 and the receding portion 454 do not need to be flat faces, and may be curved faces. A configuration is possible in which the protruding portion 414 and the receding portion 454 are not provided with the top face 414a and the bottom face 454a, and instead are respectively a triangular protruding portion in which the inclined face 414b and the vertical face 414c are adjacent to each other, and a triangular receding portion in which the inclined face 454b and the vertical face 454c are adjacent to each other. The vertical faces 414c and 414c may be changed to inclined faces that are inclined relative to the horizontal direction.

As can be easily understood by comparing the male connector 4 (FIG. 13A) of Embodiment 4 with the male connector 1 (FIG. 1A) of Embodiment 1, the pair of extension portions 412 extend to the vicinity of the lower end of the lock nut 450 in Embodiment 4. The vertical dimension of the protrusions 452 is much smaller than that of the extension portions 412. This configuration is advantageous to reducing the possibility that the patient or the like makes an operation mistake such as a mistaken disassembly to the connector body 410 and the lock nut 450. On the other hand, there is a possibility of somewhat reducing the operability of the connection/separation of the connector body 410 and the lock nut 450 when cleaning the male connector 4, for example. In response to this, it is possible to compensate for this reduction in operability by using a jig that engages with the pair of protrusions 452, for example. The following describes an example of such a jig.

Figure 18A:
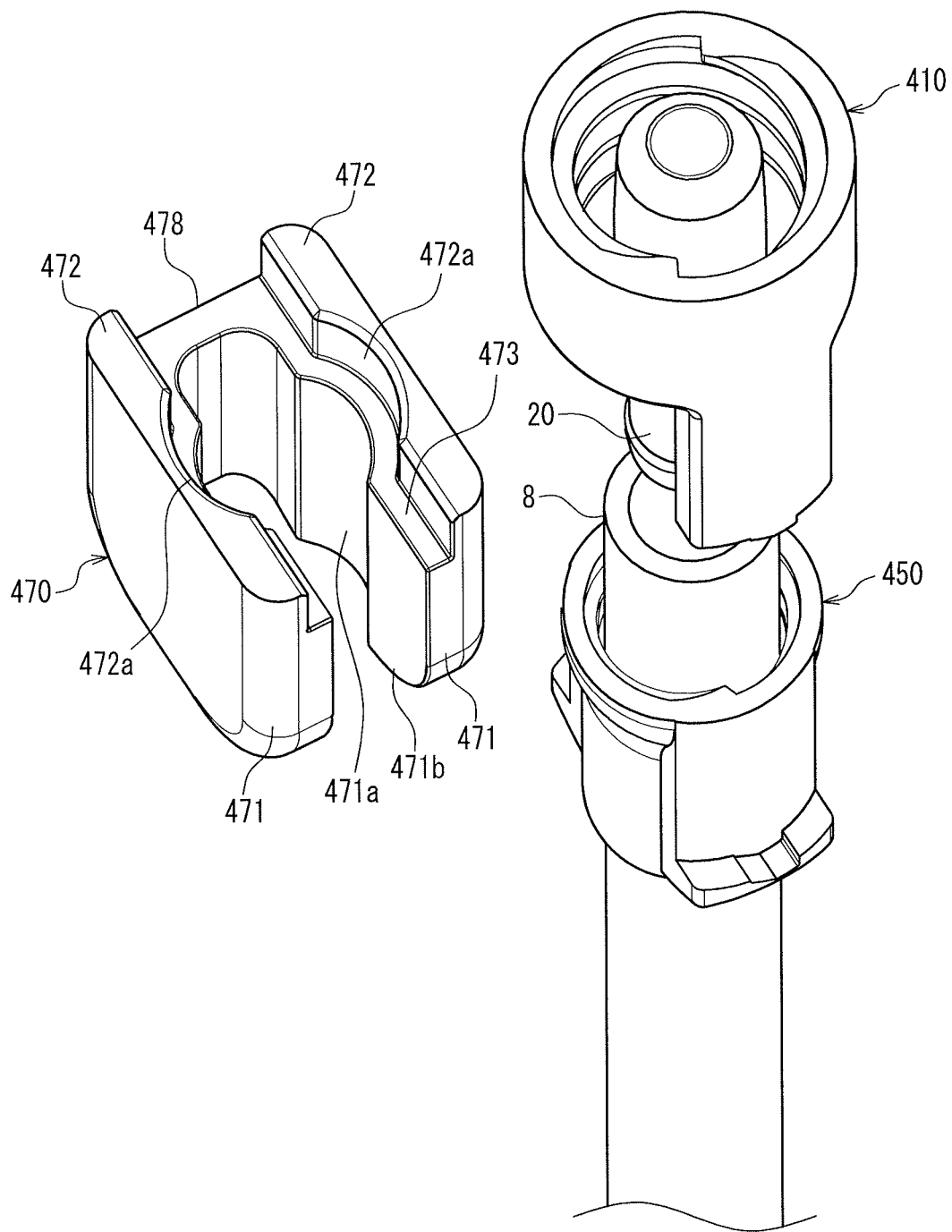
FIG. 18A is a perspective diagram showing one step in a method for assembling the male connector according to Embodiment 4 of the present invention using a jig.

FIG. 18A is an exploded perspective diagram showing a state immediately before the connector body 410 and the lock nut 450 are connected using a jig 470. The jig 470 approximately has a "U" shape when viewed from above, in which a pair of gripping plates 471 that oppose each other are connected by a connection portion 478. Restriction portions 472 protrude upward from outward portions (portions distant from the opposing gripping plates 471) of the upper faces of the pair of gripping plates 471. Relatively lower portions inward of the restriction portions 472 are holding portions 473.

First receding portions 471a are formed on mutually opposing faces 471b of the pair of gripping plates 471 that are below the holding portions 473, and second receding portions 472a are formed on mutually opposing faces of the pair of restriction portions 472. The mutually opposing first receding portions 471a formed on the faces 471b constitute portions of a common cylindrical face, and the mutually opposing second receding portions 472a formed on the restriction portions 472 also constitute portions of a common cylindrical face. The cylindrical face of the first receding portions 471a and the cylindrical face of the second receding portions 472a are coaxial.

The following describes a method of connecting the connector body 410 and the lock nut 450 using the jig 470 described above.

As shown in FIG. 18A, the tube 8 is inserted into the lock nut 450. The open side of the jig 470 (the side opposite to the connection portion 478) is arranged so as to oppose the tube 8.

Figure 18B:
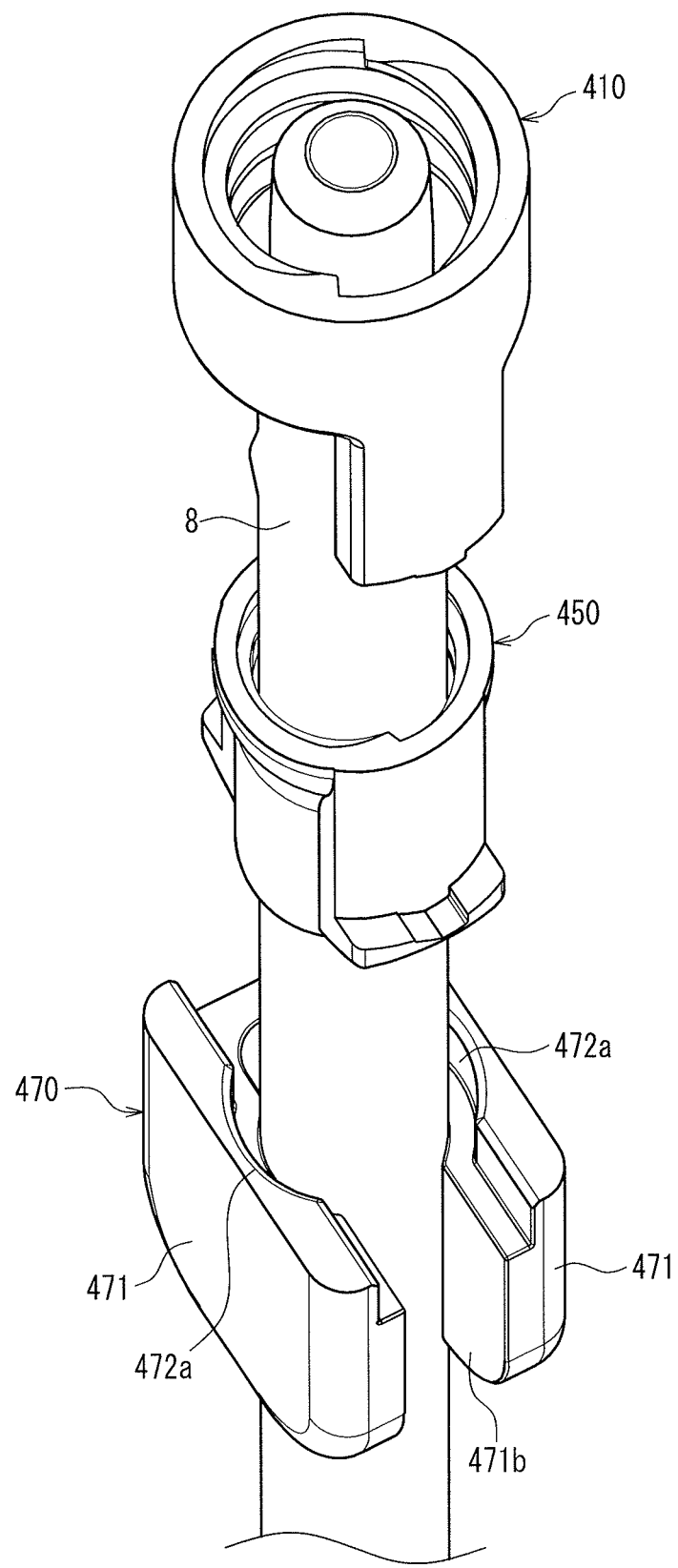
FIG. 18B is a perspective diagram showing one step in a method for assembling the male connector according to Embodiment 4 of the present invention using a jig.

Next, as shown in FIG. 18B, the base end portion 20 of the connector body 410 is inserted into the tube 8. Then, the tube 8 is inserted between the pair of gripping plates 471 of the jig 470 below the lock nut 450. The outer diameter of the tube 8 is larger than the gap between the mutually opposing faces 471b of the gripping plates 471, and is the same as or slightly smaller than the diameter of the cylindrical face formed by the mutually opposing first receding portions 471a (see FIG. 18A). Accordingly, the tube 8 undergoes deformation so as to decrease in diameter when passing between the mutually opposing faces 471b. Then, when the tube 8 is fitted between the mutually opposing first receding portions 471a as shown in FIG. 18B, it returns to its initial state.

Figure 18C:
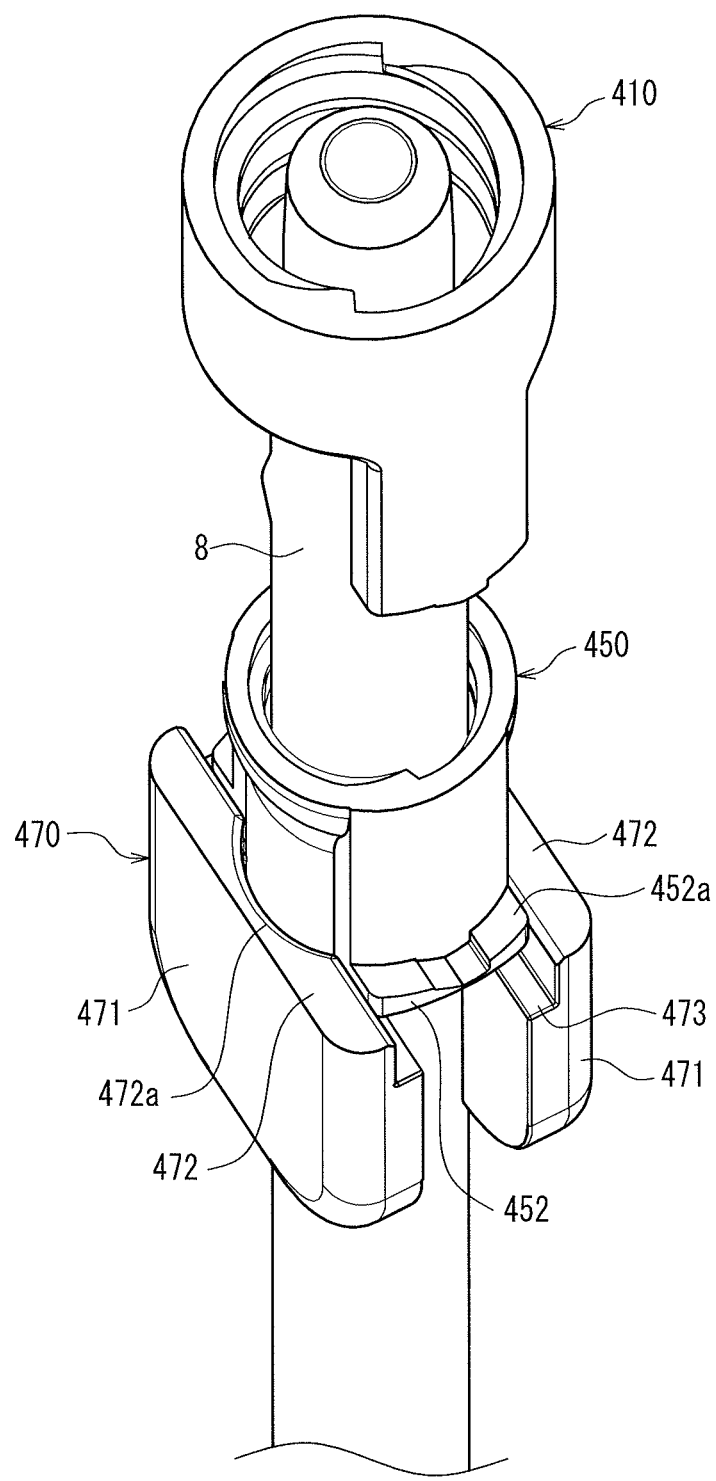
FIG. 18C is a perspective diagram showing one step in a method for assembling the male connector according to Embodiment 4 of the present invention using a jig.

Subsequently, while the tube 8 has been fitted between the mutually opposing first receding portions 471a, the jig 470 is raised. The outer diameter of the lower end portion of the lock nut 450 is larger than the diameter of the cylindrical face formed by the mutually opposing first receding portions 471a, and the same as or slightly smaller than the diameter of the cylindrical face formed by the mutually opposing second receding portions 472a. Accordingly, as shown in FIG. 18C, the lower end portion of the lock nut 450 is fitted between the mutually opposing second receding portions 472a, and is in contact with the holding portions 473. The pair of protrusions 452 of the lock nut 450 are fitted between the pair of restriction portions 472. The upper faces 452a of the protrusion 452 are at a location that is the same as or higher than the upper ends of the restriction portions 472. The lock nut 450 is restricted from moving downward relative to the jig 470, and is restricted from rotating relative to the jig 470.

Figure 18D:
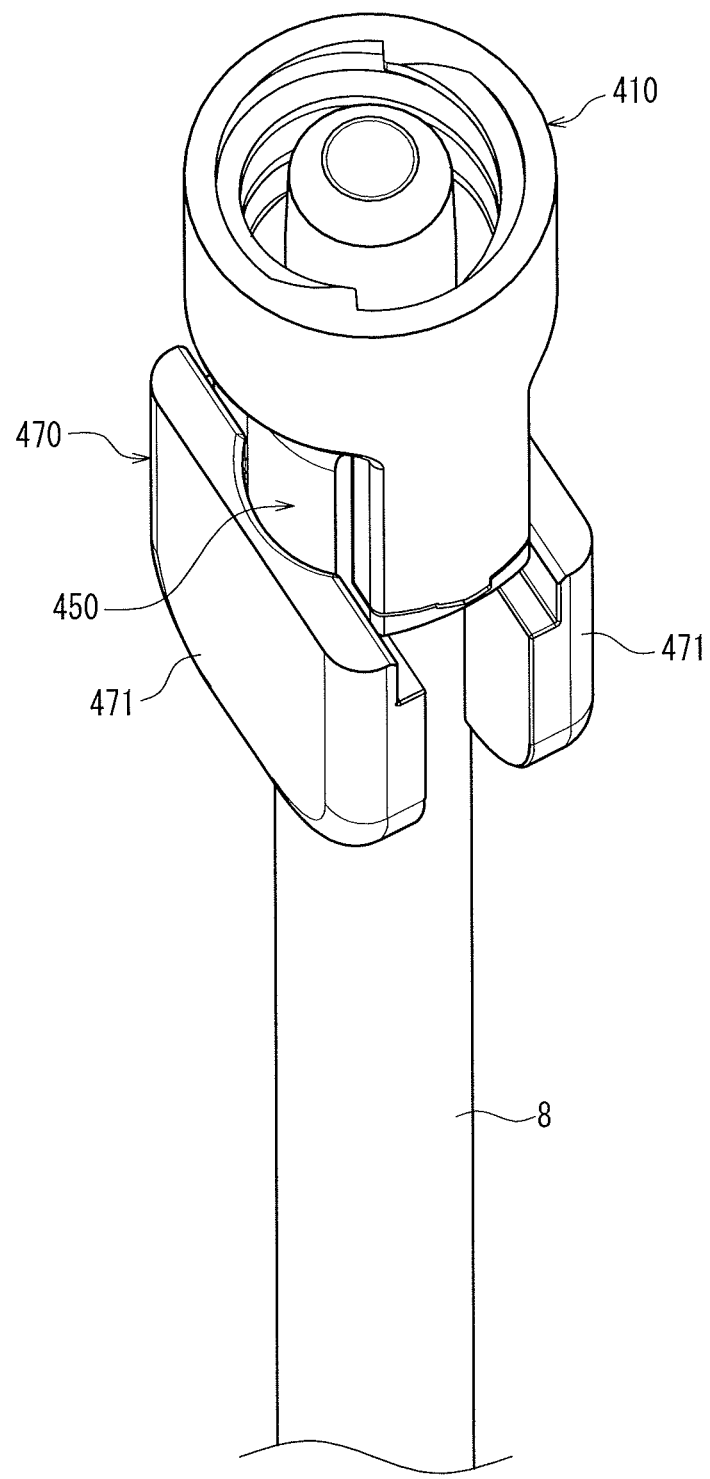
FIG. 18D is a perspective diagram showing one step in a method for assembling the male connector according to Embodiment 4 of the present invention using a jig.

In this state, the lock nut 450 is moved toward the connector body 410. Similarly to the above description, the lock nut 450 is rotated relative to the connector body 410 so as to connect the lock nut 450 to the connector body 410 as shown in FIG. 18D.

The separation of the connector body 410 and the lock nut 450 can be performed by performing the above-described operations in reverse.

When attachment and separation have respectively ended, the jig 470 is separated from the tube 8.

As described above, the jig 470 restricts vertical movement and rotation of the lock nut 450. Accordingly, the lock nut 450 can be held via the jig 470 so as to not fall, and rotation torque can be applied to the lock nut 450 via the jig 470. For this reason, by holding the lock nut 450 via the pair of gripping plates 471 of the jig 470, the lock nut 450 can be easily attached to and separated from the connector body 410.

The gap between the mutually opposing faces 471b of the pair of gripping plates 471 is smaller than the outer diameter of the tube 8, and therefore once the tube 8 has been inserted between the first receding portions 471a (see FIG. 18B), even if the jig 470 is let go, the jig 470 does not fall away from the tube 8. Accordingly, the operability of attachment and separation improves.

The shape of the jig 470 is not limited to the above-described example. For example, receding portions into which the protrusions 452 are fitted may be formed in the upper faces of the pair of gripping plates 471. In this case, falling and rotation of the lock nut 450 are restricted by fitting the pair of protrusions 452 to the pair of gripping plates 471.

Embodiment 4 has effects similar to those of Embodiment 1 with the exception of the content described above.

Embodiment 4 is the same as Embodiment 1 with the exception of the content described above. The description of Embodiment 1 applies to Embodiment 4 as well.

Embodiment 5

Configuration

A male connector 5 of Embodiment 5 has mainly the following two differences from the male connector 4 of Embodiment 4. Firstly, a fixed protrusion is not formed on the base end portion that is inserted into the tube 8. Secondly, the configuration of the first rotation prevention mechanisms is different. The male connector 5 of Embodiment 5 will be described with focus on differences from the male connector 4 of Embodiment 4. In the drawings referenced below, elements the same as or corresponding to elements of the male connector 4 of Embodiment 4 are denoted by the same reference signs, and detailed descriptions will not be given for them.

Figure 19A:
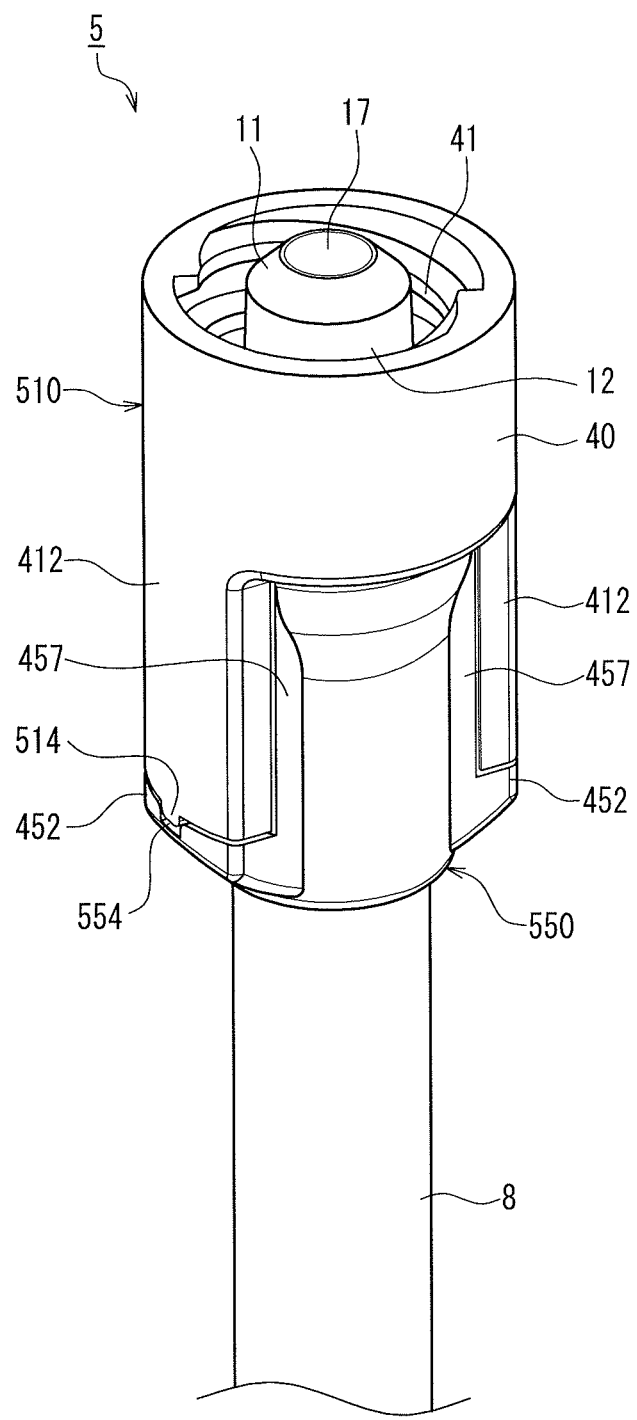
FIG. 19A is a perspective view of a male connector according to Embodiment 5 of the present invention.
Figure 19B:
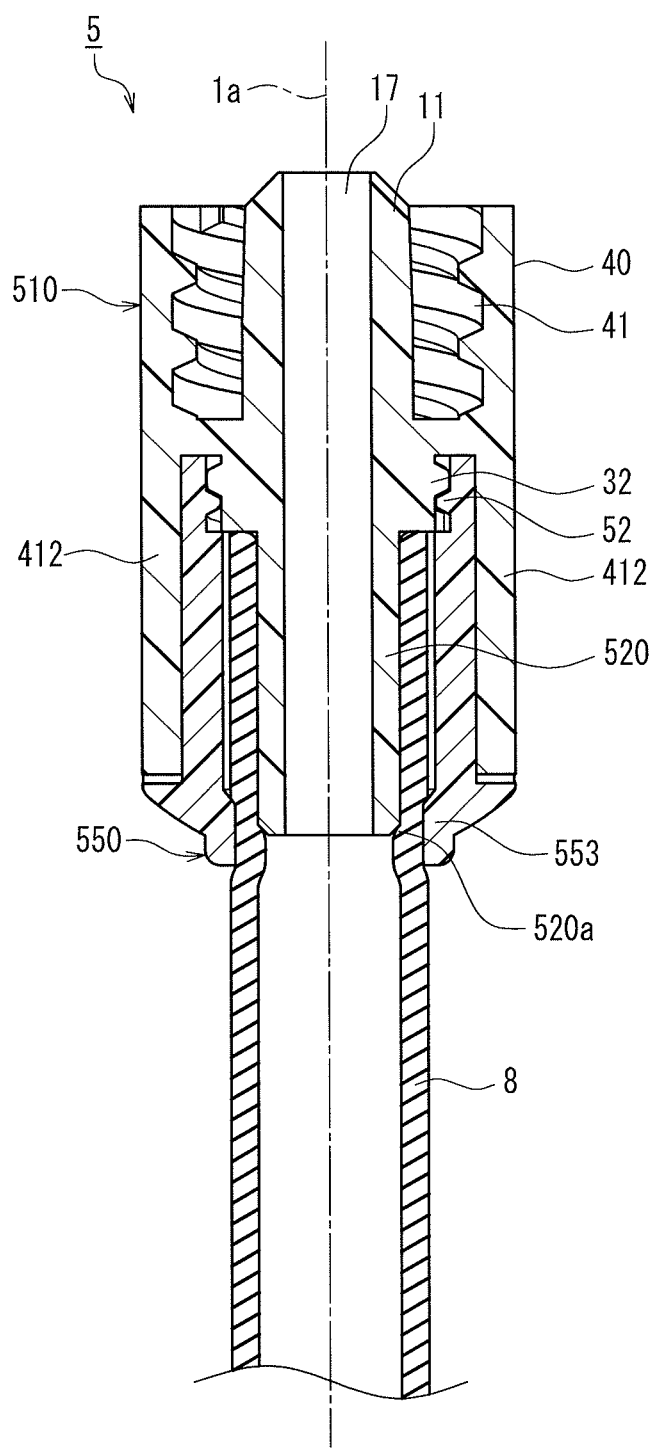
FIG. 19B is a cross-sectional view taken along a plane that includes the central axis of the male connector according to Embodiment 5 of the present invention.
Figure 19C:
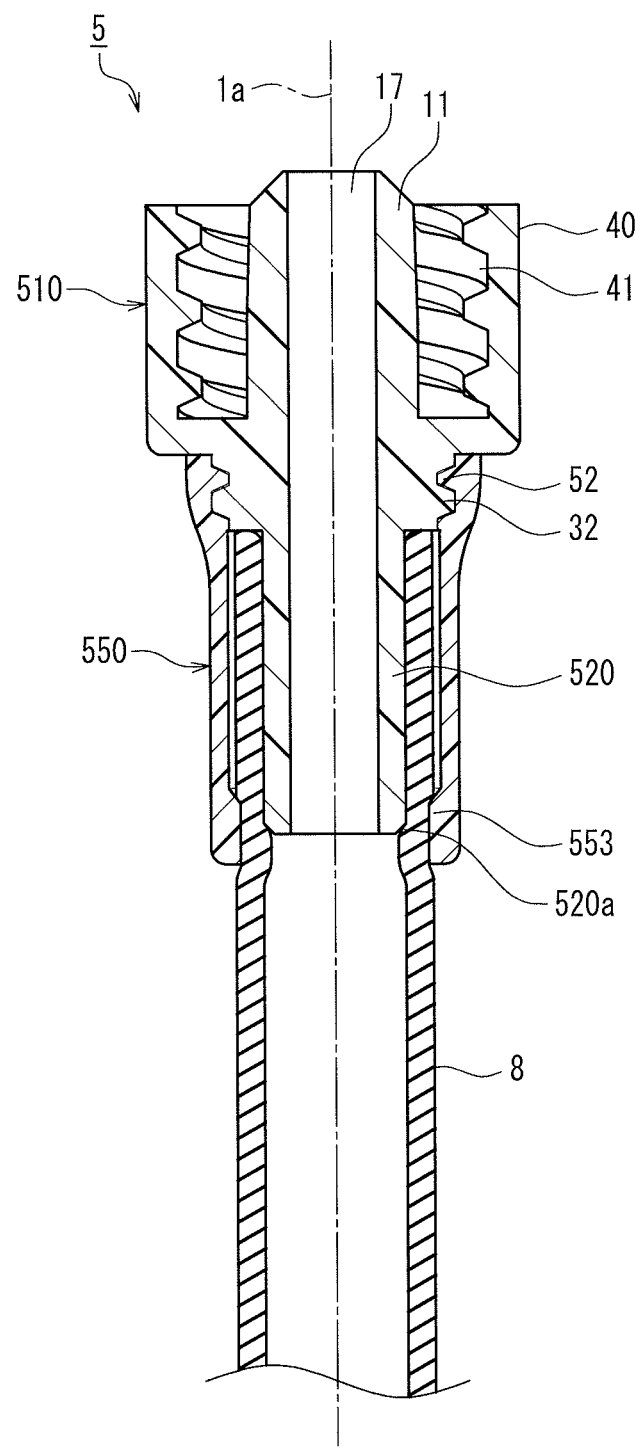
FIG. 19C is a cross-sectional view taken along a different plane that includes the central axis of the male connector according to Embodiment 5 of the present invention.

FIG. 19A is a perspective view of the male connector 5 according to Embodiment 5 of the present invention. FIG. 19B is a cross-sectional view taken along a plane that includes the central axis 1a and the extension portions 412 of the male connector 5. FIG. 19C is a cross-sectional view taken along a different plane that includes the central axis 1a of the male connector 5. The cross-section in FIG. 19C is orthogonal to the cross-section in FIG. 19B. Similarly to the male connector 4 of Embodiment 4, the male connector 5 of Embodiment 5 includes a connector body 510 and a lock nut 550.

Figure 20A:
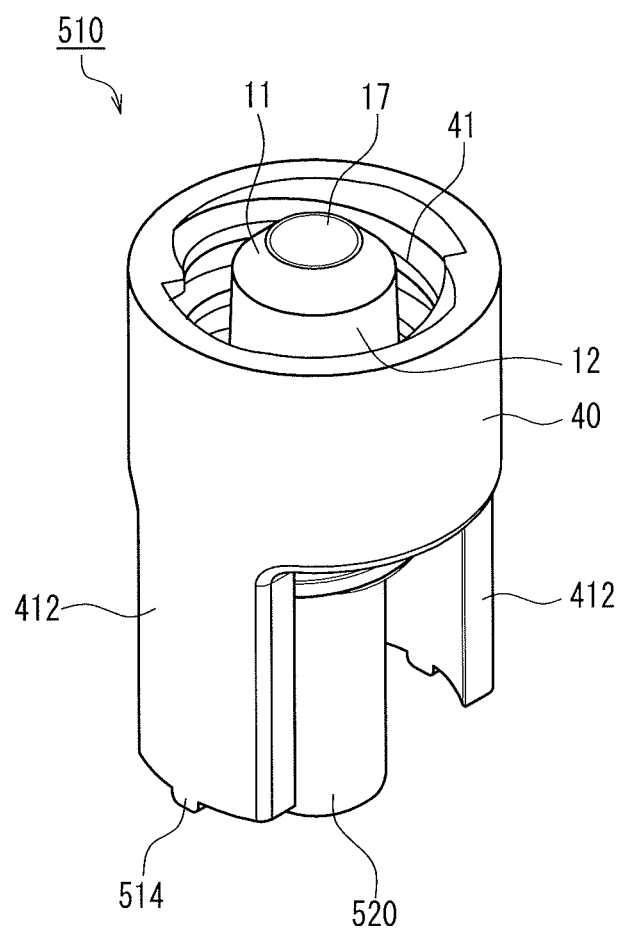
FIG. 20A is a perspective view of a connector body that constitutes the male connector according to Embodiment 5 of the present invention, as viewed from above.
Figure 20B:
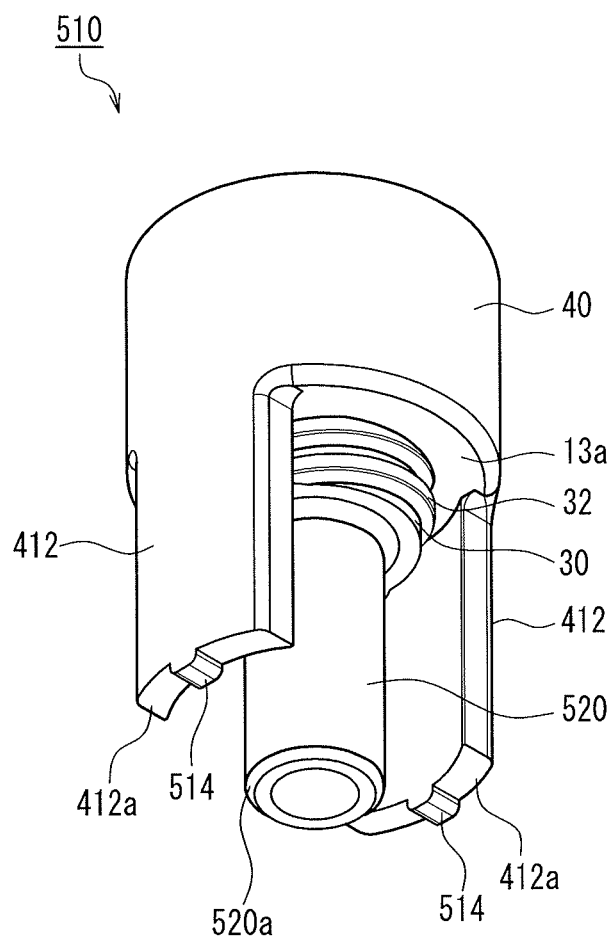
FIG. 20B is a perspective view of the connector body that constitutes the male connector according to Embodiment 5 of the present invention, as viewed from below.
Figure 20C:
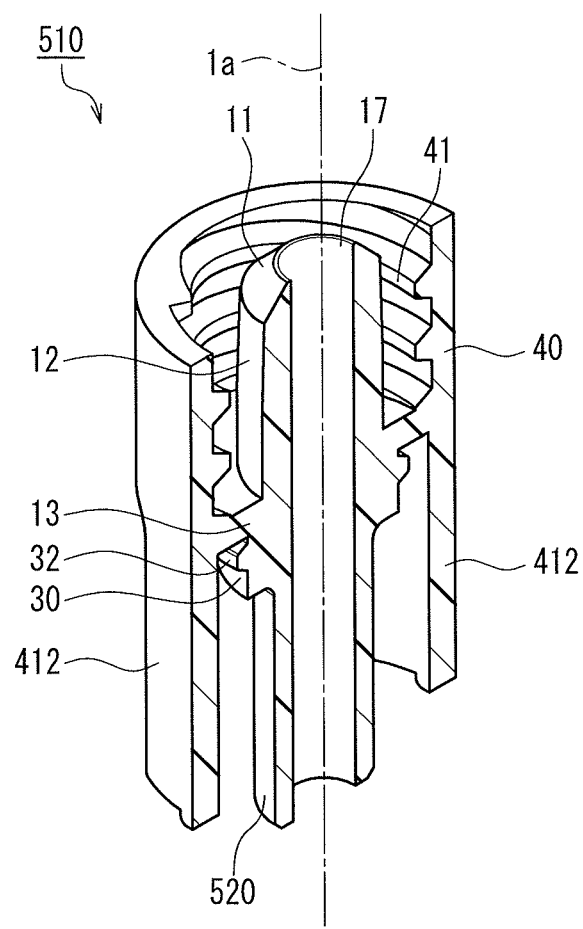
FIG. 20C is a perspective cross-sectional view of the connector body that constitutes the male connector according to Embodiment 5 of the present invention.

FIG. 20A is a perspective view of the connector body 510 as viewed from above, FIG. 20B is a perspective view of the connector body 510 as viewed from below, and FIG. 20C is a perspective cross-sectional view of the connector body 510 taken along a plane that includes the central axis 1a.

As shown most clearly in FIG. 20B, a base end portion 520 extends downward from the tubular portion 30. The base end portion 520 does not include the fixed protrusion 21 that is included in the connector bodies 10, 210, 310, and 410 of Embodiments 1 to 4. The outer circumferential face of the base end portion 520 is a cylindrical face that is coaxial with the central axis 1a. It is preferable that the outer diameter of the base end portion 520 is approximately the same as the inner diameter of the tube 8.

Similarly to the connector body 410 of Embodiment 4, the pair of extension portions 412 extend downward from the outer circumferential edge of the disc-shaped flange 13. Lower faces 412a of the extension portions 412 are flat surfaces that are perpendicular to the central axis 1a. Protruding portions 514 protrude downward from the lower faces 412a of the extension portions 412. The shape of the protruding portions 514 is different from that of the protruding portions 414 of Embodiment 4. When viewed along the radial direction, the protruding portions 514 have an approximately rectangular shape. The pair of protruding portions 514 are in rotation symmetry (two-fold symmetry) about the central axis 1a.

Figure 21A:
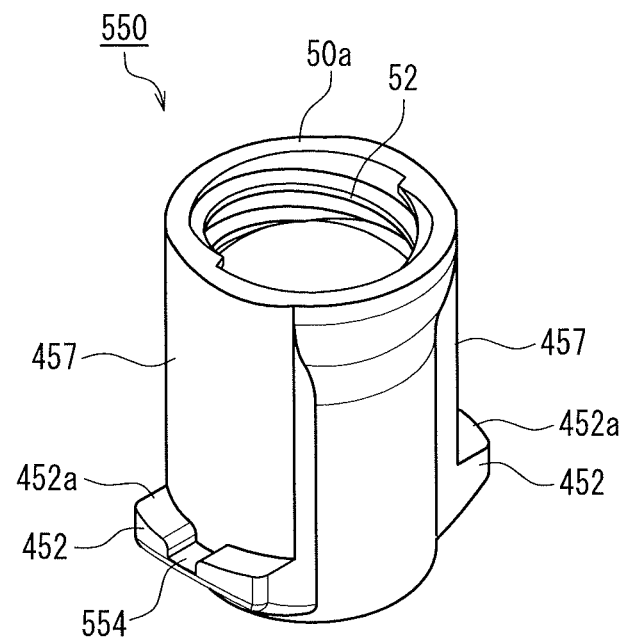
FIG. 21A is a perspective view of a lock nut that constitutes the male connector according to Embodiment 5 of the present invention, as viewed from above.
Figure 21B:
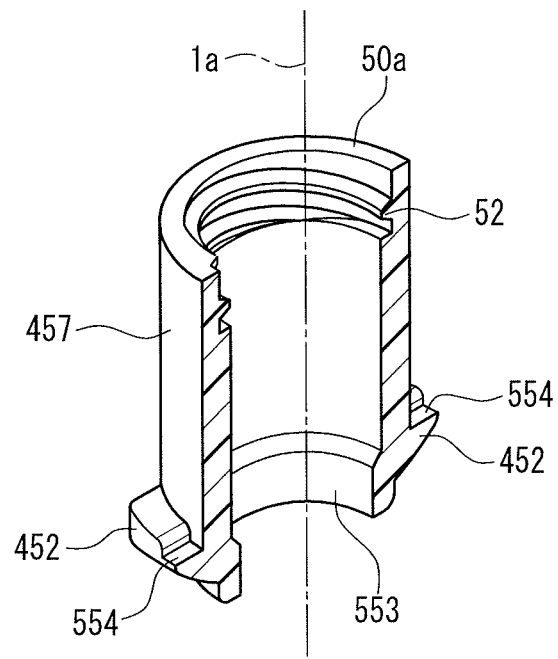
FIG. 21B is a perspective cross-sectional view of the lock nut that constitutes the male connector according to Embodiment 5 of the present invention.

FIG. 21A is a perspective view of the lock nut 550 as viewed from above, and FIG. 21B is a perspective cross-sectional view of the lock nut 550.

As shown most clearly in FIG. 21B, the lock nut 550 has a small diameter portion 553 in the vicinity of the lower end of the inner circumferential face. The inner diameter of the small diameter portion 553 is smaller than the inner diameters of any of the portions of the lock nut 550 located above, and is slightly larger than the outer diameter of the base end portion 520 (FIGS. 20A and 20B) of the connector body 510. The inner circumferential face of the small diameter portion 553 is a cylindrical face whose inner diameter is constant in the central axis 1a direction.

As shown in FIG. 21A, the pair of protrusions 452 protrude outward along the radial direction from the outer circumferential face of the lock nut 550. The protrusions 452 extend along the circumferential direction. Upper faces 452a of the protrusions 452 are flat surfaces that are perpendicular to the central axis 1a. Receding portions 554 are formed in the upper faces 452a of the protrusions 452. The shape of the receding portions 554 is different from that of the receding portions 454 of Embodiment 4. When viewed along the radial direction, the receding portions 554 have an approximately rectangular shape. The pair of receding portions 554 are in rotation symmetry (two-fold symmetry) about the central axis 1a.

The configuration of the male connector 5 is the same as the male connector 4 of Embodiment 4 with the exception of the content described above.

Attachment to and Detachment from Tube

The male connector 5, which has the above-described configuration and is constituted by the connector body 510 and the lock nut 550, is removably attached to the upstream end of the tube 8 (FIGS. 19A to 19C).

The male connector 5 is attached to the tube 8 as follows.

Figure 22A:
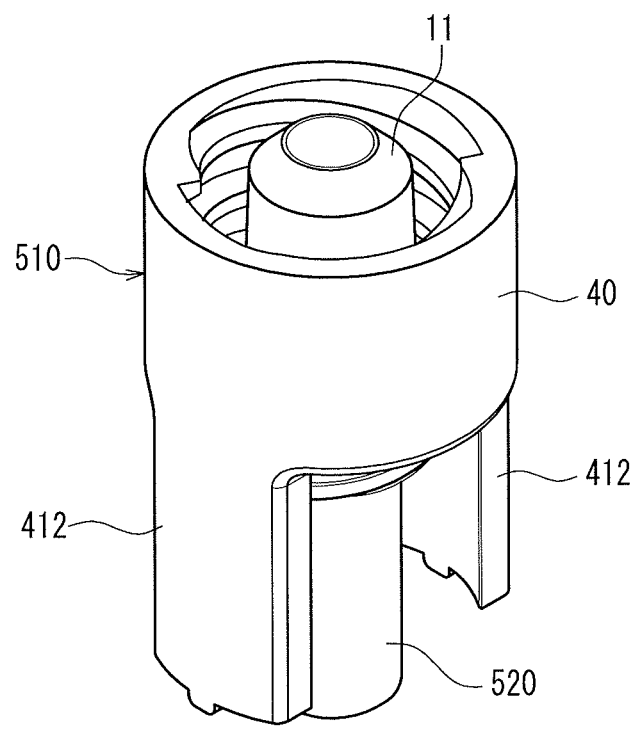
FIG. 22A is a perspective diagram showing one step for attaching the male connector according to Embodiment 5 of the present invention to a tube.
Figure 22A:
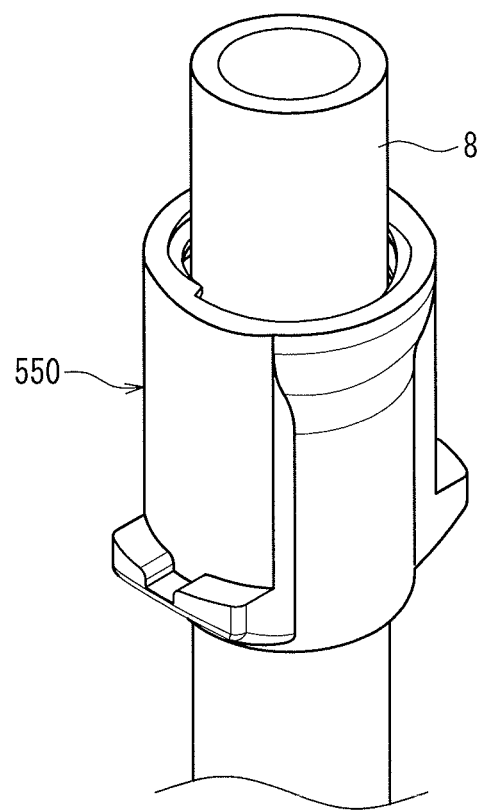

First, as shown in FIG. 22A, the tube 8 is inserted into the lock nut 550. The connector body 510 is then arranged so as to oppose the upstream end of the tube 8.

Figure 22B:
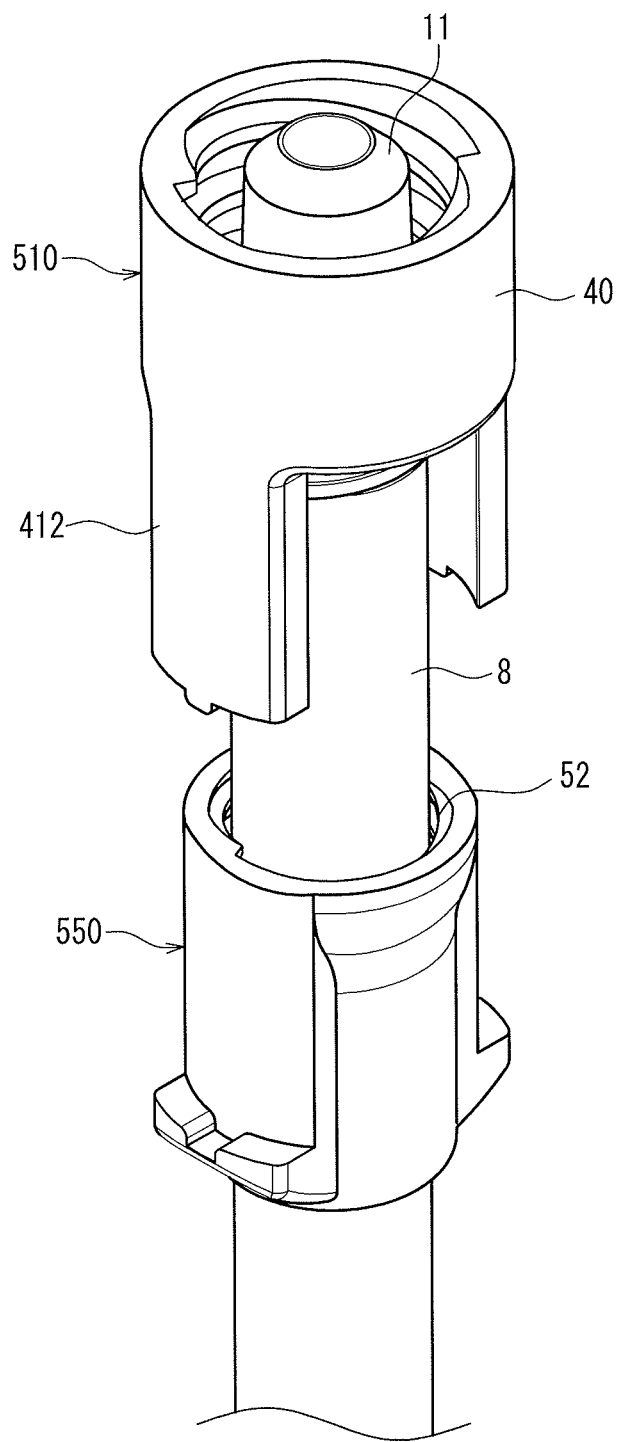
FIG. 22B is a perspective diagram showing one step for attaching the male connector according to Embodiment 5 of the present invention to a tube.

Next, as shown in FIG. 22B, the base end portion 520 of the connector body 510 is inserted into the tube 8.

Figure 22C:
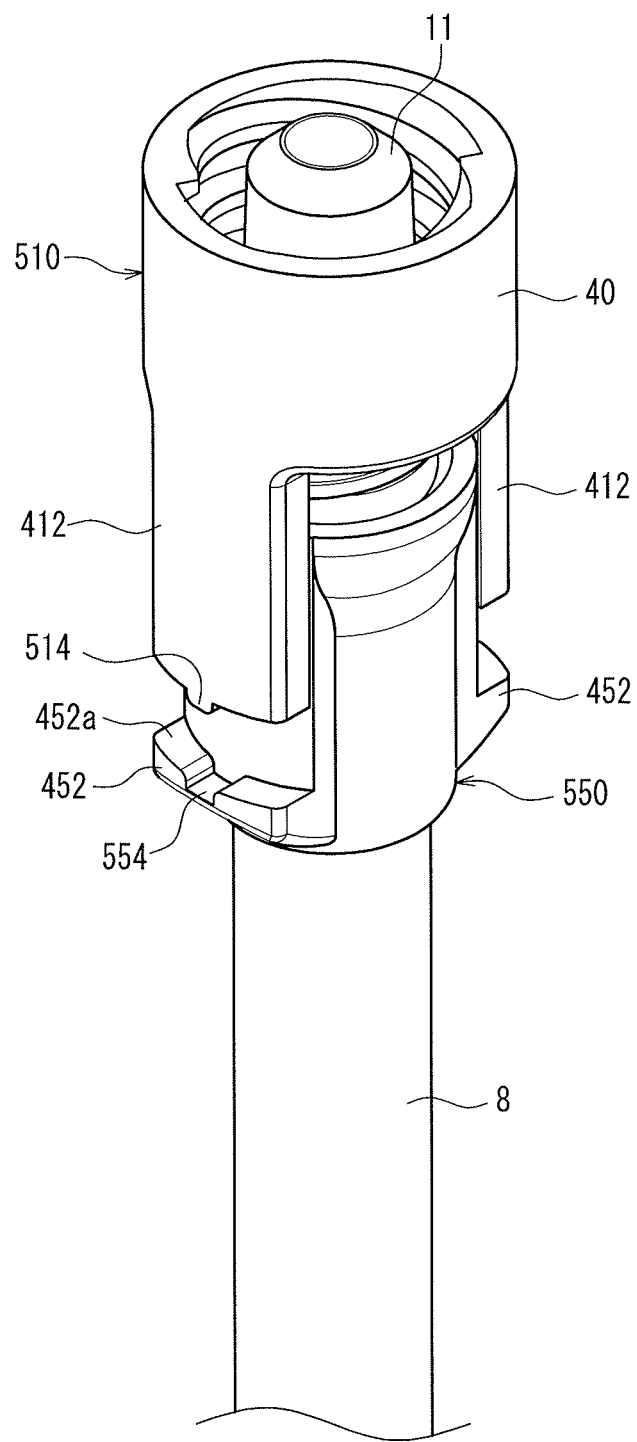
FIG. 22C is a perspective diagram showing one step for attaching the male connector according to Embodiment 5 of the present invention to a tube.

Next, as shown in FIG. 22C, the lock nut 550 is moved toward the connector body 510. The lock nut 550 is inserted between the pair of extension portions 412. The lock nut 550 is rotated relative to the connector body 510, thus screwing the spiral protrusion 32 (FIG. 20B) and the female threading 52 (FIG. 21A) together. The lock nut 550 approaches the outer tube 40 of the connector body 510. The protruding portions 514 of the extension portions 412 soon come into contact with the upper faces 452a of the protrusions 452, and slide thereon. Finally, the protruding portions 514 are fitted into the receding portions 554, and, at the same time, the lower faces 412a of the extension portions 412 and the upper faces 452a of the protrusions 452 oppose each other. When the pair of protruding portions 514 are fitted into the pair of receding portions 554, the rotation torque for rotating the lock nut 550 changes, and the operator can feel that change as a clicking sensation through their fingers.

Thus, the male connector 5 is attached to the upstream end of the tube 8 as shown in FIGS. 19A to 19C.

As shown in FIG. 19A, the protruding portions 514 are fitted into the receding portions 554.

As shown in FIGS. 19B and 19C, the lower end 520a of the outer circumferential face of the base end portion 520 and the small diameter portion 553 oppose each other and clamp the tube 8 while compressing it in the radial direction.

The male connector 5 that is attached to the tube 8 as shown in FIGS. 19A to 19C is removed from the tube 8 as follows.

First, the lock nut 550 is rotated relative to the connector body 510, in the direction opposite to that during attachment. In order to begin rotation, the protruding portions 514 and the receding portions 554 need to be disengaged, and a somewhat large amount of rotation torque needs to be applied for disengagement. After the protruding portions 514 have escaped the receding portions 554, the lock nut 550 can be rotated relative to the connector body 510 with a small rotation torque.

After the lock nut 550 has been separated from the connector body 510 as shown in FIG. 22B, the connector body 510 is pulled out from the tube 8 (FIG. 22A). Thereafter, the tube 8 is pulled out from the lock nut 550.

When the connector body 510 and the lock nut 550 are rotated in opposite directions, the outer tube 40 is pinched with one hand, and the pair of protrusions 452 are pinched with the other hand.

The male connector 5 can be repeatedly attached to and detached from the tube 8 any number of times.

Method of Use

The method of use of the male connector 5 is approximately the same as the method of use of the male connector 4 of Embodiment 4. Similarly to Embodiment 4, it is possible to connect the female connector 920 compliant with ISO 80369-3 (FIGS. 25A and 25B) to the male connector 5, perform enteral feeding, and thereafter separate the female connector 920 from the male connector 5. The connection between the male connector 5 and the female connector 920 is excellent in terms of liquid-tightness and connection strength, similarly to the connection between the male connector 910 (FIGS. 24A and 24B) and the female connector 920.

Similarly to Embodiment 4, after enteral feeding has been performed, it is possible to remove the male connector 5 from the tube 8 and clean the connector body 510 and the lock nut 550 by washing them with water separately. The cleaned connector body 510 and lock nut 550 are then attached to the tube 8 again. Either or both of the connector body 510 and the lock nut 550 may be replaced with new ones instead of being cleaned.

Similarly to Embodiment 4, in the case of installing a gastrostomy, the tube 8 is fixed to the patient, and then the male connector 5 is attached to the tip of the tube 8 that has been pulled out from the patient.

Effects

In Embodiment, the fixed protrusion 21 included in the connector bodies 10, 210, 310, and 410 of Embodiments 1 to 4 is not included on the base end portion 520 of the connector body 510. However, in Embodiment 5, after the base end portion 520 has been inserted into the tube 8, when the spiral protrusion 32 of the connector body 510 and the female threading (second female threading) 52 of the lock nut 550 are screwed together, the lower end 520a of the base end portion 520 of the connector body 510 and the small diameter portion 553 of the lock nut 550 can clamp the tube 8 in the radial direction. The tube 8 is locally compressed by the lower end 520a of the base end portion 520 and the inner circumferential face of the small diameter portion 553. Accordingly, the male connector 5 can be firmly attached to the tube 8, similarly to Embodiments 1 to 4. An enteral nutrient does not leak from the joining portion of the male connector 5 and the tube 8 due to pressure applied to the enteral nutrient flowing through the channel 17 and the tube 8, and the male connector 5 and the tube 8 do not unintentionally become separated due to tensile force acting on the tube 8.

Not providing the fixed protrusion 21 on the base end portion 520 has advantages such as the following. Firstly, in the case where the connector body 510 is molded from resin, the connector body 510 can be easily separated from the die. Secondly, the base end portion 520 can be easily inserted into and pulled out from the tube 8, and therefore the male connector 5 can be easily attached to and detached from the tube 8.

The shapes of the lower end 520a of the outer circumferential face of the base end portion 520 and the inner circumferential face of the small diameter portion 553 can be changed arbitrarily. For example, a tapered face whose outer diameter decreases as it extends away from the tubular portion 30 (male tapered face) may be formed on the lower end 520a of the outer circumferential face of the base end portion 520. Also, the inner circumferential face of the small diameter portion 553 may be a tapered face whose inner diameter decreases as it extends downward (female tapered face). In this way, even if a tapered face is formed on either or both of the base end portion 520 and the small diameter portion 553, the tube 8 can be clamped between the base end portion 520 and the small diameter portion 553, and therefore the male connector 5 can be firmly attached to the tube 8.

Similarly to Embodiment 4, in Embodiment 5 as well, by engaging with each other (fitting together), the pair of protruding portions 514 of the connector body 510 and the pair of receding portions 554 of the lock nut 550 constitute first rotation prevention mechanisms for preventing the lock nut 550 from rotating relative to the connector body 510.

Figure 23A:
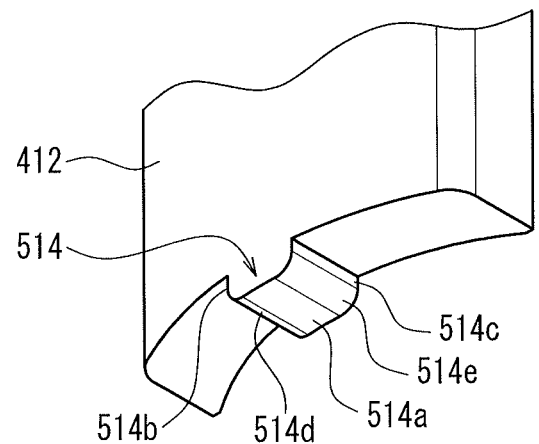
FIG. 23A is an enlarged perspective diagram showing a protruding portion that constitutes a first rotation prevention mechanism of the male connector according to Embodiment 5 of the present invention.

FIG. 23A is an enlarged perspective view of a protruding portion 514. The protruding portion 514 includes a top face (most protruding face) 514a that is parallel with the horizontal direction, and vertical faces 514b and 514c that are parallel with the up-down direction on respective sides of the top face 514a. Chamfered faces 514d and 514e, which are shaped as cylindrical faces, are formed between the top face 514a and the vertical faces 514b and 514c respectively.

Figure 23B:
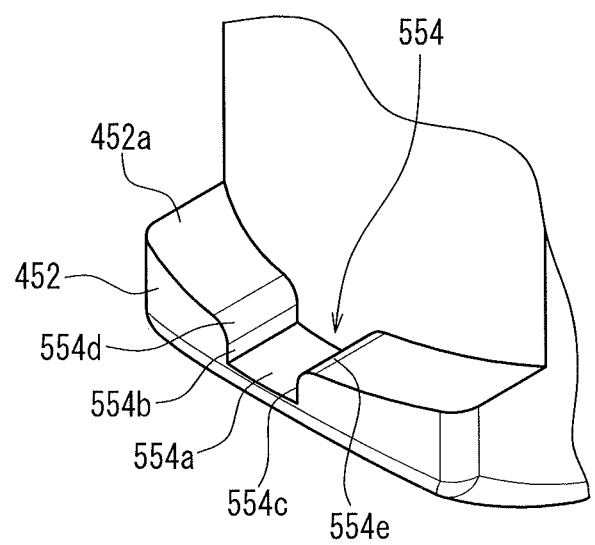
FIG. 23B is an enlarged perspective diagram showing a receding portion that constitutes a first rotation prevention mechanism of the male connector according to Embodiment 5 of the present invention.

FIG. 23B is an enlarged perspective view of a receding portion 554. The receding portion 554 includes a bottom face 554a that is parallel with the horizontal direction, and vertical faces 554b and 554c that are parallel with the up-down direction on respective sides of the bottom face 554a. Chamfered faces 554d and 554e, which are shaped as cylindrical faces, are formed between the upper face 452a of the protrusion 452 and the vertical faces 554b and 554c respectively.

When the protruding portion 514 and the receding portion 554 engage (are fitted together) (FIG. 19A), the top face 514a and the vertical faces 514b and 514c of the protruding portion 514 respectively oppose the bottom face 554a and the vertical faces 554b and 554c of the receding portion 554.

Similarly to Embodiment 4, the large amount of rotation torque necessary for loosening the screwing together of the first female threading 41 and the male threading 926 is not transmitted via the first rotation prevention mechanisms of Embodiment 5. The first rotation prevention mechanisms need only be able to prevent the screwing together of the spiral protrusion 32 and the second female threading 52 from becoming loosened unintentionally. In view of this, the relatively large chamfered faces 514d and 514e are formed on the protruding portions 514, and the relatively large chamfered faces 554d and 554e are formed on the receding portions 554 as well. Accordingly, there is an improvement in the operability of the connection/separation of the connector body 510 and the lock nut 550. Also, it is possible to reduce the wearing of and damage to the protruding portions 514 and the receding portions 554 when connection/separation is performed repeatedly.

The top face 514a and the vertical faces 514b and 514c of the protruding portion 514 and the bottom face 554a and the vertical faces 554b and 554c of the receding portion 554 in FIGS. 23A and 23B do not need to be flat faces, and may be curved faces. A configuration is possible in which the protruding portion 514 is not provided with the top face 514a, and instead is a protruding portion that includes a top portion that is a cylindrical face in which the chamfered face 514d and the chamfered face 514e are adjacent to each other. The vertical faces 514b and 554b and/or the vertical faces 514c and 554c may be changed to inclined faces that are inclined relative to the horizontal direction. The chamfered faces 514d and 514e and the chamfered faces 554d and 554e do not need to be cylindrical faces, and may be arbitrary curved faces, inclined faces that are inclined relative to the horizontal direction, a combination thereof, or the like.

Embodiment 5 has effects similar to those of Embodiment 4 with the exception of the content described above.

Embodiment 5 is the same as Embodiment 4 with the exception of the content described above. The description of Embodiment 4 applies to Embodiment 5 as well.

Embodiments 1 to 5 described above are merely illustrative examples. The present invention is not limited to Embodiments 1 to 5 described above, and can be modified as necessary.

A protrusion may be provided on the connector body 10, 210, 410, 510 and the lock portion 340 as well so as to enable firmly gripping and applying rotation torque to the connector body 10, 210, 410, 510 in Embodiment 1, 2, 4, 5 and the lock portion 340 in Embodiment 3. There are no limitations on the shape of the protrusion, and, for example, one or more ridge-shaped protrusions that are similar to the ribs 57 provided on the lock nut 50 can be provided on the outer circumferential face of the outer tube 40 (Embodiment 1, 2, 4, 5) and the outer circumferential face of the lock portion 340 (Embodiment 3) so as to extend along a plane that includes the central axis 1a.

Alternatively, a protrusion (convex portion) or recession (concave portion) capable of engaging with a jig may be provided on the outer tube 40 and the lock portion 340. For example, multiple protrusions or multiple recessions can be provided on the upper face of the outer tube 40 and the lock portion 340 (face on the side connected to the female connector 920). Multiple receding portions or multiple protruding portions that engage with the aforementioned protrusions or recessions are provided on one face of a disc-shaped jig whose outer diameter is larger than the outer diameter of the outer tube 40 and the lock portion 340. In Embodiment 1, 2, 4, 5, when the lock nut 50, 250, 450, 550 is attached to and detached from the connector body 10, 210, 410, 510, the aforementioned jig is attached to the outer tube 40, and rotation torque is applied to the connector body 10, 210, 410, 510 via the jig. Accordingly, the operations of attachment and detachment of the lock nut 50, 250, 450, 550 are made easier. In Embodiment 3, when the lock portion 340 is attached to and detached from the luer portion 310, the aforementioned jig is attached to the lock portion 340, and rotation torque is applied to the lock portion 340 via the jig. Accordingly, the operations of attachment and detachment of the lock portion 340 are made easier.

The spiral protrusion 32, 332 may be either a discontinuous thread whose thread ridge is divided in the circumferential direction, or a continuous thread with a thread ridge that is continuous in the circumferential direction (i.e., general male threading).

The number of protruding portions 54, 326, 414, 514 and receding portions 14, 316, 454, 554 that constitute the rotation prevention mechanisms is not limited to being two, and may be one or a number greater than or equal to three. Which of the two opposing members is provided with the protruding portions and which is provided with the receding portions is not limited to the embodiments described above. In Embodiment 1, the protruding portions may be formed on the flange 13, and the receding portions may be formed on the lock nut 50. In Embodiment 3, the protruding portions may be formed on the flanges 13 and 313, and the receding portions may be formed on the lock nut 50 and the lock portion 340. In Embodiments 4 and 5, the protruding portions may be formed on the protrusions 452, and the receding portions may be formed on the extension portions 412.

The shapes of the protruding portions and the receding portions that constitute the rotation prevention mechanisms are not limited to the shapes in the above-described embodiments. For example, the protruding portions and the receding portion of Embodiments 1 and 3 may have shapes similar to the protruding portions 414 and the receding portions 454 of Embodiment 4, or may have shapes similar to the protruding portions 514 and the receding portions 554 of Embodiment 5. The protruding portions and the receding portions of Embodiment 4 may have shapes similar to the protruding portions 54 and the receding portions 14 of Embodiment 1, or may have shapes similar to the protruding portions 514 and the receding portions 554 of Embodiment 5. The protruding portions and the receding portions of Embodiment 5 may have shapes similar to the protruding portions 54 and the receding portions 14 of Embodiment 1, or may have shapes similar to the protruding portions 414 and the receding portions 454 of Embodiment 4.

The positions of the protruding portions and the receding portions that constitute the rotation prevention mechanisms are not limited to the positions in the above-described embodiments. For example, in Embodiment 4, 5, a configuration is possible in which either the protruding portions or the receding portions are formed on the lower face 13a of the flange 13, and the other ones are formed on the upper face 50a of the lock nut 450, 550. In this case, the rotation prevention mechanisms on the lower faces 412a of the extension portions 412 and the upper faces 452a of the protrusions 452 can be omitted.

The rotation prevention mechanisms that engage in the circumferential direction are not limited to being constituted by the protruding portions 54, 326, 414, 514 and the receding portions 14, 316, 454, 554. For example, they may be constituted by two protruding portions respectively formed on two faces that oppose each other. In this case, the two protruding portions engage with each other by one of the protruding portions riding over the other protruding portion, and thus the rotation prevention mechanisms enter the locked state. The shapes of the two protruding portions in a view along the radial direction (lateral shape) can be set arbitrarily. For example, the lateral shape of the protruding portions may be rectangular, similarly to the protruding portions 54, 326. Alternatively, the lateral shape of the protruding portions may be a shape that is asymmetrical in the circumferential direction with an inclined face on the forward side and a vertical face on the rear side in terms of the direction of relative movement during engagement, similarly to the protruding portions 414 shown in Embodiment 4. Alternatively, the lateral shape of the protruding portions may be a shape that includes a chamfered face, similarly to the protruding portions 514 shown in Embodiment 5.

In Embodiments 4 and 5, the number of extension portions 412 is not limited to two, and one or a number greater than or equal to three may be provided. In the case of two or more extension portions, it is preferable that the extension portions 412 are arranged at equiangular intervals relative to the central axis 1a. Providing two extension portions is preferable from the viewpoint of the operability of connection to and separation from the female connector 920, and the operability of the cleaning of the connector body (the spiral protrusion 32 and the base end portion 20 in particular). The number of protrusions 452 can be changed according to the number of extension portions 412.

Alternatively, the extension portion may have a tubular shape for covering the outer circumferential face of the lock nut 450, 550 in the circumferential direction. In this case, when the lock nut 450, 550 is attached to the connector body 410, 510, the protrusions 452 are exposed below the tubular extension portion. Protrusions (e.g., protrusion similar to the ribs 57 of Embodiments 1 and 2) or unevenness for preventing slipping may be formed on the outer circumferential face of the extension portion in order to make it possible to easily apply rotation torque to the connector body 410, 510.

In Embodiments 4 and 5, in the case where the first rotation prevention mechanisms are not provided on the protrusions 452, the protrusions 452 can be omitted.

The extension portions 412 described in Embodiment 4, 5 may be provided on the outer tube 40 of the connector body 10, 210 in Embodiment 1, 2. In this case, the protrusions 452 described in Embodiment 4, 5 can be formed on the outer circumferential face of the lock nut 50, 250. Also, the extension portions 412 described in Embodiment 4, 5 may be provided on the lock portion 340 of Embodiment 3. In this case, the protrusions 452 described in Embodiment 4, 5 can be formed on the outer circumferential face of the lock nut 50. In these cases, the protruding portions and the receding portions that constitute the rotation prevention mechanisms can be formed on the lower faces 412a of the extension portions 412 and the upper faces 452a of the protrusions 452.

The configuration described in Embodiment 5 in which the tube 8 is clamped by the small diameter portion 553 and the base end portion 520 on which a fixed protrusion is not formed, can be applied in Embodiments 1 to 4.

Besides the description given above, the configurations described in the embodiments and modified configurations thereof can be applied to other embodiments.

In Embodiments 1 to 5 described above, the male connectors 1 to 5 are attached to the upstream end of a so-called "tube-type" PEG catheter, which is a catheter that is inserted into a patient and has a long portion extending outside of the patient's body. However, the male connector of the present invention can also be attached to the upstream end of a tube that is connected to a so-called "button-type" PEG catheter, which is a catheter that substantially does not extend outside of the patient's body. Furthermore, the male connector of the present invention can also be attached to the upstream end of a transnasal catheter. The male connector of the present invention can be provided at the upstream end of any tube through which an enteral nutrient flows.

INDUSTRIAL APPLICABILITY

The present invention is broadly applicable as a male connector provided at the upstream end of a tube used in enteral feeding. This tube may be a catheter that is indwelled in a patient, as with a PEG catheter or a transnasal catheter, or may be a tube that is connected to such a catheter. Among such catheters, the male connector of the present invention can be preferably used as a male connector provided at the upstream end of a PEG catheter that is indwelled in a patient.

DESCRIPTION OF REFERENCE NUMERALS 1, 2, 3, 4, 5 Male connector
8 Tube
10, 210, 301, 410, 510 Connector body
11 Male luer
13, 313 Flange
14, 454, 554 Receding portion (first rotation prevention mechanism)
17 Channel
20, 520 Base end portion
21 Fixed protrusion
32 Spiral protrusion (first spiral protrusion)
40 Outer tube
41 Female threading (first female threading)
50, 250, 450, 550 Lock nut
50a End face (upper face) of lock nut
52 Female threading (second female threading)
53, 553 Small diameter portion
54, 414, 514 Protruding portion (first rotation prevention mechanism)
57 Rib (protrusion)
231 First engaging protrusion (first rotation prevention mechanism)
252 Second engaging protrusion (first rotation prevention mechanism)
310 Luer portion
316 Receding portion (second rotation prevention mechanism)
326 Protruding portion (second rotation prevention mechanism)
330 Tubular portion (third tubular portion, male tapered face for forming seal)
340 Lock portion
342 Small diameter portion (female tapered face for forming seal)
343 Female threading (third female threading)

412 Extension portion
414b, 454b Inclined face
414c, 454c Vertical face
470 Jig
920 Female connector
921 Insertion portion
925 Male threading

The invention claimed is:

1. A male connector removably attached to an upstream end of a tube used in enteral feeding, the male connector comprising:
    a connector body and a lock nut,
    the connector body including
        a tubular male luer that is provided at a first end of the connector body,
        a first female threading that surrounds the male luer,
        a base end portion that is provided at a second end of the connector body,
        a tubular portion that is located between the male luer and the base end portion,
        a spiral protrusion that protrudes outward along a radial direction from an outer circumferential face of the tubular portion, and
        a channel that extends along a central axis of the connector body and passes through the connector body from the male luer to the base end portion, and
    the lock nut having a hollow tubular shape and being open at two ends, and including a second female threading that is screwed together with the spiral protrusion,
    wherein when the base end portion is inserted into the tube, and the spiral protrusion and the second female threading are screwed together, the tube is arranged in the radial direction between the base end portion and the lock nut, and the base end portion and the lock nut clamp the tube so that the base end portion and the lock nut compress the tube in the radial direction,
    first rotation prevention mechanisms that engage directly with one another are provided on the connector body and the lock nut such that the lock nut does not rotate relative to the connector body when the tube is clamped,
    the male connector can be connected to a female connector that includes an insertion portion for insertion of the male luer and male threading that is to be screwed together with the first female threading, and
    the first rotation prevention mechanisms are configured such that when the lock nut and the female connector are rotated in mutually opposite directions in order to separate the male connector and the female connector that are connected to each other, screwing together of the first female threading and the male threading is loosened, without the lock nut rotating relative to the connector body.

2. The male connector according to claim 1,
    wherein the lock nut includes a small diameter portion that opposes the tube, and
    when the spiral protrusion and the second female threading are screwed together, the base end portion and the small diameter portion clamp the tube in which the base end portion is inserted.

3. The male connector according to claim 2,
    wherein the connector body includes a fixed protrusion that protrudes outward and is formed on an outer circumferential face of the base end portion, and when the spiral protrusion and the second female threading are screwed together, the fixed protrusion and the small diameter portion clamp the tube in which the base end portion is inserted.

4. The male connector according to claim 1, wherein the first rotation prevention mechanisms are formed on a flange that protrudes outward from a position of the connector body between the male luer and the spiral protrusion, and on an end face, on a second female threading side, of the lock nut.

5. The male connector according to claim 1, wherein the first rotation prevention mechanisms are formed on an outer circumferential face of the connector body between the base end portion and the spiral protrusion, and on an inner circumferential face of the lock nut.

6. The male connector according to claim 1,
    wherein the first rotation prevention mechanisms include a protruding portion formed on one of the connector body and the lock nut, and a receding portion formed on another one of the connector body and the lock nut,
    the protruding portion and the receding portion engage in a circumferential direction,
    the protruding portion includes an inclined face on one side in the circumferential direction, and includes a vertical face on another side in the circumferential direction, and
    the receding portion includes an inclined face and a vertical face that respectively oppose the inclined face and the vertical face of the protruding portion when the protruding portion is fitted into the receding portion.

7. The male connector according claim 1,
    wherein the connector body is constituted by two parts, the two parts being a luer portion having the male luer, the base end portion, and the spiral protrusion, and a lock portion having the first female threading,
    the lock portion has a hollow tubular shape and is open at two ends, and is removably attached to the luer portion, and
    second rotation prevention mechanisms that engage with one another are provided on the luer portion and the lock portion such that the lock portion does not rotate relative to the luer portion.

8. The male connector according to claim 7,
    wherein
    the second rotation prevention mechanisms are configured such that when the lock nut and the female connector are rotated in mutually opposite directions in order to separate the male connector and the female connector that are connected to each other, screwing together of the first female threading and the male threading is loosened, without the lock portion rotating relative to the luer portion.

9. The male connector according to claim 7, wherein a liquid-tight seal between the luer portion and the lock portion is formed at a position on a base end portion side relative to the male luer.

10. The male connector according to claim 9, wherein the liquid-tight seal is formed by fitting together of a male tapered face formed on the luer portion and a female tapered face formed on the lock portion.

11. The male connector according to claim 1,
    wherein the connector body includes an extension portion arranged outward of the lock nut, and
    the extension portion is configured such that rotation torque can be applied to the male connector via the extension portion.

12. The male connector according to claim 11,
wherein the extension portion includes at least one bar-shaped member that extends parallel with a lengthwise direction of the connector body, and
the at least one bar-shaped member is arranged so as to protrude outward from an outer circumferential face of the lock nut.

13. The male connector according to claim 1, wherein at least one of the connector body and the lock nut includes a protruding portion or receding portion for facilitating attachment and detachment of the lock nut to and from the connector body.

14. The male connector according to claim 1, wherein the lock portion includes a protruding portion or receding portion for facilitating attachment and detachment of the lock portion to and from the luer portion.

15. The male connector according to claim 13,
further comprising a jig configured so as to engage with the protruding portion or receding portion,
wherein the jig is configured such that rotation torque can be applied to the connector body or the lock nut via the jig.

* * * * *